US009149440B2

(12) United States Patent
Turos et al.

(10) Patent No.: US 9,149,440 B2
(45) Date of Patent: Oct. 6, 2015

(54) NANOPARTICLES FOR DRUG-DELIVERY

(75) Inventors: Edward Turos, Wesley Chapel, FL (US); Jeung-Yeop Shim, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 1873 days.

(21) Appl. No.: 10/570,461

(22) PCT Filed: Sep. 2, 2004

(86) PCT No.: PCT/US2004/028995
§ 371 (c)(1),
(2), (4) Date: Mar. 2, 2006

(87) PCT Pub. No.: WO2005/020933
PCT Pub. Date: Mar. 10, 2005

(65) Prior Publication Data
US 2007/0190160 A1    Aug. 16, 2007

Related U.S. Application Data

(60) Provisional application No. 60/499,904, filed on Sep. 2, 2003, provisional application No. 60/500,750, filed on Sep. 4, 2003, provisional application No. 60/568,746, filed on May 6, 2004.

(51) Int. Cl.
A61K 9/50    (2006.01)
A61K 9/16    (2006.01)
A61K 9/51    (2006.01)

(52) U.S. Cl.
CPC .............. *A61K 9/5138* (2013.01); *A61K 9/5192* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,107,288 A | 8/1978 | Oppenheim et al. |
| 4,540,602 A | 9/1985 | Motoyama et al. |
| 4,767,628 A | 8/1988 | Hutchinson |
| 4,826,689 A | 5/1989 | Violanto |
| 5,110,605 A | 5/1992 | Acharya |
| 5,134,122 A | 7/1992 | Orsolini |
| 5,145,684 A | 9/1992 | Liversidge et al. |
| 5,215,758 A | 6/1993 | Krishnamurthy |
| 5,510,118 A | 4/1996 | Bosch et al. |
| 5,534,270 A | 7/1996 | De Castro |
| 5,648,095 A | 7/1997 | Illum et al. |
| 5,811,388 A | 9/1998 | Friend et al. |
| 5,811,404 A | 9/1998 | De Frees et al. |
| 5,811,422 A | 9/1998 | Lam et al. |
| 5,811,425 A | 9/1998 | Woods et al. |
| 5,814,482 A | 9/1998 | Dubensky, Jr. et al. |
| 6,015,686 A | 1/2000 | Dubensky, Jr. et al. |
| 6,268,222 B1 * | 7/2001 | Chandler et al. ............... 436/523 |
| 2002/0042394 A1 * | 4/2002 | Hogenkamp et al. ........... 514/53 |
| 2002/0052404 A1 * | 5/2002 | Hunter et al. .................. 514/449 |
| 2002/0103517 A1 * | 8/2002 | West et al. ....................... 607/88 |
| 2003/0191108 A1 | 10/2003 | Turos et al. |
| 2004/0063831 A1 * | 4/2004 | Sheppard et al. .............. 524/236 |
| 2004/0102433 A1 * | 5/2004 | Sunagawa et al. ........ 514/210.12 |
| 2004/0167115 A1 | 8/2004 | Dou et al. |
| 2006/0160787 A1 | 7/2006 | Dou et al. |
| 2006/0252809 A1 | 11/2006 | Turos et al. |
| 2007/0265243 A1 | 11/2007 | Turos et al. |
| 2008/0119533 A1 | 5/2008 | Turos et al. |
| 2008/0124371 A1 | 5/2008 | Turos et al. |
| 2008/0167285 A1 | 7/2008 | Turos et al. |
| 2008/0182815 A1 | 7/2008 | Turos et al. |
| 2009/0156654 A1 | 6/2009 | Turos et al. |
| 2010/0204337 A1 | 8/2010 | Turos et al. |
| 2010/0278920 A1 | 11/2010 | Turos et al. |

FOREIGN PATENT DOCUMENTS

| | | |
|---|---|---|
| EP | 0 275 796 B2 | 9/1995 |
| WO | WO 91/13612 A1 | 9/1991 |
| WO | WO 94/12158 A1 | 6/1994 |
| WO | WO 96/37216 A1 | 11/1996 |

OTHER PUBLICATIONS

Ghosh, "Hydrophilic polymeric nanoparticles as drug carriers", Oct. 2000, Indian Journal of Biochemistry & Biophysics, vol. 37, pp. 273-282.*

Calinaud, P. and Gelas, J. "Synthesis of isopropylidene, benzylidene, and related acetals" in Preparative Carbohydrate Chemistry; Hanessian, S. (Ed.); Marcel Dekker, Inc.: NewYork; 1997; Chapter 1.

Fattal, E. et al. "Biodegradable polyalkylcyanoacrylate nanoparticles for the delivery of oligonucleotides" *Journal of Controlled Release*, 1998, 53:137-143.

Kawaguchi, H. "Functional polymer microspheres" *Progress in Polymer Science*, 2000, 25:1171-1210.

Kennedy, W.D. et al. "Thermal data on organic compounds. XVIII. The heat capacity and entropy of *t*-butylethylene" *J. Am. Chem. Soc.*, 1938, 60:1507-1509.

Krishna, P.R. et al. "Asymmetric Baylis-Hillman reaction using sugar acrylates—synthesis of optically active α-methylene-β-hydroxy alkanoates" *Tetrahedron: Asymmetry*, 2001, 12:829-837.

(Continued)

*Primary Examiner* — Robert A Wax
*Assistant Examiner* — Randeep Singh
(74) *Attorney, Agent, or Firm* — Saliwanchik, Lloyd & Eisenschenk

(57) ABSTRACT

This invention relates to polymeric nanoparticles useful for drug delivery with target molecules bonded to the surface of the particles and having sizes of up to 1000 nm, preferably 1 nm to 400 nm, more preferably 1 nm to 200 nm, that are dispersed homogeneously in aqueous solution. The target drug/target substance is covalently bonded to the novel polymeric nanoparticles to secure them from outer intervention in vivo or cell culture in vitro until they are exposed at the target site within the cell. This invention also relates to microemulsion polymerization techniques useful for preparing the novel nanoparticles.

44 Claims, 63 Drawing Sheets

(56) References Cited

OTHER PUBLICATIONS

Kronenthal, D.R. et al. "Oxidative N-dearylation of 2-azetidinones. *p*-anisidine as a source of azetidinone nitrogen" *J. Org. Chem.*, 1982, 47:2765-2768.

Maeder, T. "Sweet medicines" *Scientific American*, 2002, 287:40.

Myszka, H. et al. "Synthesis and induction of apoptosis in B cell chronic leukemia by diosgenyl 2-amino-2-deoxy-β-D-glucopyranoside hydrochloride and its derivatives" *Carbohydr. Res.*, 2003, 338:133-141.

Ouchi, T. and Ohya, Y. "Macromolecular prodrugs" *Progress in Polymer Science*, 1995, 20:211-257.

Shim, J-Y. and Turos, E. "Novel N-thiolated beta-lactam biopolymers for MRSA infections" abstract and poster presented at the 225th ACS National Meeting, Mar. 23-27, 2003 New Orleans, LA.

Uhrich, K.E. et al. "Polymeric systems for controlled drug release" *Chemical Reviews*, 1999, 99:3181-3198.

Wicks, Z.W. et al. (Eds.) Organic Coatings: Science and Technology, John Wiley & Sons, Inc., 1992, vol. I, p. 64.

Woulfe, S.R. et al. "Efficient N-sulfenylation of 2-azetidinones using S-substituted thiophthalimides" *Tetrahedron Letters*, 1985, 26:3891-3894.

Turos, E. et al. "Penicillin-bound polyacrylate nanoparticles: Restoring the activity of β-lactam antibiotics against MRSA" *Bioorganic & Medicinal Chemistry Letters*, 2007, 17:3468-3472.

Turos, E. et al. "Antibiotic-conjugated polyacrylate nanoparticles: New opportunities for development of anti-MRSA agents" *Bioorganic & Medicinal Chemistry Letters*, 2007, 17:53-56.

Abeylath, S.C. and Turos, E. "Glycosylated polyacrylate nanoparticles by emulsion polymerization" *Carbohydrate Polymers*, 2007, 70:32-37.

Abeylath, S.C. et al. "G(yconanobiotics: Novel carbohydrated nanoparticle antibiotics for MRSA and *Bacillus anthracis*" *Bioorganic & Medicinal Chemistry Letters*, 2008, 16:2412-2418.

U.S. Appl. No. 11/854,380, filed Sep. 12, 2007, Turos et al.

Office Action dated Jan. 30, 2012 in U.S. Appl. No. 11/854,380, filed Sep. 12, 2007.

\* cited by examiner homo polyacrylate
(deformed particles)

20:1 copolymer
60-150 nm

13:1 copolymer
60-150 nm

10:1 copolymer
130 nm

7:1 copolymer
40-80 nm

5:1 copolymer
130-150 nm

**2.5:1 copolymer
70 nm**

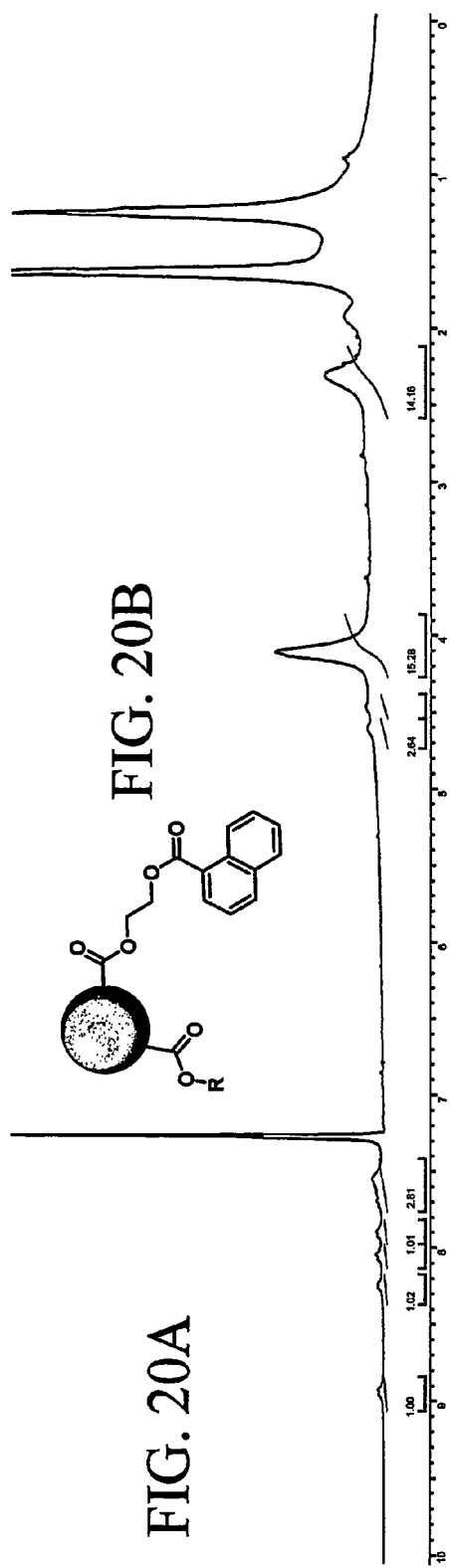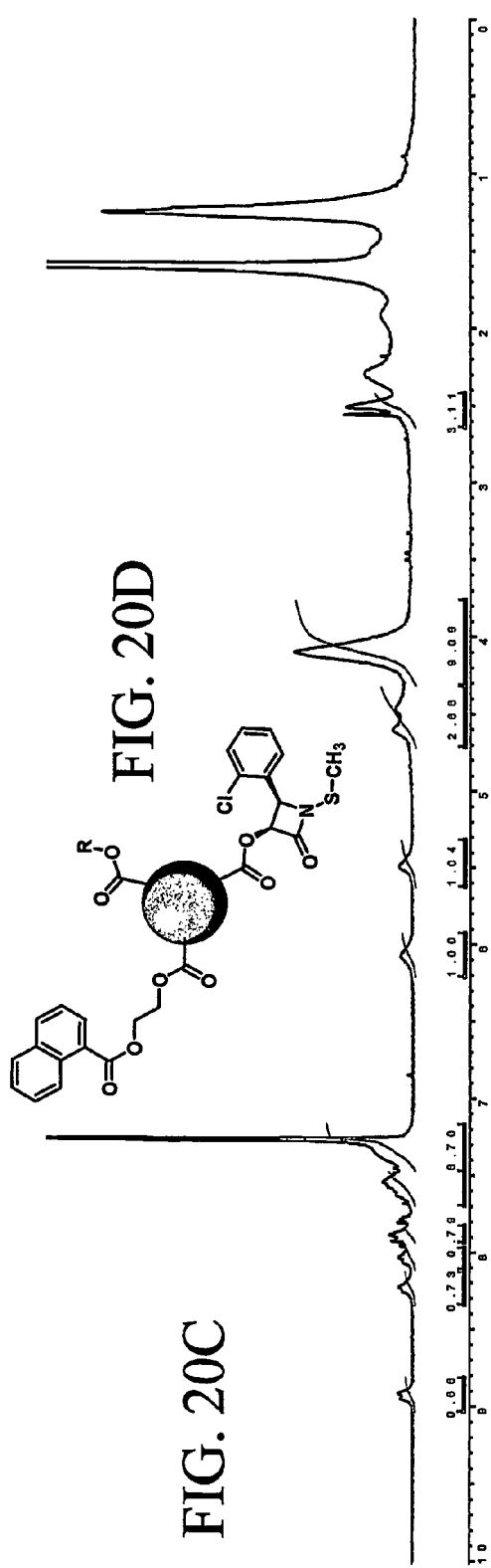
FIG. 20A  FIG. 20B  FIG. 20C  FIG. 20D

NANOPARTICLES FOR DRUG-DELIVERY

CROSS-REFERENCE TO RELATED APPLICATIONS

This application is the National Stage of International Application Number PCT/US2004/028995, filed Sep. 2, 2004, which claims the benefit of U.S. Provisional Application Ser. No. 60/499,904, filed Sep. 2, 2003; U.S. Provisional Application Ser. No. 60/500,750, filed Sep. 4, 2003; and U.S. Provisional Application Ser. No. 60/568,746, filed May 6, 2004, which are hereby incorporated by reference herein in their entireties, including any figures, tables, nucleic acid sequences, amino acid sequences, or drawings.

GOVERNMENT SUPPORT

The subject matter of this application has been supported by a research grant from the National Institutes of Health under grant number R01 AI 51351. Accordingly, the government may have certain rights in this invention.

FIELD OF THE INVENTION

This invention relates to a unique process for the preparation of nanoparticles bearing bioaffecting agents using microemulsion polymerization. The bioaffecting agent is chemically modified for incorporation onto the surface of the nanoparticle.

This invention further relates to a composition comprising water-dispersed nanoparticles having a drug bonded thereto via an acrylic or vinyl moiety, and administration of same.

BACKGROUND OF THE INVENTION

The subject invention relates to the art of delivering bioaffecting agents, such as drugs, to bio-systems, and, in particular, for rendering agents which are substantially non-dissoluble in an aqueous environment available for interaction with a host bio-system, such as a human or other animal.

Bio-systems, such as humans, plants, insects, fish, birds, and mammals, are primarily aqueous systems. In order to effectively deliver a bioaffecting agent to such bio-systems, it is necessary to make the agent available for interaction with physiological activity in the bio-system. This is referred to herein as "bio-availability". In the case of bioaffecting agents that are non-dissoluble in an aqueous environment, as well as in the case of those that are only poorly water-soluble, effective administration of the bioaffecting agent can be difficult due to inadequate bio-availability of the agent and consequent low pharmacological activity. These solubility problems affect many parameters of delivery, such as the method of administration, the rate of administration, the concentration of administration, etc.

It is known that rate of dissolution of drug particulates can be increased by increasing the ratio of surface area/mass of the solid, for example, by decreasing the particle size. Consequently, methods of making finely divided drugs have been studied, and efforts have been made to control the size and size range of drug particles in pharmaceutical compositions. For example, dry milling techniques have been used to reduce particle size and thereby influence drug absorption. However, in conventional dry milling, as discussed by Lachman et al., The Theory and Practice of Industrial Pharmacy, Chapter 2, "Milling", p. 45 (1986), the limit of fineness is reached in the region of about 100 μm (=100,000 nm), where the milled material begins to cake onto the surfaces of the milling chamber. Lachman et al. note that wet grinding is beneficial in further reducing particle size, but that flocculation restricts the lower particle size limit to approximately 10 μm (=10,000 nm). There tends to be a bias in the pharmaceutical art against wet milling due to concerns associated with contamination. Commercial airjet milling techniques have provided particles ranging in average particle size from as low as about 1 μm to 50 μm (=1,000 nm to 50,000 nm).

Other techniques for preparing pharmaceutical compositions with enhanced aqueous solubility properties include loading drugs into liposomes or polymers, such as, for example, during emulsion polymerization. However, such techniques have inherent problems and limitations. For example, a lipid-soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator (which can be toxic) at the end of the manufacturing process.

U.S. Pat. No. 4,540,602 discloses a solid drug pulverized in an aqueous solution of a water-soluble high molecular weight substance using a wet grinding machine. However, the '602 patent teaches that, as a result of such wet grinding, the drug is formed into finely divided particles ranging from 0.5 μm (500 nm) to less than 5 μm (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance, and results in the formation of non-crystalline nanoparticles. Furthermore, precipitation techniques for preparing particles tend to provide particles contaminated with solvents. Such solvents are often toxic and can be very difficult, if not impossible, to adequately remove to pharmaceutically acceptable levels. Accordingly, precipitation methods are usually impractical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 5,145,684 describes a method for providing drug particles having an effective average particle size of less than about 400 nm. The method includes wet milling the drug in the presence of a grinding medium in conjunction with a surface modifier. As in previous methods, the '684 protocol requires grinding or milling to achieve size reduction. The method further requires the use of an additive in the form of a surface modifier.

Moreover, drugs prepared by milling, even wet milling such as that described in the '684 disclosure, are subject to degradation resulting from heat as well as physical and chemical trauma associated with fracture. Grinding also creates "hot spots," i.e., volumes of localized higher temperatures that can exceed the melting point or degradation of the drug. The process is also lengthy, requiring attrition exposure over several days. This type of process effectively exposes the drug to a long "heat history", wherein exposure to elevated temperatures has been significant, and the purity and potency of the drug is diminished to a significant extent. Furthermore, particles reduced by milling are often contaminated by, the residue of the grinding operations, especially when ball milling is used and the grinding balls are worn down by abrasion.

It has also been known in the art of drug delivery to improve bio-availability by aggregating substantially non-dissoluble active ingredients on the surface of soluble substrates, such as water-soluble beads. The active ingredient can be deposited on such substrates by spraying a solution of the active ingredient over a fluidized bed while "flashing off" the solvent used for the active ingredient. This method is highly inefficient in that it requires several hours to deposit a sufficient amount of active ingredient to prepare a useable delivery system. Furthermore, an additional ingredient which is unnecessary to the system must be used, i.e., the solvent required to dissolve the active ingredient. As previously mentioned, the solvent must be flashed off during aggregation. Thus, this system is a long and cumbersome process and does not provide efficiency of dosage delivery.

Solubilization techniques for drugs that have low aqueous solubility require the use of organic solvents for processing in a solution state. This requires the use of expensive recovery systems for solvent handling capability. When general melt processing techniques are used to form dispersions, bulk melting and mixing steps often expose the drug to a prolonged heat history.

Particulate carriers have been used in order to achieve controlled, parenteral delivery of therapeutic compounds. Such carriers are designed to maintain the active agent in the delivery system for an extended period of time. Examples of particulate carriers include those derived from polymethyl methacrylate polymers, as well as microparticles derived from poly(lactides) (see, e.g., U.S. Pat. No. 3,773,919), poly (lactide-co-glycolides), known as PLG (see, e.g., U.S. Pat. No. 4,767,628) and polyethylene glycol, known as PEG (see, e.g., U.S. Pat. No. 5,648,095). Polymethyl methacrylate polymers are nondegradable, while PLG particles biodegrade by random nonenzymatic hydrolysis of ester bonds to lactic and glycolic acids, which are excreted along normal metabolic pathways.

For example, U.S. Pat. No. 5,648,095 describes the use of microspheres with encapsulated pharmaceuticals as drug delivery systems for nasal, oral, pulmonary, and oral delivery. Slow-release formulations containing various polypeptide growth factors have also been described. See, for example, International Publication No. WO 94/12158, U.S. Pat. No. 5,134,122 and International Publication No. WO 96/37216.

Fattal et al., Journal of Controlled Release 53:137-143 (1998) describes nanoparticles prepared from polyalkylcyanoacrylates (PACA) having adsorbed oligonucleotides.

U.S. Pat. Nos. 5,814,482 and 6,015,686 disclose Eukaryotic Layered Vector Initiation Systems (ELVIS vectors), particularly those derived and constructed from alphavirus genomes (such as Sindbis virus), for use in stimulating an immune response to an antigen, in methods of inhibiting pathogenic agents, and in delivery of heterologous nucleotide sequences to eukaryotic cells and animals, among others.

While antigen-adsorbed PLG microparticles offer significant advantages over other more toxic systems, adsorption of biologically active agents to the microparticle surface can nonetheless be improved. For example, it is often difficult or impossible to adsorb charged or bulky biologically active agents, such as polynucleotides, large polypeptides, and the like, to the microparticle surface. Thus, there is a continued need for flexible delivery systems for such agents, and particularly for drugs that are highly sensitive and difficult to formulate.

"Controlled release" refers to the release of an agent such as a drug from a composition or dosage form in which the agent is released according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response provide for many inherent benefits that are not achieved with the corresponding short acting, immediate release preparations. For example, in the treatment of chronic pain, controlled release formulations are often highly preferred over conventional short-acting formulations.

Controlled release pharmaceutical compositions and dosage forms are designed to improve the delivery profile of agents, such as drugs, medicaments, active agents, diagnostic agents, or any substance to be internally administered to an animal, including humans. A controlled release composition is typically used to improve the effects of administered substances by optimizing the kinetics of delivery, thereby increasing bioavailability, convenience, and patient compliance, as well as minimizing side effects associated with inappropriate immediate release rates such as a high initial release rate and, if undesired, uneven blood or tissue levels.

As indicated above, the term "bioavailability" is used to describe the degree to which a drug becomes available at the site(s) of action after administration. The degree and timing in which an agent such as a drug becomes available to the target site(s) after administration is determined by many factors, including the dosage form and various properties such as dissolution rate of the drug. It is well known that some drug compositions suffer from poor bioavailability because of poor solubility of the active ingredient itself.

Numerous methods have been developed for enhancing the bioavailability of poorly soluble drugs. Particle size reduction, such as nanoparticulate forms of the agent, is one such method since the dissolution rate of a compound is related to the particle size. Nanoparticulate compositions comprise poorly water-soluble drug or agent particles having an extremely small particle size, i.e., less than one micron. With a decrease in particle size, and a consequent increase in ratio of surface area/mass, a composition tends to be rapidly dissolved and absorbed following administration. For certain formulations, this characteristic can be highly desirable, as described, for example, in U.S. Pat. Nos. 5,145,684; 5,510,118; 5,534,270; and 4,826,689; which are specifically incorporated by reference. However, rapid dissolution is contrary to the goal of controlled release. Known controlled release formulations do not present a solution to this problem.

Prior art teachings of the preparation and use of compositions providing for controlled release of an active compound provide various techniques for extending the release of a drug following administration. However, none of the techniques suggest a successful method of administering a nanoparticulate formulation.

Exemplary controlled release formulations known in the art include specially coated pellets, microparticles, implants, tablets, minitabs, and capsules in which the controlled release of a drug is brought about, for example, through selective breakdown of the coating of the preparation, through release through the coating, through compounding with a special matrix to affect the release of a drug, or through a combination of these techniques. Some controlled release formulations provide for pulsatile release of a single dose of an active compound at predetermined periods after administration.

U.S. Pat. No. 5,110,605 refers to a calcium polycarbophil-alginate controlled release composition. U.S. Pat. No. 5,215,758 refers to a controlled release suppository composition of sodium alginate and calcium salt. U.S. Pat. No. 5,811,388 to refers to a solid alginate-based formulation including alginate, a water-swellable polymer, and a digestible hydrocarbon derivative for providing controlled release of orally administered compounds.

WO 91/13612 refers to the sustained release of pharmaceuticals using compositions in which the drug is complexed with an ion-exchange resin. The specific ion-exchange resin described in this published patent application is AMBERLITE IRP 69®, a sodium polystyrene sulphonate resin.

U.S. Pat. No. 5,811,425 refers to injectable depot forms of controlled release drugs made by forming microencapsule matrices of the drug in biodegradable polymers, liposomes, or microemulsions compatible with body tissues. U.S. Pat. No. 5,811,422 refers to controlled release compositions obtained by coupling a class of drugs to biodegradable polymers, such as polylactic acid, polyglycolic acid, copolymers of polylactic and polyglycolic acid, polyepsilon caprolactone, polyhydroxy butyric acid, etc.

U.S. Pat. No. 5,811,404 refers to the use of liposomes having prolonged circulation half-lives to provide for the sustained release of drug compositions.

Following an administration of a drug in a living system, the active substance is distributed throughout the body as a function of its physicochemical properties and molecular structure. The final amount of drug reaching its target site may only be a small fraction of the administered dose. Accumulation of drug at the non-targeted site may lead to adverse effect and undesirable side reactions. Therefore, targeting of drug to specific body sites is desirable.

One way of modifying the biodistribution of drugs in the body is to entrap them in ultrafine drug carriers. Among these carriers, liposomes, nanoparticles and pharmacosomes have been extensively studied. The use of liposomes as drug targeting agents is found to be limited due mainly to the problems of low entrapment efficiency, drug instability, rapid drug leakage, and poor storage stability. With the aim of overcoming these problems, the production of polymeric nanoparticles has been investigated since the last two decades. Nanoparticles are defined as solid colloidal particles ranging in size from about 10 nm to 1000 nm.

A large number of studies have reported recent advances in drug targeting possibilities and sustained release action with nanoparticles encapsulating drugs. In vivo studies have also been reported with special attention to the reticuloendothelial system (RES). Some in vivo studies concerning nanoparticles administration by oral and ocular routes have also been reported in the literature with respect to the possible improvements of bioavailability. These polymeric nanoparticles should be non antigenic, biocompatible, and biodegradable.

The important characteristics of the particles used for targeting at specific body sites have been found to be influenced mainly by two factors: (i) the size of the nanoparticles and (ii) the surface characteristics of the nanoparticles. Particles smaller than 7 μm, and especially nanoparticles, are not filtered in the lung and their biodistribution is dependent on their interaction with reticuloendothelial system (RES). Biodegradable nanoparticles are mainly taken up by the Kupffer cells in the liver while a small amount of these particles go to macrophages in spleen and bone marrow. Bone marrow uptake and targeting at other sites can be modified drastically by reducing the particle size. Nanoparticles of 200 nm diameter and above have biodistribution dependent on their interaction with RES. The distribution, however, can be reversed if the particle size is made much smaller (for example, below 100 nm) and particle surfaces are made hydrophilic. These small particles in the blood serum do not adsorb serum protein through opsonisation and, as a result, their circulation time in blood is considerably increased. Hydrophobic particles are removed from the circulation very rapidly due to opsonisation. Nanometer-sized particles with a hydrophilic surface remain in blood for a longer period of time so that targeting at specific sites may be facilitated.

It is desirable to provide stable dispersible drug particles in the sub-micrometer size range that can be readily prepared in the absence of size reduction by grinding or milling. Moreover, it would be highly desirable to provide pharmaceutical compositions having enhanced bio-availability. There also remains a need in the art for controlled release nanoparticulate compositions.

SUMMARY OF THE INVENTION

The subject invention provides unique processes for the preparation of polymeric nanoparticles with targeted materials bonded to the surface of the particles and having a size of up to 1000 nm, dispersed homogeneously in aqueous solution.

One specific embodiment comprises one or more dissolving modified bioaffecting agents in a polymerizable monomer to form a homogeneous solution, pre-emulsifying the solution with the addition of an emulsifier in aqueous solution, and initiating free-radical polymerization of the modified bioaffecting agent. Another embodiment comprises mixing one or more bioaffecting agents and a polymerizable monomer at room temperature to form a homogeneous solution; adding an aqueous solution containing an emulsifier to the homogeneous solution; agitating the mixture for a sufficient period of time to form a milky pre-emulsified state; and adding a water-soluble initiator, wherein the initiator generates free radicals, for a sufficient period of time for polymerization at a temperature greater than room temperature. Advantageously, the bioaffecting agent(s) used in the compositions and processes of the invention may range in physical state from insoluble solids to highly viscous liquids.

These polymeric nanoparticles are subcolloidal size, 1 nm to 1000 nm, preferably 1 nm to 400 nm, and more preferably 1 nm to 200 nm, with the target drug/target substance covalently bonded to the surface of the particles.

In addition, the resulting polymeric nanoparticles of this invention are dispersed homogeneously in aqueous phase and can be free of any toxic material, obviating a number of disadvantages associated with the prior art.

This invention also provides a process for the bonding of a target drug/target substance to the polymeric nanoparticles to secure them from outer intervention in vivo or in vitro (e.g., in cell culture or ex vivo) until they are exposed at a desired target site, such as within a target cell.

The subject invention further provides a composition of nanoparticles soluble in aqueous media. The novel nanoparticles comprise a drug that is soluble in organic solution and not miscible in aqueous solution covalently bonded with an acrylic or vinyl monomer selected by its ability to form a homogeneous solution with the drug and by its ability to polymerize.

The polymeric nanoparticles of subject invention can be prepared by using the novel technique of microemulsion polymerization. The resulting aqueous solution of polymeric nanoparticles preferably comprises about 1 to 100 parts per weight of water or buffer, about 1 to 80 parts per weight of polymeric nanoparticles, about 0.001 to 10 parts per weight of emulsifier, and about 0.00001 to 5 parts per weight of radical initiator, based on the weight of the solution.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 20A-20D. FIG. 20A shows the $^1$H NMR spectra for the produced fluorescent acrylic polymer of FIG. 20B. FIG. 20C shows the $^1$H NMR of a fluoresce-active polymeric nanoparticle with a pendent β-lactam drug of FIG. 20D.

FIGS. 21A and 22A show the electron microscopy of the fluorescent acrylic polymers of FIGS. 21B and 22B.

FIG. 53A shows the $^1$H NMR spectra for anthracenyl fluorescence-active copolymer (FIG. 53B).

FIG. 66A shows $^1$H NMR spectra of anthracenyl acrylates (FIG. 66B).

DETAILED DESCRIPTION OF THE INVENTION

The subject invention is directed to the art of preparing polymeric nanoparticles, polymeric nanoparticles bearing bioaffecting agents, and the administration of such nanoparticles to a bio-system, such as eukaryotic or prokaryotic cells, in vitro or in vivo.

The subject invention relates to the novel technique of microemulsion polymerization to prepare polymeric nanoparticles of the subject invention Without being limited by theory, the methods of the subject invention are directed to polymerizations of monomers entrapped inside an emulsion of micelles. As known in the art, micelles aggregate at the critical micelle concentration (CMC) into a roughly spherical shape. The amphiphillic material self-assembles in water with the hydrophobic tails radially arranged to form a hydrophobic core. The hydrophilic heads form the surface of the sphere, seeking maximum exposure to water.

When water insoluble or highly viscous drug molecules are added to the aqueous solution, they seek an area most protected from the water molecules and are entrapped within the hydrophobic core of the micelle. When water soluble drug molecules are added to the water, the molecule can bind to the hydrophilic heads of the micelle.

The novel processes of the subject invention modify the water insoluble or highly viscous bioaffecting agent. A linker and an acrylic group are covalently bonded to the bioaffecting agent. Advantageously, bioaffecting agents can be synthesized from commercially available reagents or a commercially available bioaffecting agent can be modified. The acrylic group provides a means for attaching the bioaffecting agent to the polymer backbone. The linker group maintains the agent's attachment to the polymer until exposed to agents endogeneous or exogenous to the target cell. Then, the bonds attaching the linker to the agent are broken, thereby releasing the agent to or within the target cell. In another embodiment of the subject invention, the polymer backbone that forms into a nanoparticle is bonded with biodegrable linkers. When the linkers biodegrade, the backbone dissolves releasing the agent.

A radical initiator instigates polymerization of the monomers and modified bioaffecting agents trapped inside the micelle. Thus, the subject invention includes polymeric nanoparticles having at least one bioaffecting arrayed radially around the surface of the nanoparticle. The resulting polymeric nanoparticle is advantageously uniform in size and is designed to release the drug once the nanoparticle has reached the target cell.

Figure 38:
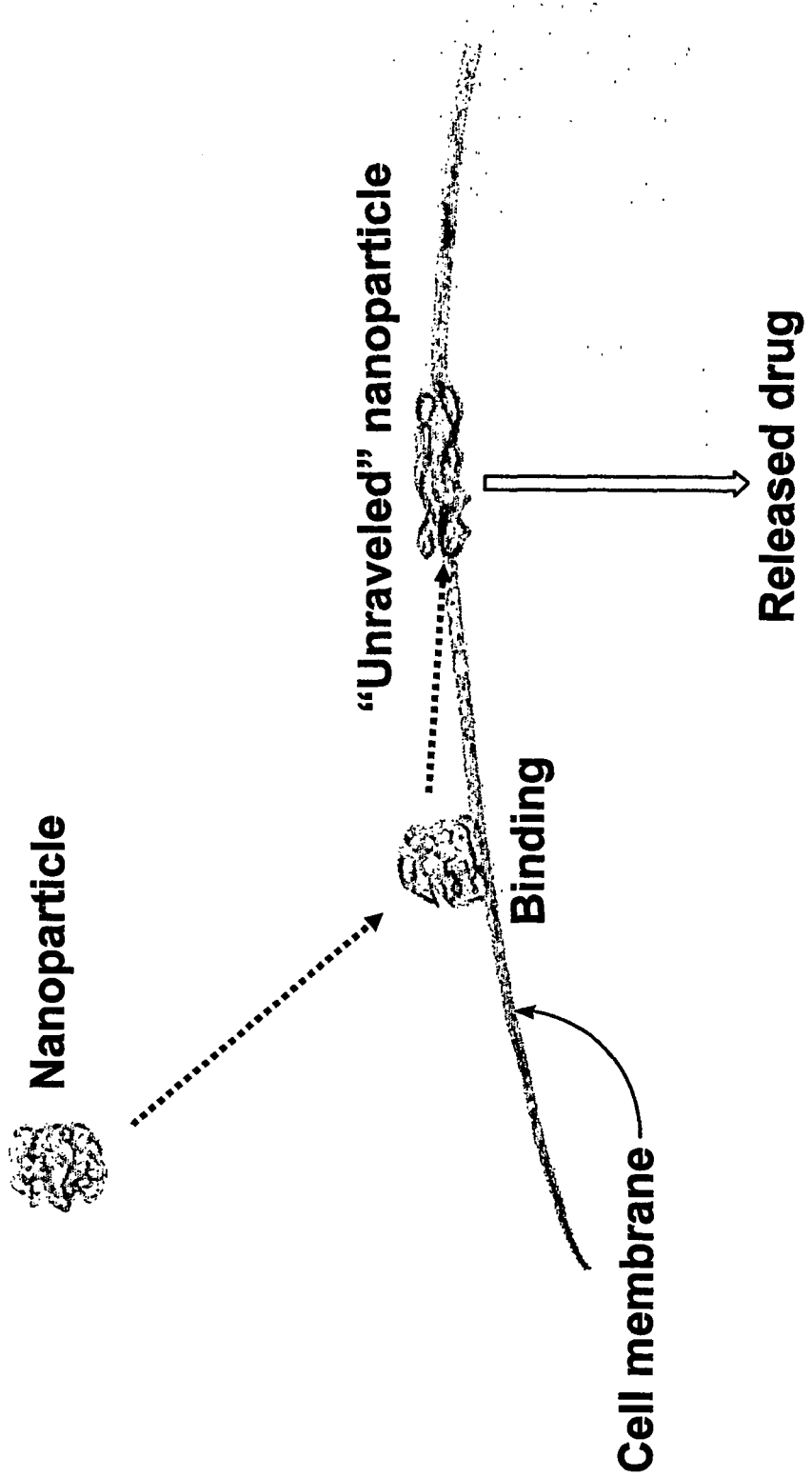
FIG. 38 shows a theory on the mode of drug delivery to a bacterial cell utilizing nanoparticles prepared in accordance with the subject invention.

Without being limited by theory, the drug delivery mechanism of the subject invention is illustrated in FIG. 38. Briefly, a drug nanoparticle prepared in accordance with the processes of the subject invention is administered to a host biosystem, such as prokaryotic or eukaryotic cells, in vitro or in vivo or ex vivo. The nanoparticle binds to the surface of the membrane of targeted cells, such as bacterial cells, fungal cells, cancer cells, or inflammatory cells. For sugar coated nanoparticles, the sugars are known to combine with proteins and lipids on cell surfaces, thereby providing a binding mechanism. The linkage covalently bonding the drug or other bioaffecting material to the nanoparticle is cleaved by an endogenous or exogenous agent capable of cleaving the linkage (such as an endogenous or exogenous enzyme), thereby releasing the drug and unraveling the nanoparticle at the cell membrane.

Figure 1:
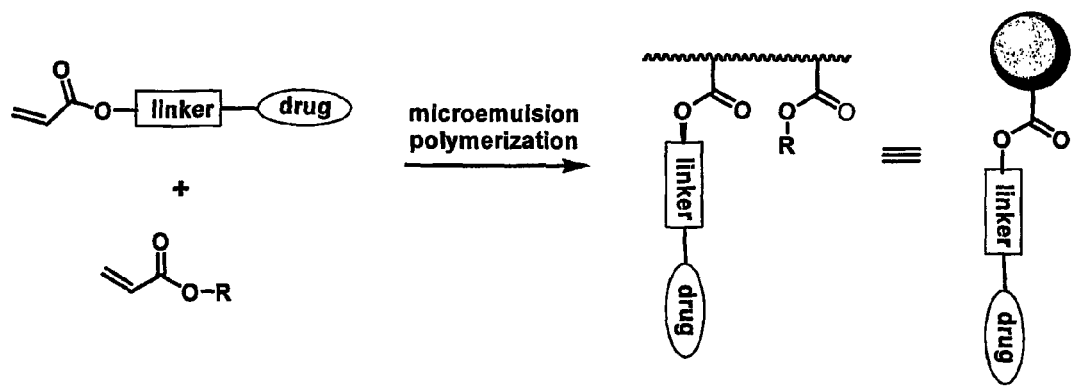
FIG. 1 shows a flow diagram of the microemulsion polymerization.

One aspect of the subject invention pertains to processes for synthesizing polymeric nanoparticles. FIG. 1 illustrates a general flow diagram of the process of the subject invention for a poly(ethyl acrylate) drug nanoparticle. The R group includes hydrogen, alkyl, alkenyl, alkoxy, aryl, heteroaryl, substituted alkyl, and substituted alkenyl. The microemulsion polymerization used to prepare the polymeric nanoparticles possesses four major components: 1) acrylic drug monomer, 2) acrylic or vinyl co-monomer, 3) surfactant, and 4) deionized water. The acrylate group on the modified drug and the additional acrylate group react to form a polymer backbone. The carboxy group and the modified drug are individually attached to the polymer backbone. Advantageously, the bioaffecting agents and their delivery vehicles are assembled simultaneously without the need for further modification.

Figure 30:
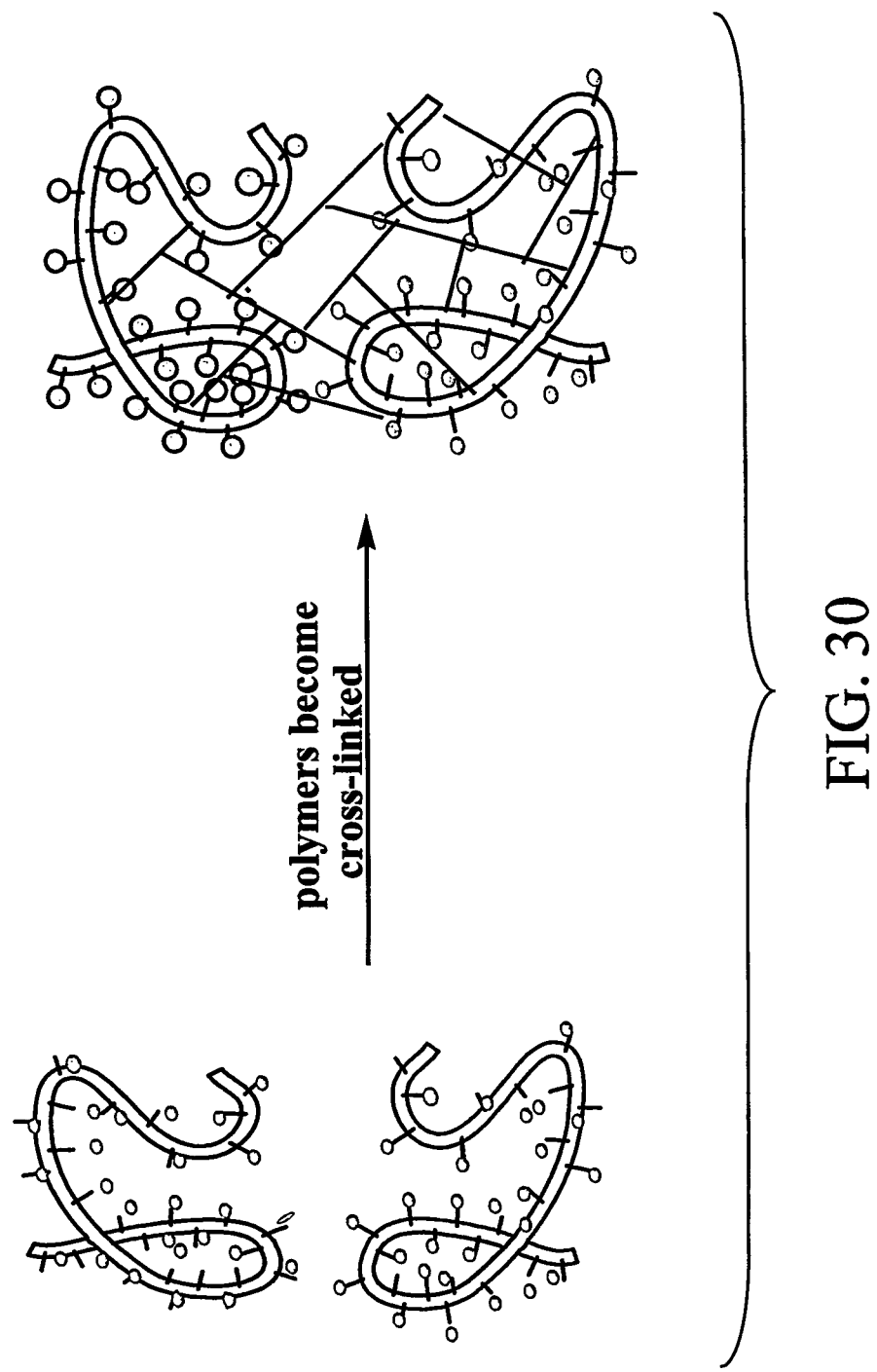
FIG. 30 shows a flow diagram for creating crosslinks within a nanoparticle polymer.

In one embodiment, the process comprises dissolving synthetically modified drug monomers in polymerizable hydrocarbon monomers to form a homogenous solution, pre-emulsifying the mixture with the addition of an aqueous solution containing an emulsifier, and initiating free-radical polymerization. The process further comprises creating cross-links within the nanoparticle polymers as shown in FIG. 30. Also, other agents can be added to control the properties of the polymeric nanoparticle solution. Chain transfer agents and other polymerization modifiers may be added to the monomer premix. Skilled artisans would understand that the principles and chemical types are the same as for acrylic polymerization in general. The main object of the chain transfer agent is to control the molecular weight by reducing the growing chain length. Additives also may be added to the emulsion solution for enhancing its stability.

The temperature of the dissolving step occurs at room temperature (about 23° C.) or higher. Some drug monomers can be dissolved in co-monomers at room temperature. Preferably, the dissolving step takes place at about 30° C. to about 80° C. More preferably, the dissolving step takes place at about 70° C. The dissolving step can also include agitation.

The monomers utilized in the processes of the subject invention play two important roles in the synthesis of nanoparticles. The monomers act as co-monomers in polymerization with the synthetically modified drug monomers to form a polymer backbone. Advantageously, the polymer backbone provides enhanced environmental stability and selectivity within the host biosystem. The monomers also act as solvents for dissolving the synthetically modified drug monomers to form a homogenous state. Thus, the monomers are matched to the targeted drug monomer. For example, if the monomer has low solubility for the drug or other bioaffecting material, the microemulsion polymerization is poor. Additionally, some monomers have low reactivity for the radical polymerization. Advantageously, there are a multiplicity of monomers, including acrylic monomers, that are commercially available or easily synthesized from commercially available starting materials.

Preferably, the monomer utilized in the dissolving step is an acrylic monomer, a vinyl monomer, or a modified resin of either. Monomers utilized by the subject invention include, but are not limited to, acrylonitrile, acrylic acid, maleic acid, methyl acrylate, ethyl acrylate, butyl acrylate, butyl methacrylate, 2-ethylhexyl acrylate, methoxyethyl acrylate, dimethylamino acrylate, methacrylic acid, isobutyl methacrylate, 2-ethyl hexyl methacrylate, lauryl methacrylate, stearic methacrylate, dimethyl amino methacrylate, allyl methacrylate, 2-hydroxyethyl acrylate, 2-hydroxy propyl acrylate, 2-hydroxy ethyl methacrylate, modified acrylamide, modified methacrylamide glycidyl acrylate, styrene, vinyl acetate, vinyl toluene, and synthetically modified acrylics. Preferably, the monomer is ethyl acrylate.

In one embodiment, the synthetically modified acrylics are carbohydrates modified with acrylates. FIG. 24 illustrates some carbohydrate monomers utilized in accordance with the subject invention. The general scheme for preparing the carbohydrate monomers is shown in Scheme A.

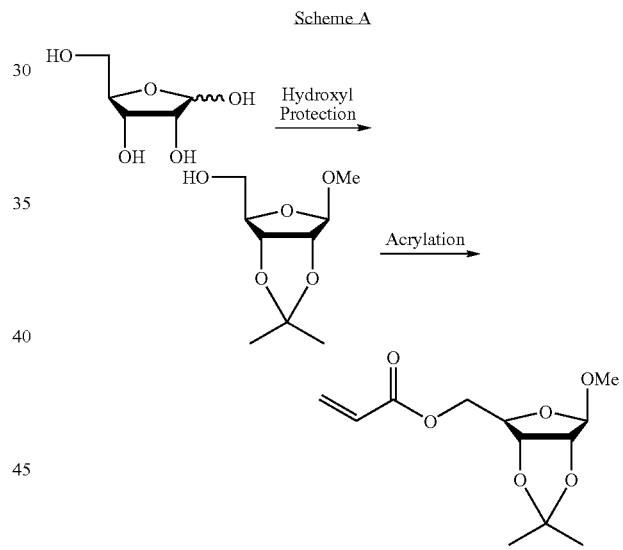

Carbohydrates modified with acrylics include, without limitation, methyl 2,3-O-iso-propylidine-β-D-ribofuranose-5-acrylate; 2,3:5,6-Di-O-iso-propylidine-α-D-mannofuranose-1-acrylate; 1,2:5,6-Di-O-iso-propylidine-α-D-glucofuranose-3-acrylate; 1,2:3,4-Di-O-iso-propylidine-α-D-galactopyranose-6-acrylate; and N-acryloyl 1,3,4,6-tetra-O-acetyl-g-D-glucosamine. Additionally other carbohydrates that are modifiable for use in the subject invention include, without limitation, D-glucose (FIG. 24B), α-D-glucopyranose, β-D-glucopyranose, D-fructose, α-D-fructofuranose, D-fructopyranose, D-ribose (FIG. 24A), D-mannose (FIG. 24C), D-galactose (FIG. 24D), D-glucasamine (FIG. 24E), amylase, amylopectin, cellulose, sugar derivatives, for example, sugar alcohols, sugar acids, amino sugars, and sialic acids, maltose, L-sorbose, cellobiose, sucrose, lactose, glycogen, hyaluronate, and lectins.

In yet another embodiment, the modified acrylics are modified with the addition of a targeting agent. The targeting agent provides a mechanism to direct the polymeric drug nanoparticle to the target cell, where the drug nanoparticle binds to the cell.

The emulsifiers in the pre-emulsifying step are preferably added as an aqueous solution, and the resulting mixture requires agitation for a sufficient period of time until the solution reaches a milky pre-emulsified state. This agitation is often mechanical. For example, in a benchtop laboratory embodiment, a magnetic stirrer at high speed is sufficiently vigorous.

Any anionic, cationic, or nonionic surfactant can be used as the emulsifier. The emulsifiers include, but are not limited to, lauryl alcohol (+6EO); nonyl phenol (+10EO, +15EO, +30EO); sodium lauryl sulphate; lauryl sulphate (+2EO, +4EO) Na salt; sodium dodecylbenzene sulphonate; sodium dioctyl sulphosuccinate; polyvinyl alcohol; polyol; unsaturated and/or saturated sodium or potassium salts of fatty acids; and all synthetically modified PEG surfactants. The emulsifiers (or the surfactants), which can control many of the properties of emulsion polymers, are very important for successful formulation. There is a critical concentration below which an emulsifier will not form micelles. The minimum level required for micelle formation is known as the critical micelle concentration (CMC).

Emulsifiers are classified according to the ionic type of the hydrophilic group, ionic or non-ionic. Ionic emulsifiers generally have a lower CMC than non-ionic emulsifiers and they provide low particle size emulsions. However, they may, in certain circumstances, have a problem in long term storage. In the case of non-ionic emulsifiers, they need higher CMC level because of their low water solubility so that it leads to the formation of small aggregates or grainy emulsions. However the particles are formed, they are very stable in aqueous system. As a result of these advantages and disadvantages, ionic/non-ionic emulsifier mixtures can be employed in emulsion polymerization. Therefore, the factors for selecting the emulsifiers depend on the formulation based on the chemical or physical properties of the applied drug monomer and co-monomer, radical initiator, and aqueous system in this case.

The free-radicals utilized in the subject invention include, but are not limited to, peroxides; persulphates; alkyl hydroperoxides; sodium, ammonium, and potassium salts of persulphate; thiosulphates; metabisulphites; and hydrosulphides. The initiator must be water soluble, and the free radicals may be generated thermally or by use of an oxidation-reduction (or redox) couple. The major initiators used in emulsion polymerization are persulphates. Even though initiating efficiency and half life of persulphates vary, ammonium persulphate is preferred in practice because of its better solubility. Hydroperoxides are often used particularly as a post reaction initiator to kill the unreacted monomers after emulsion polymerization.

The rate of free radical generation increases with temperature, and it is normal to employ reaction temperatures of 60-90° C. when using thermal generation techniques. However, when redox couples (thiosulphates, metabissulphites, and hydrosulphides) are employed, the rate of free radical generation is increased to that provided by thermal generation at the same temperature. Therefore, when using redox couples, reaction temperatures can be made as low as 30° C., or even room temperature. The free radicals can be added as an aqueous solution repeatedly until a milky solution is formed.

The aqueous media utilized in the pre-emulsifying and initiating steps include deionized water or nano-pure water. As known to those skilled in the art, a buffer solution may be necessary depending on the surfactant and particle stabilization.

The resulting aqueous solution of polymeric nanoparticles preferably comprises about 1 to 100 parts per weight of water or buffer, about 1 to 80 parts per weight of polymeric nanoparticles, which the bio-active molecules are conjugated, about 0.001 to 10 parts per weight of emulsifier, and about 0.00001 to 5 parts per weight of radical initiator, based on the weight of the solution. Advantageously, emulsions of the polymeric nanoparticles are stable for at least 12 months and tolerate about 70° C. without degradation.

Figure 36:
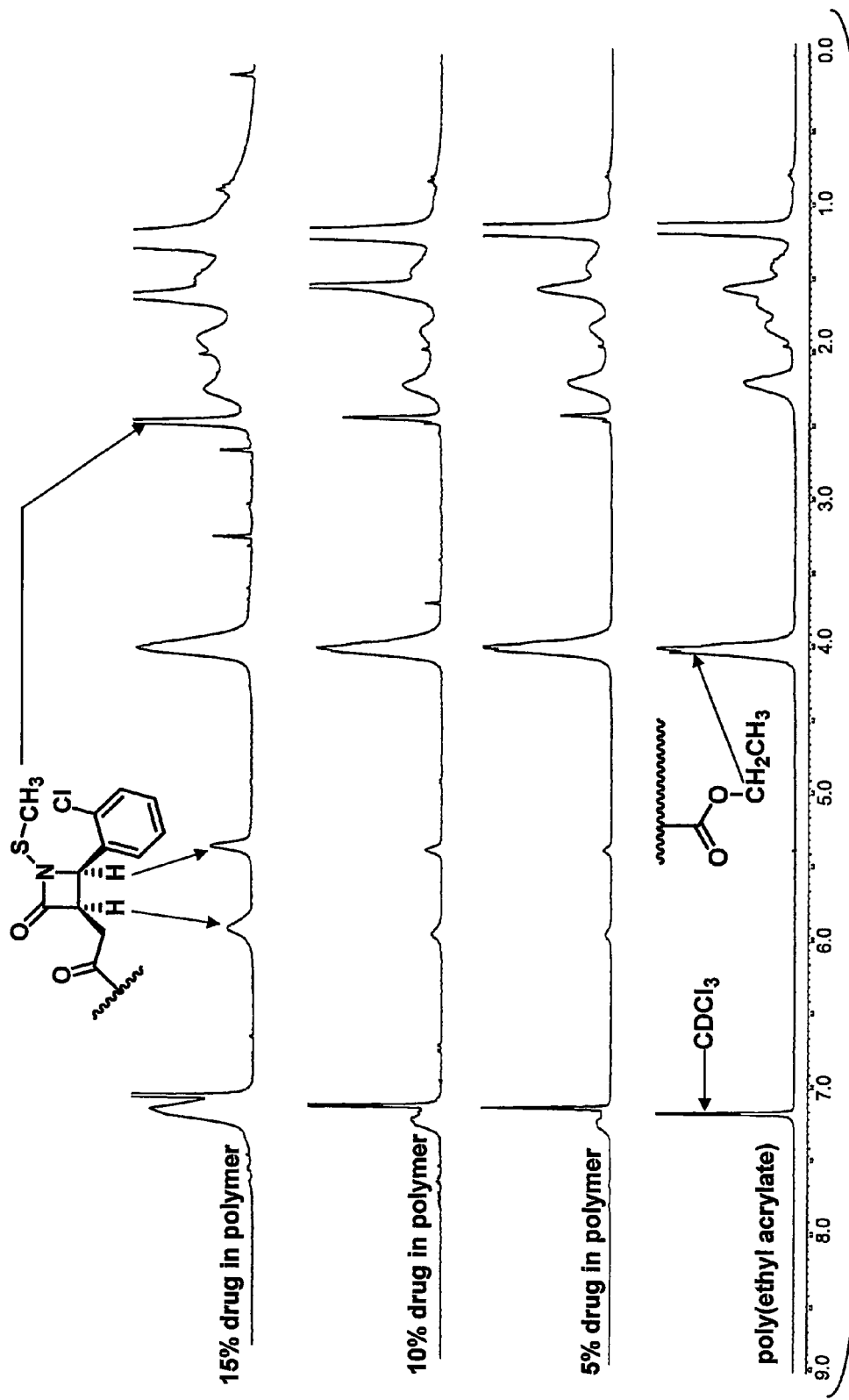
FIG. 36 shows the bioactivity of poly(ethyl acrylate) nanoparticles on MRSA, β-lactam containing nanoparticles on MRSA, and β-lactam containing nanoparticles on MSSA in fixed disk loading amounts.
Figure 39:
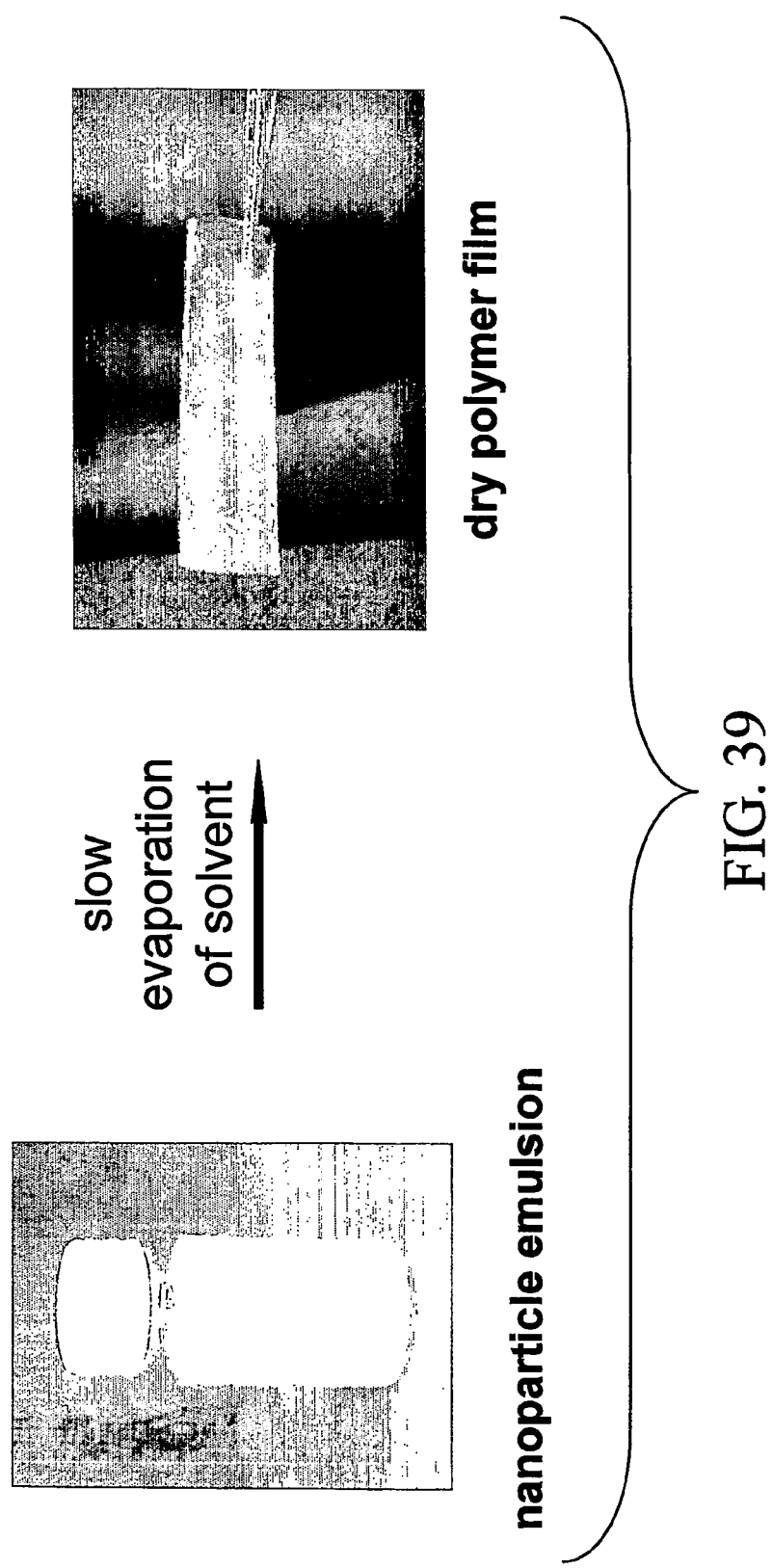
FIG. 39 shows a dry polymer film prepared by evaporation of nanoparticle emulsion.

The polymeric drug nanoparticles prepared in accordance with the methods of the subject invention can be further modified to enhance administration. In one embodiment, a dry polymer film is prepared by a coalescing process (FIG. 39). The polymeric particles experience an irreversible structural change during film formation. The particles, upon evaporation of water, come into contact, fuse and form a uniform film through a process called coalescense. In general it is assumed that the film formation can be separated into the following three stages: Stage 1: Water evaporates slowly and thus polymer particles become concentrated; Stage 2: The particles deform to form a dense closed packing; Stage 3: The fully coalesced particles produce a uniform film (Wicks, Z. W. et al. Organic Coatings: Science and Technology, John Wiley & Sons, Inc., 1992, Vol. I, page 64; Barbour, M. et al. *SITA Technology Limited,* 1996, 1:103). Advantageously, a dry polymer film can be applied directly to the skin as a trans-dermal patch. The percentage of drug within the nanoparticle films can vary, and FIG. 36 shows a proton NMR spectra of various β-lactam nanoparticle films compared to a control poly(ethyl acrylate) polymeric nanoparticle film.

The nanoparticles of the subject invention are also useful as biomedical plastics. Exemplary applications of the nanoparticles include formation into shunts, cannulas, dressings, endotracheal tubes, percutaneous devices, intra-ocular lenses, contact lenses, sutures, screws, patches and any desired other implants that can be made of plastics.

In a specific embodiment, the nanoparticles produced in accordance with the subject invention are sugar-coated. In this embodiment, the polymer backbone comprises a modified sugar polymer. Optionally, the polymer backbone is a copolymer comprised of modified sugar polymer and acrylic or vinyl polymers. Advantageously, the sugar coating enhances the attachment onto the target cell's surface.

Figure 40:
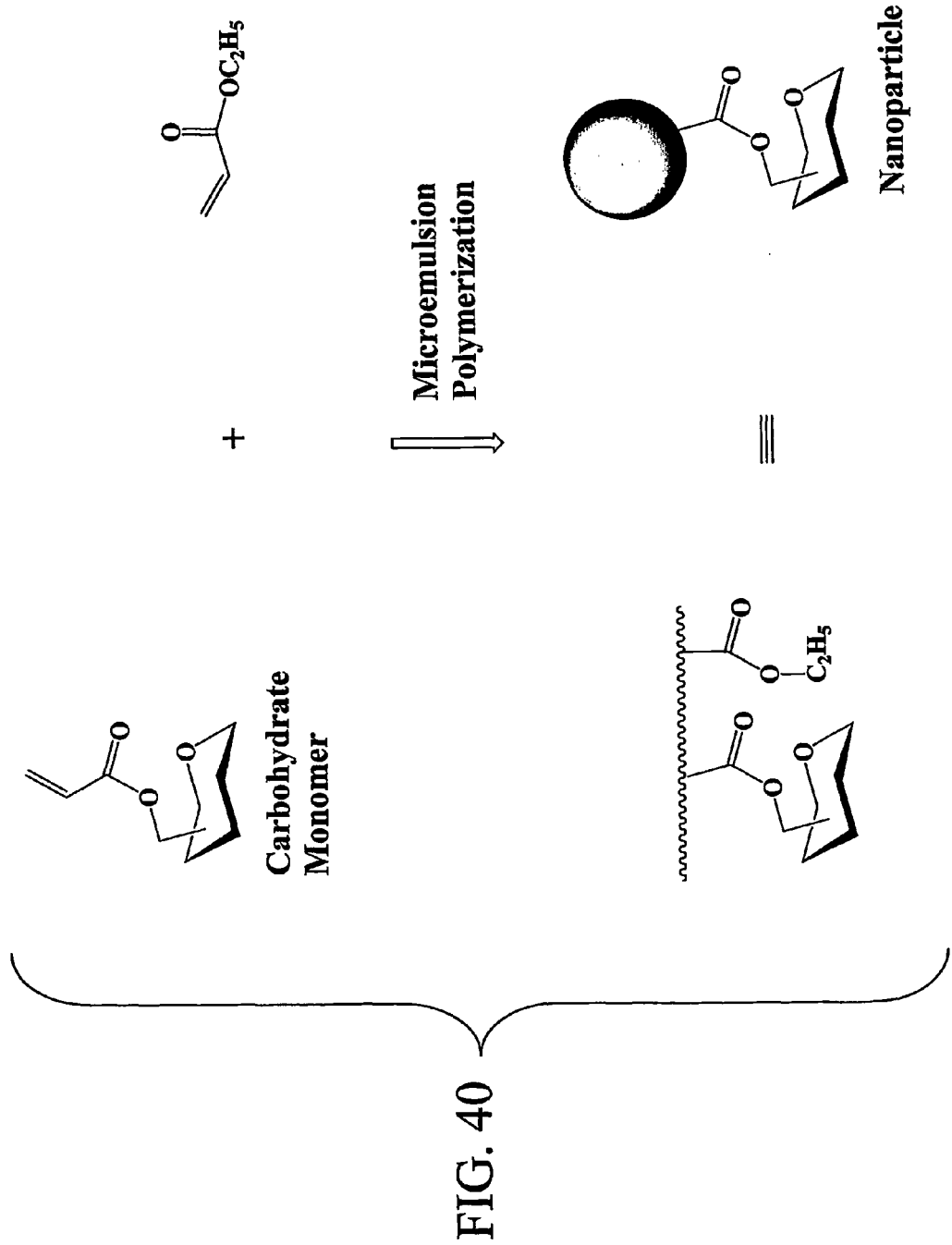
FIG. 40 shows a preparation of sugar-coated nanoparticles.
Figure 41A:
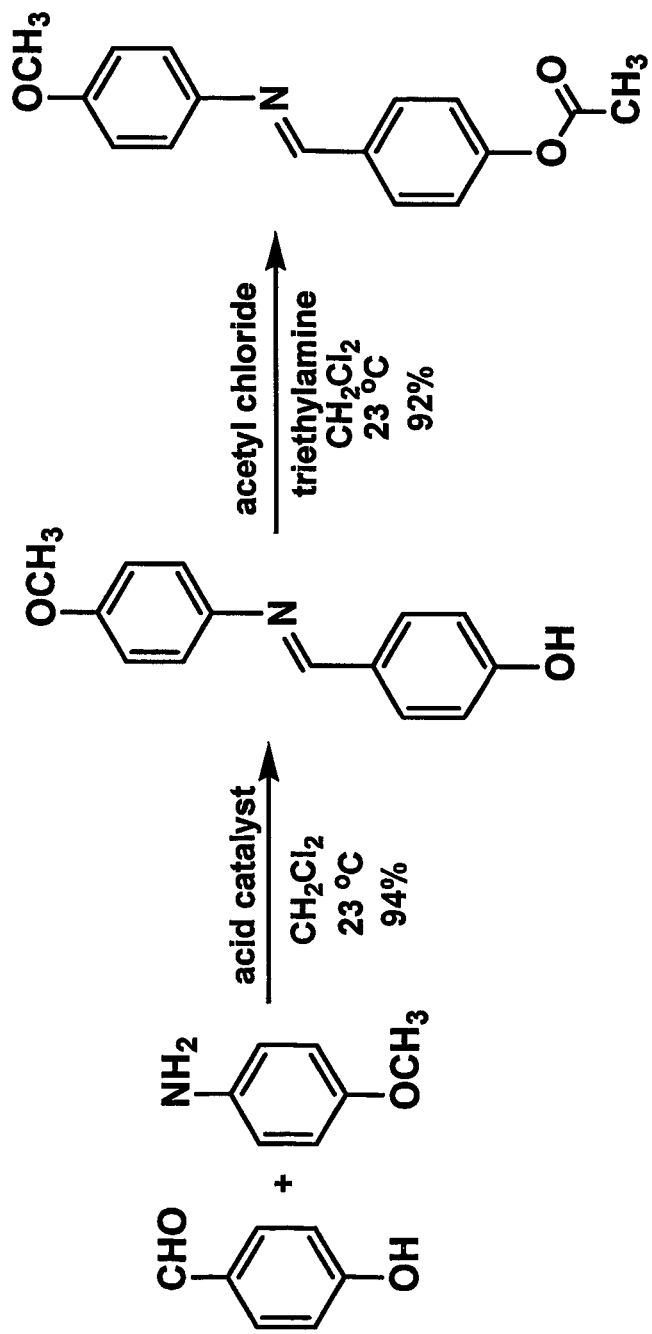
FIG. 41A shows step 1 of the preparation of a $C_4$ β-lactam analog—the synthesis of imine starting material.
Figure 41B:
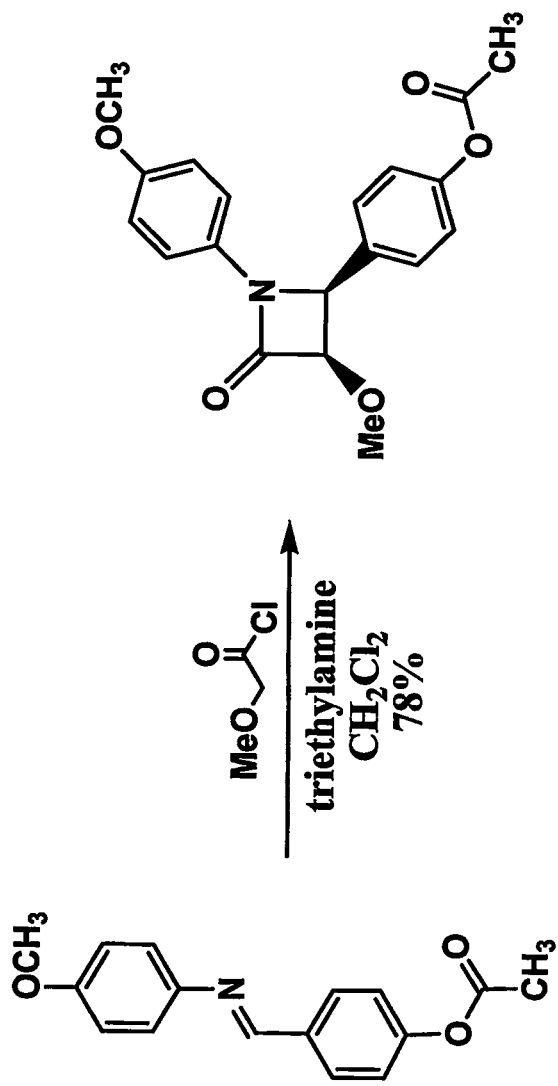
FIG. 41B shows step 2 of the preparation of a $C_4$ β-lactam analog—conversion of imine to β-lactam.
Figure 41C:
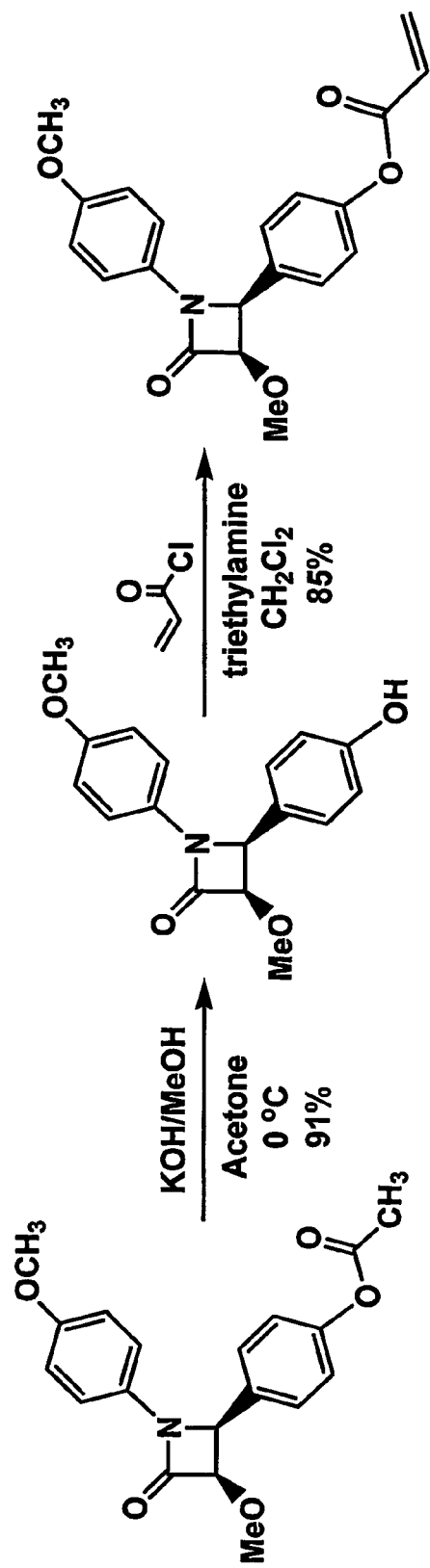
FIG. 41C shows step 3 of the preparation of a $C_4$ β-lactam analog—replacing the acetoxy group for acrylate.
Figure 41D:
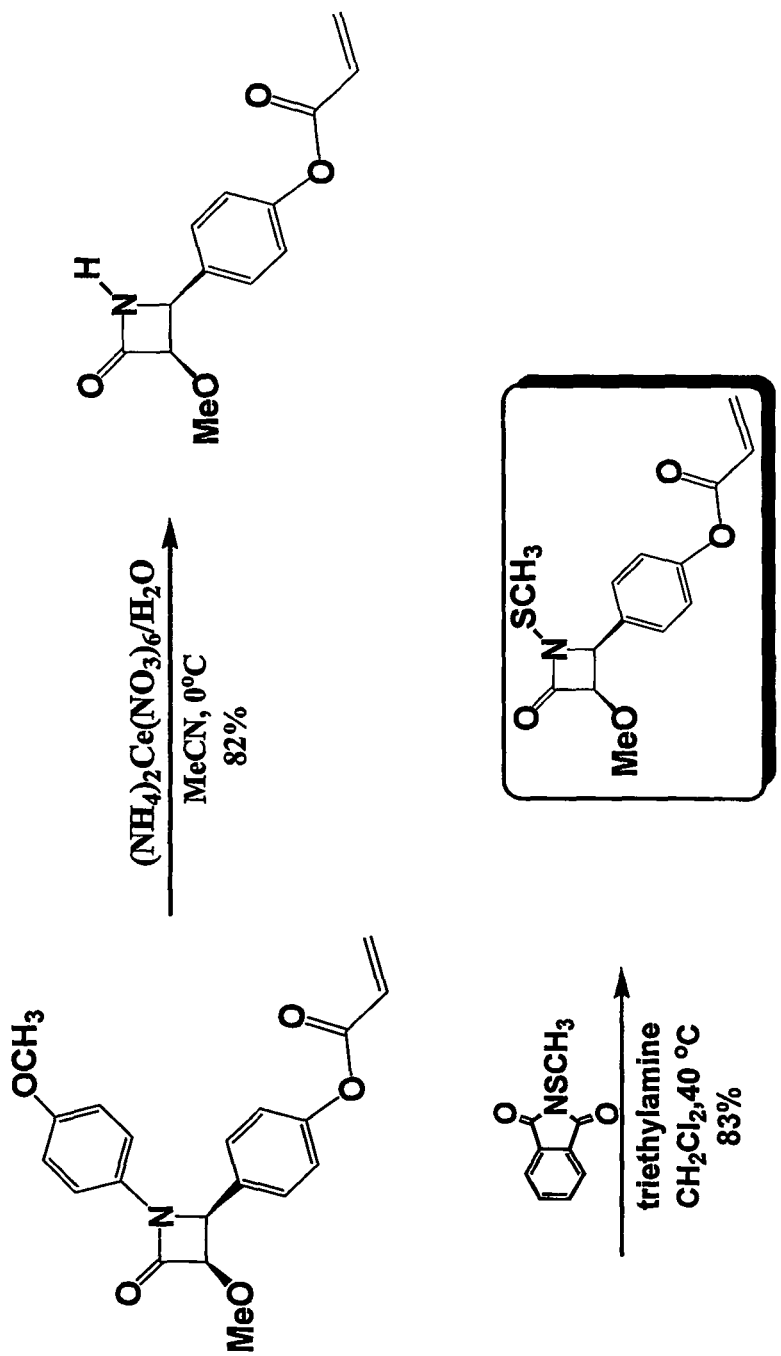
FIG. 41D shows step 4 of the preparation of a $C_4$ β-lactam analog—replacing the N-aryl group for N—$SMe_e$—according to the methods disclosed in *J. Org. Chem.*, 1982, 47:2765 and *Tetrahedron Letters*, 1985, 26:3891.

Advantageously, sugars combine with many proteins and lipids on cell surfaces to control functioning of the immune system, cell-to cell communication and the traffic of mobile cells throughout the body (Scientific American, July 2002). Sugar coated nanoparticles of the subject invention are prepared according to FIG. 40. Briefly, carbohydrates modified with an acrylic substituent are mixed with additional acrylates, for example, ethyl acrylate, and then polymerized according to the microemulsion polymerization process of the subject invention. The resulting nanoparticle is coated with the modified carbohydrate.

Exemplary sugars utilized in accordance with the subject invention include, without limitation, D-glucose (FIG. 24B), α-D-glucopyranose, β-D-glucopyranose, D-fructose, α-D-fructofuranose, D-fructopyranose, D-ribose (FIG. 24A), D-mannose (FIG. 24C), D-galactose (FIG. 24D), D-glucasamine (FIG. 24E), amylase, amylopectin, cellulose, sugar derivatives, for example, sugar alcohols, sugar acids, amino sugars, and sialic acids, maltose, L-sorbose, cellobiose, sucrose, lactose, glycogen, hyaluronate, and lectins.

Figure 22A:
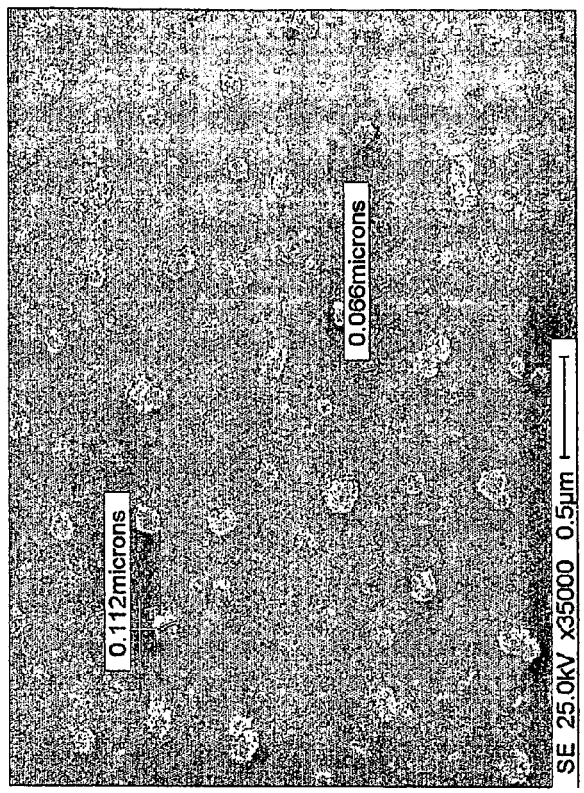
FIGS. 21A, 21B, 22A, 22B.
Figure 22B:
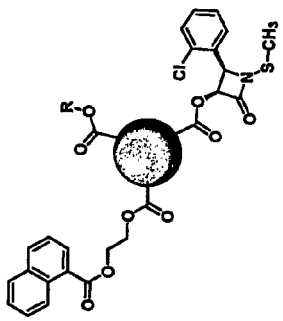
Figure 21A:
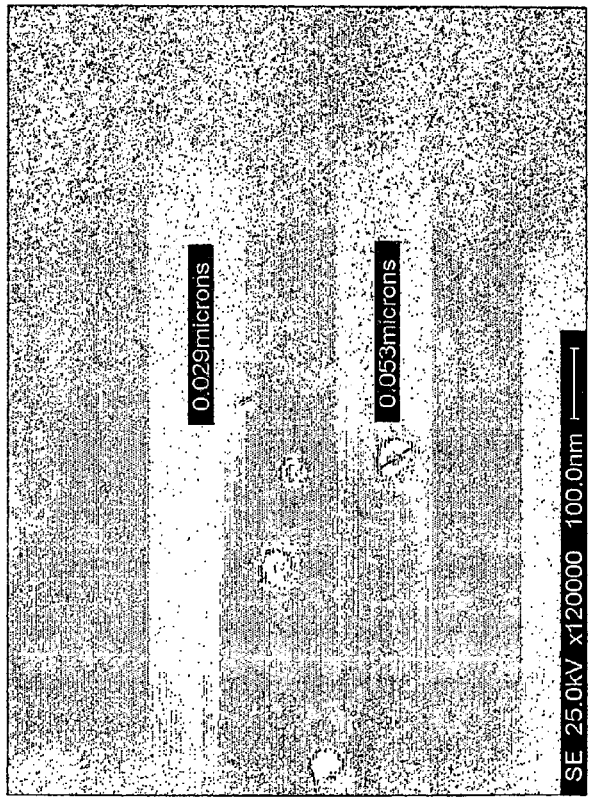
Figure 21B:
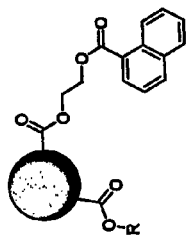
Figure 23B:
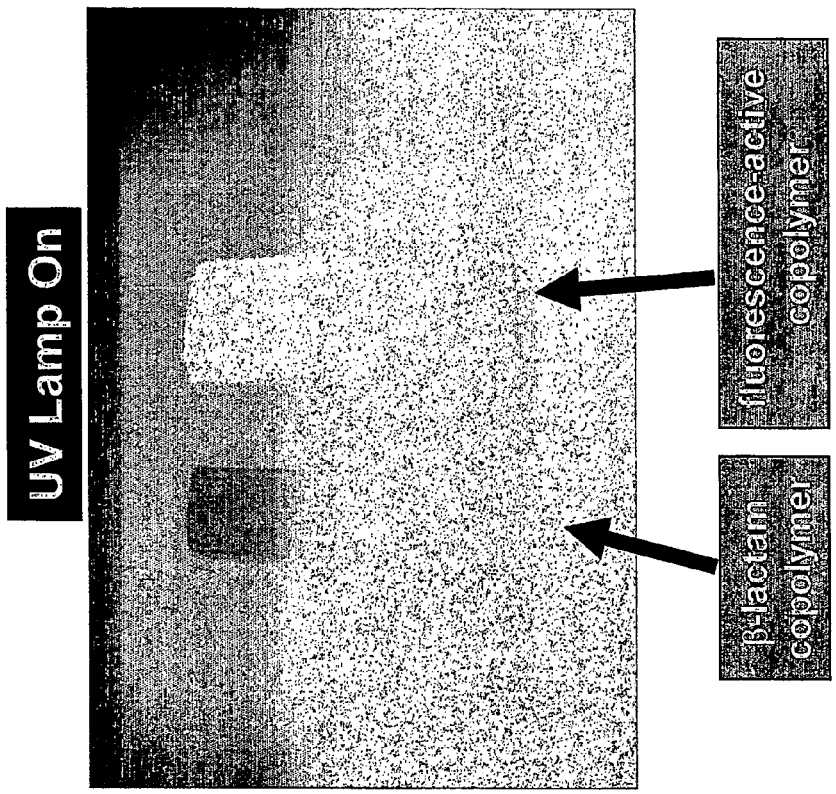
FIGS. 23A and 23B show the fluorescence capabilities of the fluorescent acrylic polymer and β-lactam copolymer with no UV light and in the presence of UV light.
Figure 23A:
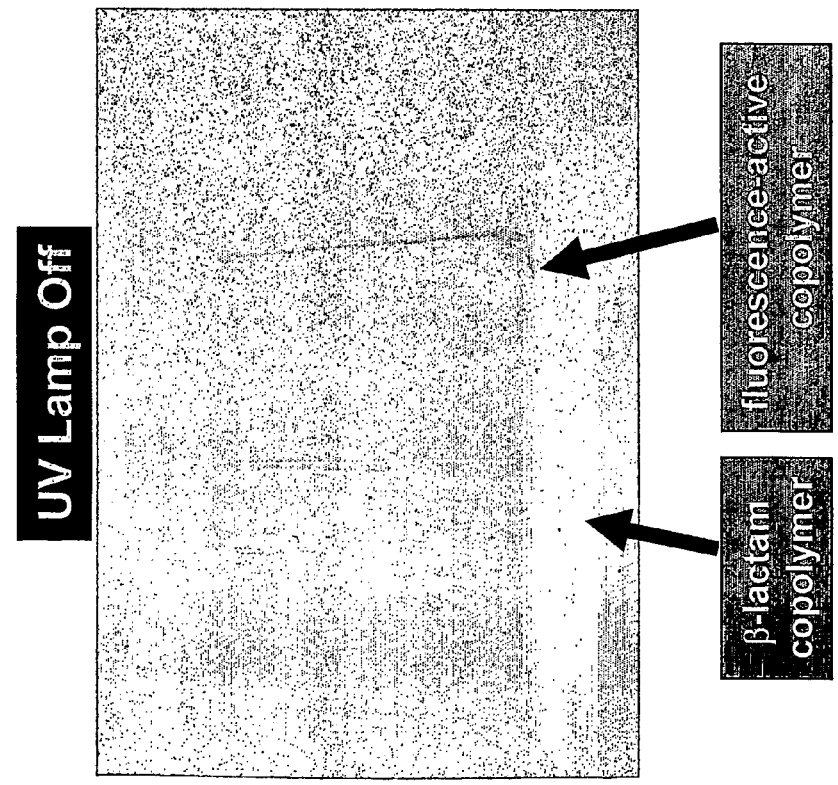
Figure 24B:
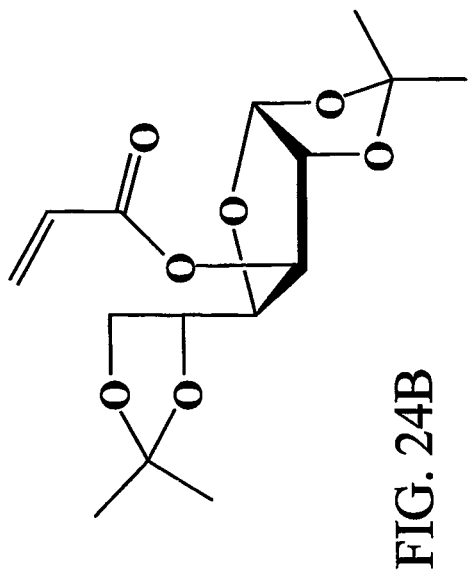
FIG. 24B shows synthetically modified D-glucose.
Figure 24C:
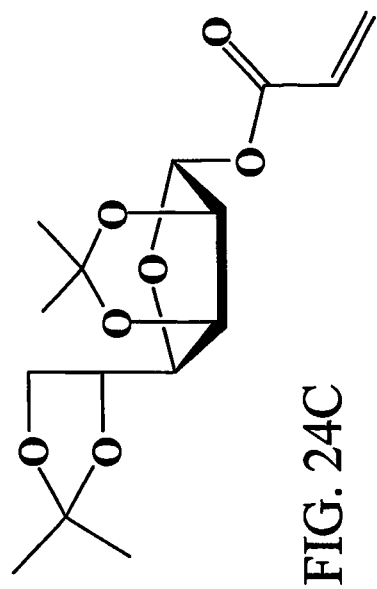
FIG. 24C shows synthetically modified D-mannose.
Figure 24A:
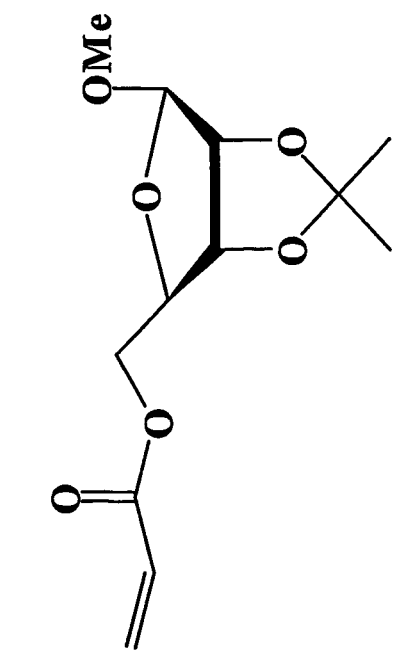
FIG. 24A shows synthetically modified D-ribose.
Figure 24E:
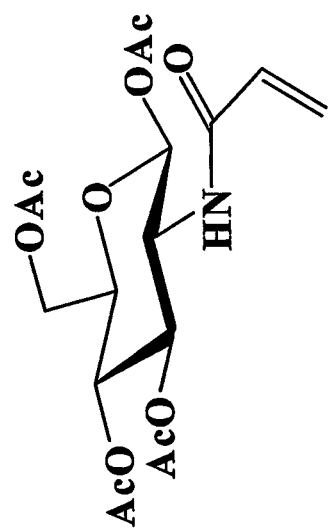
FIG. 24E shows synthetically modified D-glucosamine.
Figure 24D:
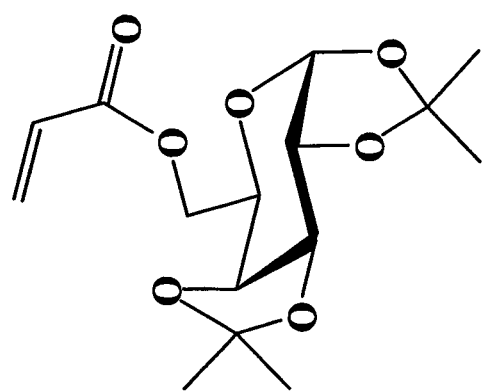
FIG. 24D shows synthetically modified D-galactose.
Figure 52:
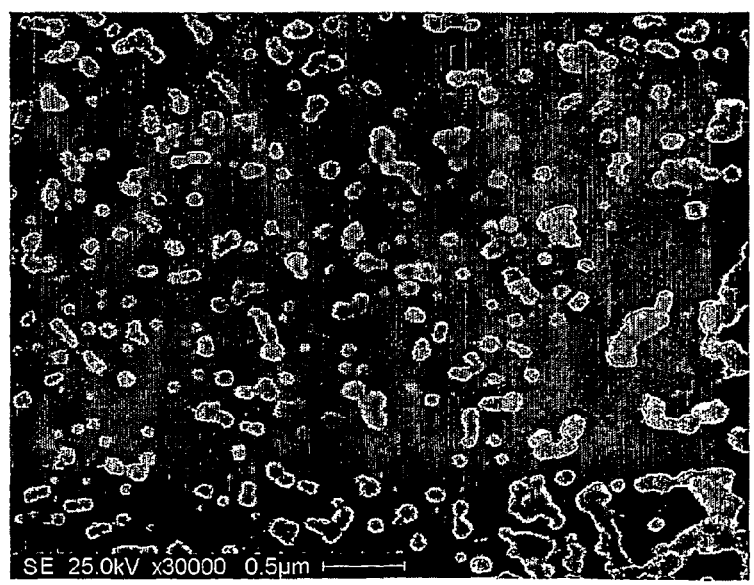
FIG. 52 shows a scanning electron micrograph image for anthracenyl fluorescence-active emulsified nanoparticles with particle size (60-120 nm).
Figure 51:
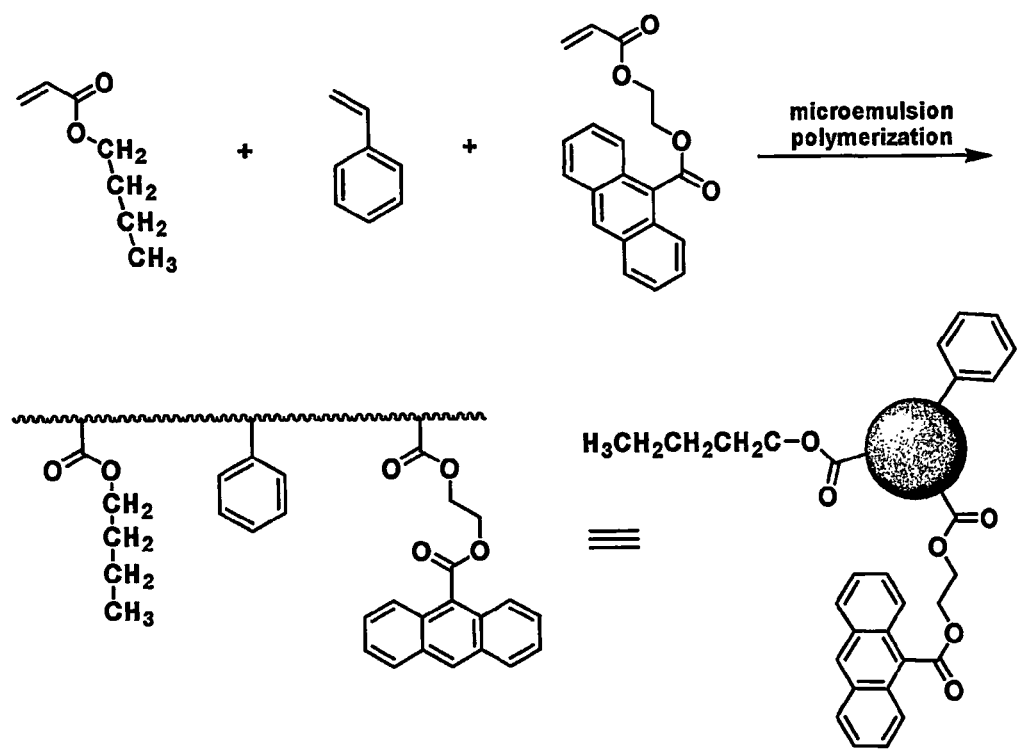
FIG. 51 shows a preparation of fluorescence-active anthracenyl copolymeric nanoparticles.
Figures 53A, 53B:
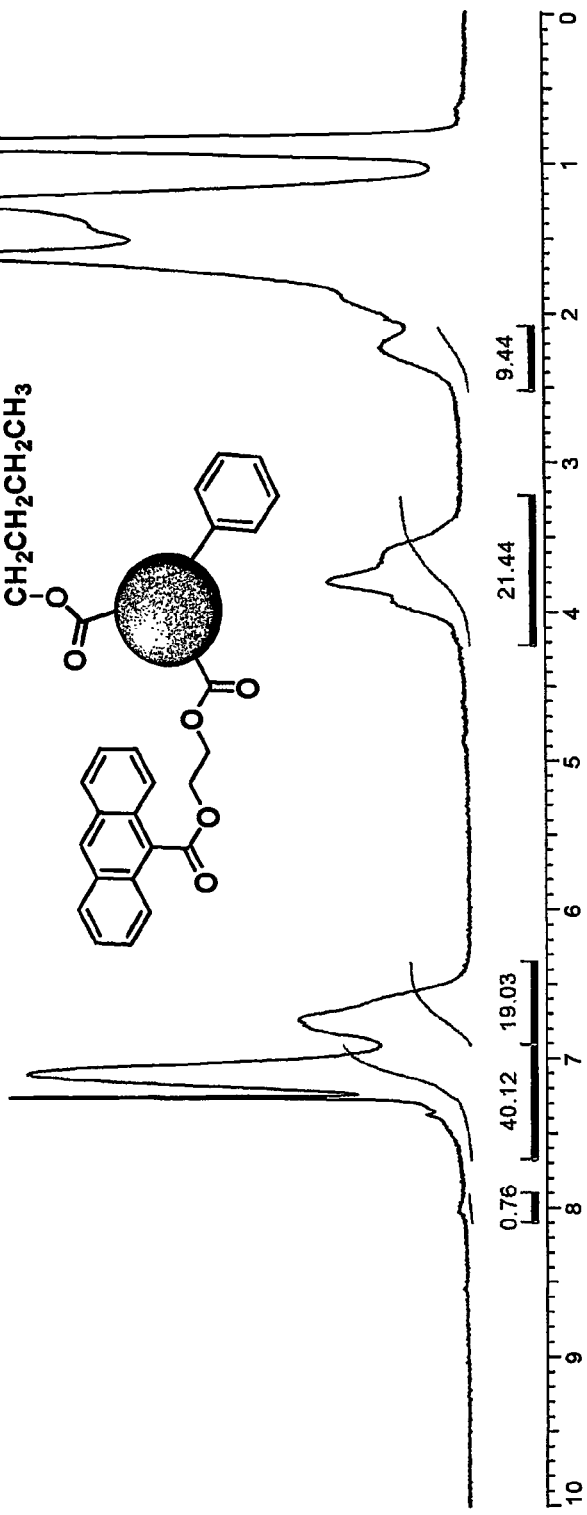
FIGS. 53A and 53B.

In yet another specific embodiment, the polymeric nanoparticles prepared in accordance with the subject invention exhibit fluorescent activity when exposed to ultraviolet light (FIGS. 23A, 23B, 54A, 54B, 54C, and 54D). Fluorescent molecules are acrylated to serve as free radical acceptors in the microemulsion polymerization. Prefered chromophores are lipophillic. More preferably, the molecules include, without limitation, dansyl chloride, 1-naphtholic acid, and 9-anthracene-carboxylic acid. FIGS. 18, 19, 50, and 51 illustrate two preparations of fluorescent active polymer nanoparticles. The $^1$H NMR spectra of the resulting nanoparticles are illustrated in FIGS. 20A, 20C, and 53A. 2-Hydroxy ethyl acrylate is the preferred acrylate since the terminal hydroxyl group is easily coupled with the carboxylic acid group of the fluorescent molecules, and the resultant diester linker is easily hydrolyzed in a biological environment. Advantageously, an acrylated fluorescent monomer and a modified drug monomer can simultaneously undergo microemulsion polymerization to yield a nanoparticle with both fluorescent and antibacterial activities. As shown in FIGS. 21A, 22A, and 52, the duel action nanoparticles are larger than the fluorescent active polymeric nanoparticles.

Advantageously, fluorescence-active polymeric nanoparticles can be applied as a diagnostic tool wherein specific biological molecules are detected by acting as a water-dispersed biological sensor or biological imaging agent.

Furthermore, other biological sensors can be incorporated into the subject nanoparticles to increase the efficiency by which the nanoparticle detects the target cell. In some embodiments, the biosensing polymeric nanoparticle can also send out a signal that allows a health care professional to determine if the target cell is causing illness in the human or animal patient. For example, the polymeric nanoparticles can be incorporated into a biodefense system wherein the nanoparticle detects if a particular disease, for example, anthrax, has been released and then inhaled by a person or animal.

An advantageous feature of the processes of the subject invention is the modification of the bioaffecting agents. The bioaffecting agent contains three components—the agent itself, an acrylic moiety for radical polymerization, and a linker connecting the agent with the acrylic moiety. The bioaffecting agents, preferably drugs, are modified with an addition of a functional group that acts a linker between the bioaffecting agent and the nanoparticle. In a specific embodiment, this process comprises reacting a bioaffecting material with an acrylic or vinyl group. Preferably, the bioaffecting material is a water soluble or insoluble solid or a highly viscous liquid. For example, a liquid that is soluble in organic solutions yet not miscible in aqueous solutions can be modified and utilized in the methods of the subject invention. More preferably, the bioaffecting material is a drug. Most preferably, the drug material is β-lactam, sulindac, penicillin, ciprofloxacin, and their analogs.

Figure 2:
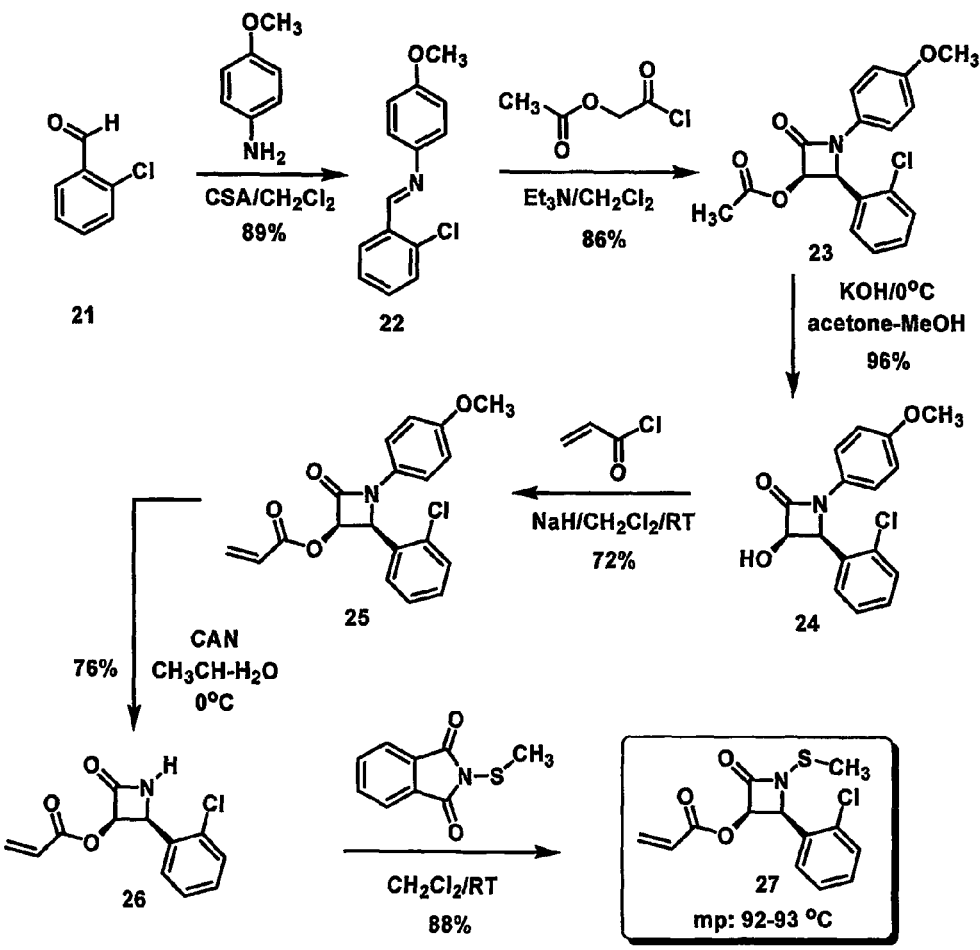
FIG. 2 shows the modification of β-lactam to N-methylthiolated β-lactam.
Figure 14:
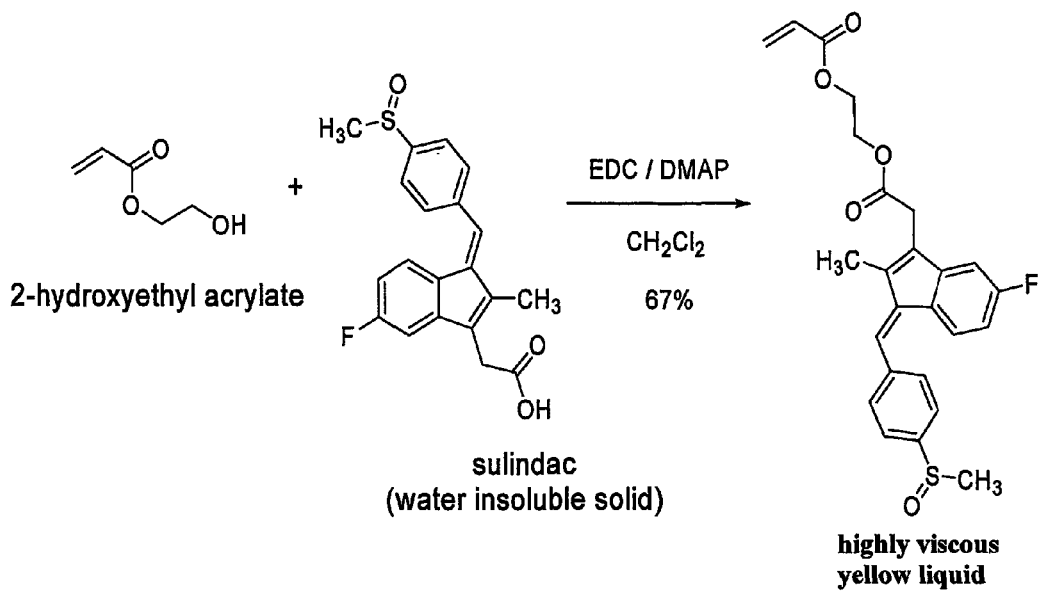
FIG. 14 shows the modification of sulindac to a highly viscous liquid in preparation of microemulsion polymerization.
Figure 15:
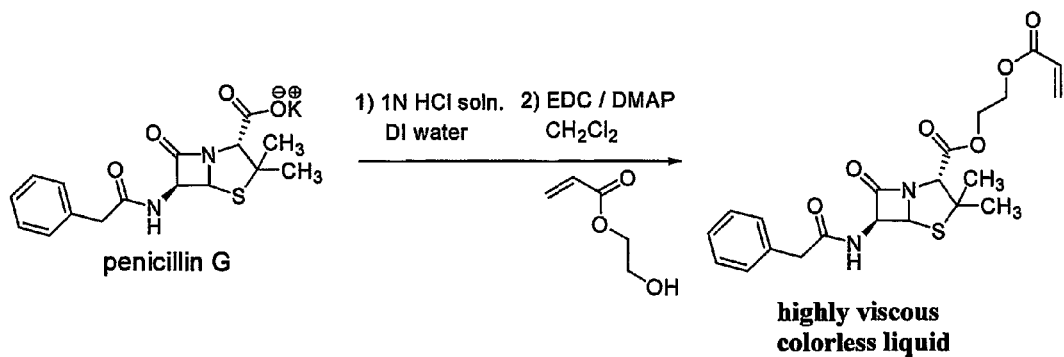
FIG. 15 shows the modification of penicillin G to a highly viscous liquid in preparation for microemulsion polymerization.
Figure 16:
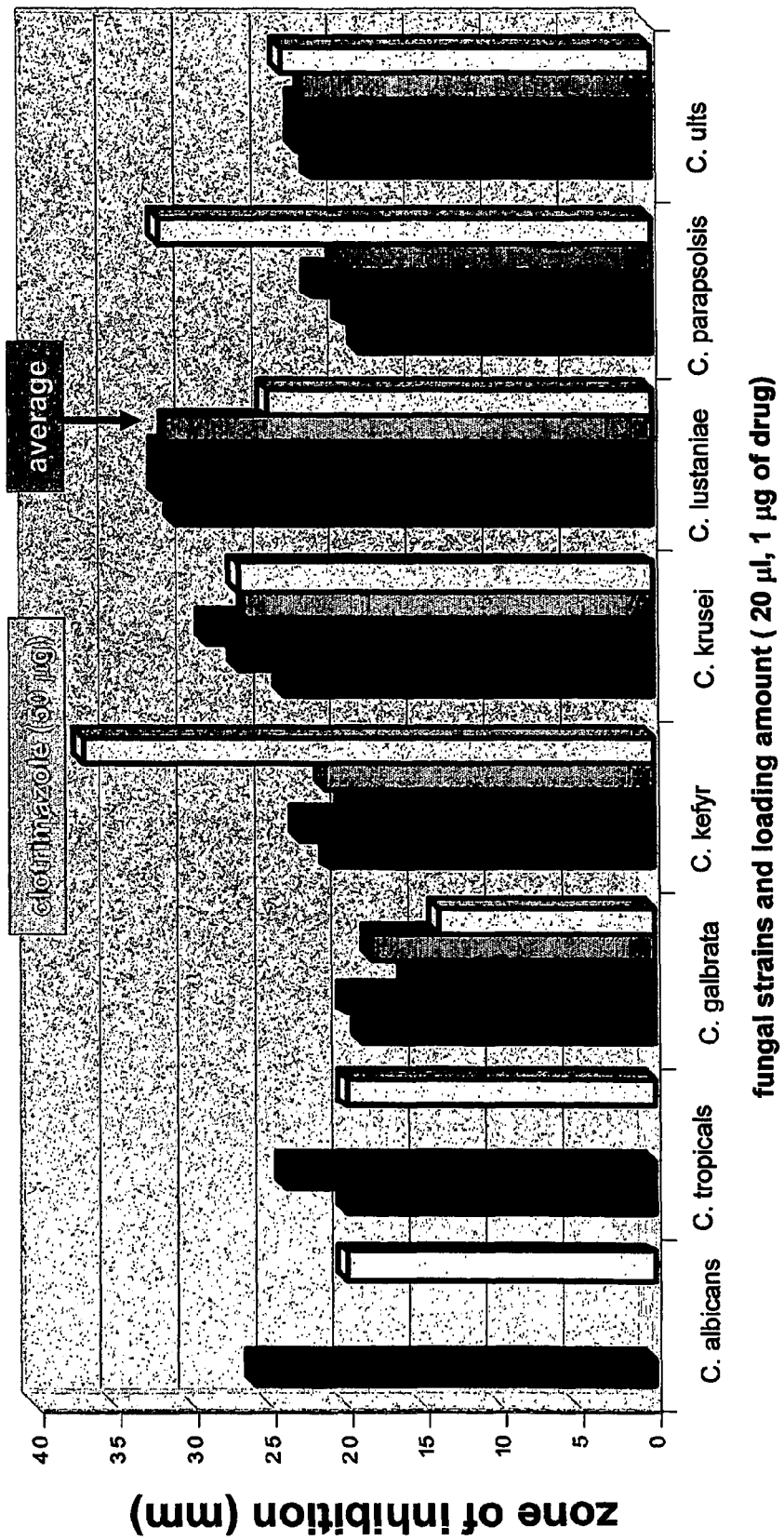
FIG. 16 shows antifungal activity of a β-lactam attached to a polymeric nanoparticle wherein the ratio of β-lactam to co-polymer is 7:1.
Figures 17A, 17B:
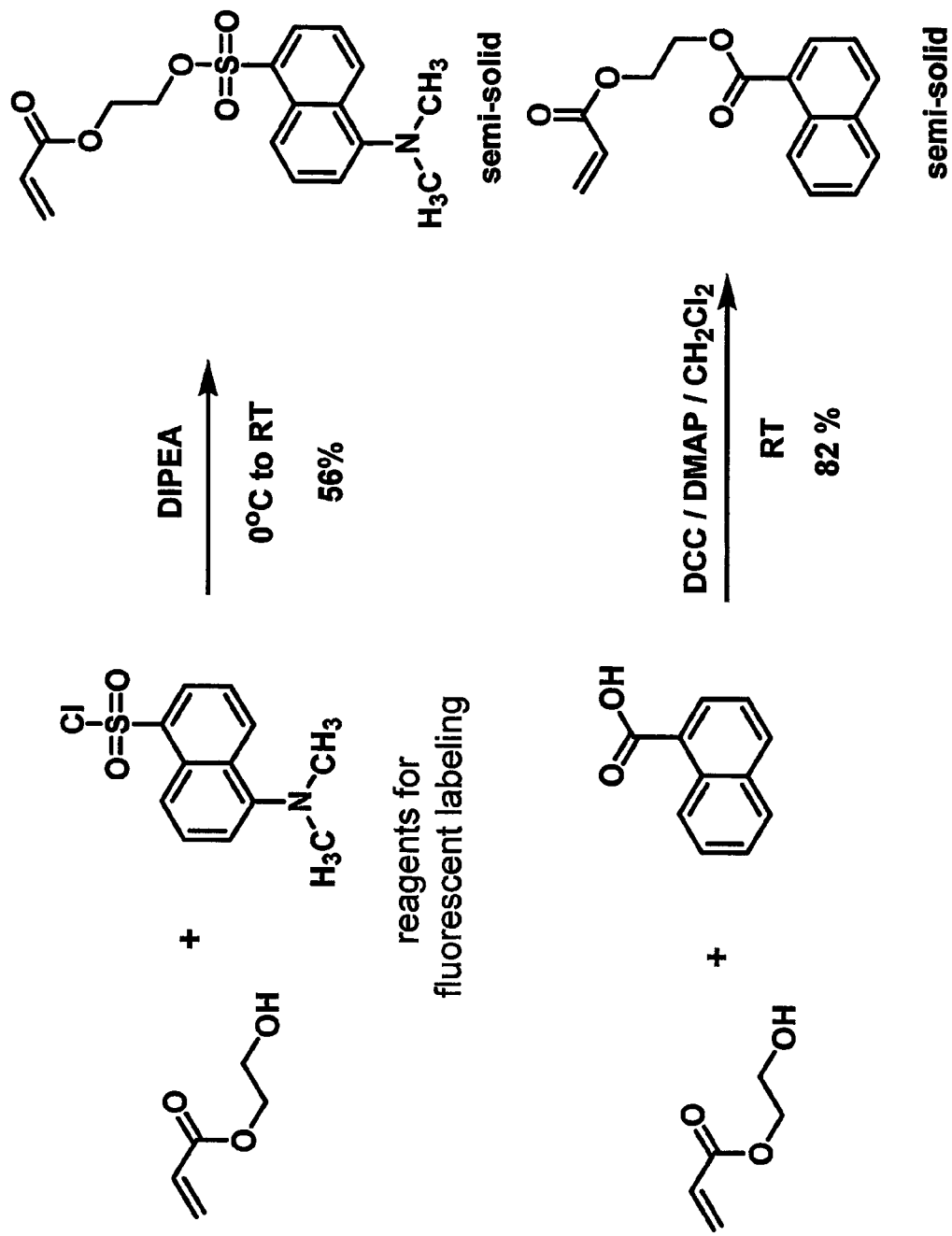
FIG. 17A shows the synthesis of a semi-solid fluorescence-active acrylic monomer.
FIG. 17B shows the synthesis of a semi-solid fluorescence-active acrylic monomer.
Figure 18:
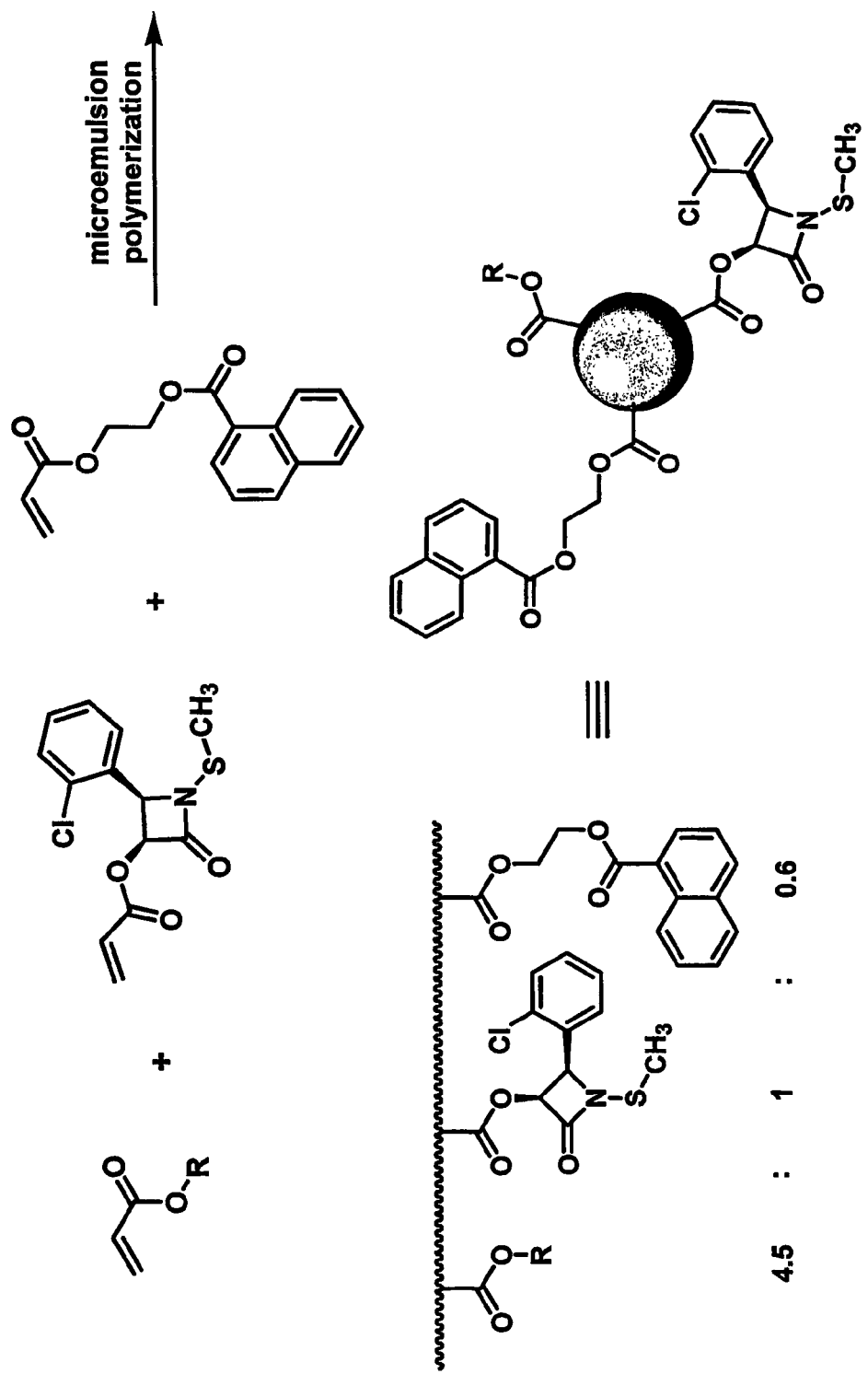
FIG. 18 shows a preparation of a fluorescence-active β-lactam polymeric nanoparticle. The ratio of acrylic monomer to β-lactam to fluorescent monomer in the nanoparticle is 4.5:1:0.6.
Figure 19:
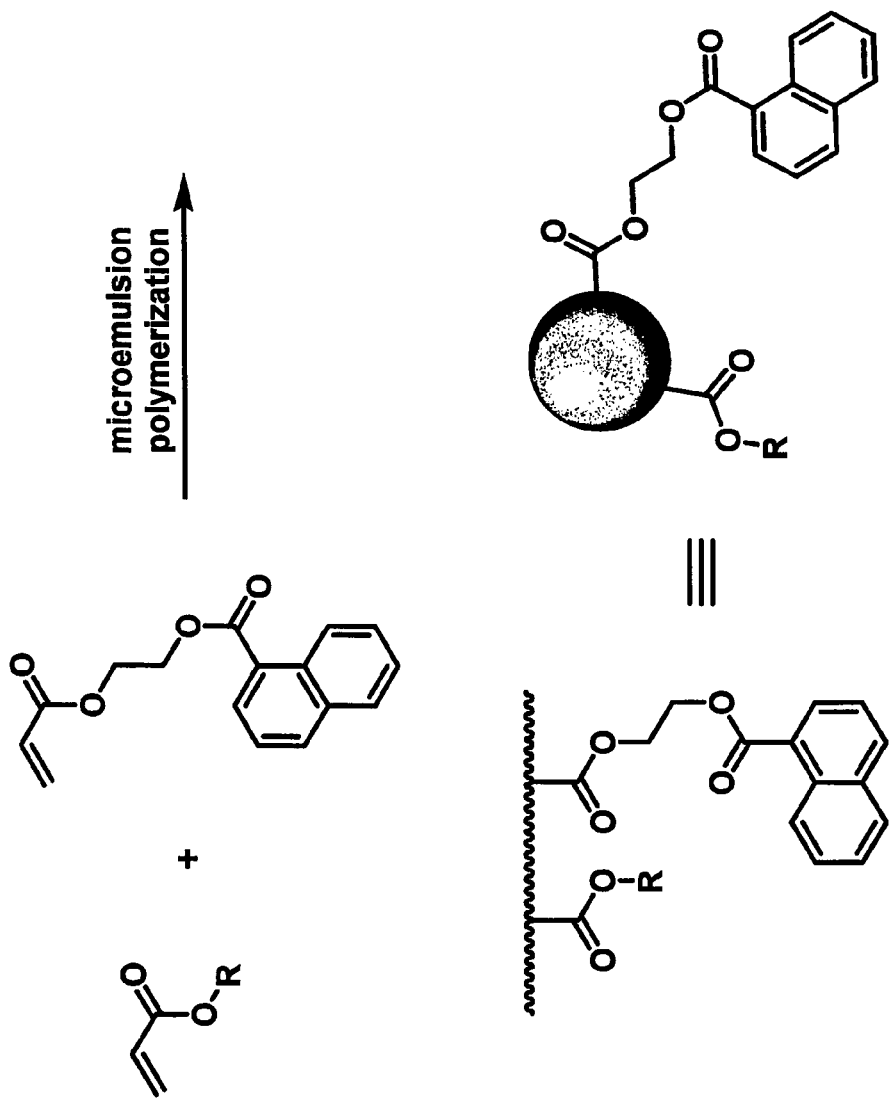
FIG. 19 shows a flow diagram for preparing a fluorescence-active polymeric nanoparticle.

The nanoparticles prepared in accordance with the subject invention contain modified drugs bonded by way of an acrylate linker. FIGS. 2, 14, and 15 illustrate three possible syntheses for modifying drugs in preparation for polymerization according to the subject invention, and Examples 5, 6, and 7 describe three specific modifications to β-lactam. Additionally, Example 13 provides a specific embodiment for the modification of ciprofloxacin.

To introduce the acrylic and linker parts to the drug, the acrylic monomer can be, but is not limited to, acryloyl chloride, methacryloyl chloride, acrylic acid, maleic acid, itaconic acid, crotonic acid, N-methylol acryl amide acrylonitrile, 2-hydroxy ethyl acrylate, 2-hydroxy propyl acrylate, 2-hydroxy ethyl methacrylate, modified acrylamide, modified methacrylamide, (PEG) modified acrylate, and amino acid oligomeric acrylate.

As used herein, it may be preferable that the covalent bond attaching the bioaffecting agent to the nanoparticle is cleaved upon exposure to endogenous or exogenous agents capable of breaking the bond without affecting the morphology of the nanoparticle. Accordingly, specially designed linkers for controlled/biorelease of drugs can be utilized. Examples of such linkers include, but are not limited to, carboxylic esters, carboxamides, carbohydrates or polylactides, which can be hydrolyzed enzymatically or chemically. Thus, polyamino acid (peptide) also can be a linker despite containing a long chain.

In one aspect, the subject invention is directed to a composition of nanoparticles useful for delivering bioaffecting agents to target cells. Preferably, the nanoparticles comprise a drug having good, poor, or little water solubility. The nanoparticle composition comprises a polymer backbone that takes a spherical shape, a bioaffecting agent, and a linker attaching the bioaffecting agent to the backbone via covalent bonds.

Drugs utilized in the nanoparticles include any type of drug including antibacterial, antiviral, antifungal, or anti-cancer agents that can be modified to introduce the acrylic moiety so that they can be polymerized by free radical emulsion polymerization. The drug is a water-insoluble or water-soluble solid or a highly viscous liquid. Advantageously, existing drugs may be synthetically modified when utilized according to the subject invention as shown in FIGS. 2, 14, and 15.

Advantageously, the polymeric nanoparticles are soluble in aqueous media and form a spherical shape. The polymer backbone protects the modified drug by providing enhanced environmental stability and selectivity.

The size of the polymeric nanoparticles is about 1 nm to 1000 nm, and preferably about 1 nm to 400 nm. More preferably, the size is 1 nm to 200 nm. An advantage of the polymeric nanoparticle of the subject invention is its relatively uniform size distribution. The uniform size distribution allows effective drug delivery and stability in blood for a longer period of time so that targeting at specific sites may be facilitated.

Another characteristic of the polymeric nanoparticle is its efficiency in delivering and releasing drugs at the target cell. The covalent bond, polymer backbone, and uniform size distribution prevent loss of the nanoparticles before reaching the target cells and decrease adverse effects and undesirable side reactions. The linker is chosen to break, thereby breaking the covalent bond and releasing the drug, when exposed to agents at the target cell without changing the morphology of the nanoparticle. The agents can be exogeneous or endogeneous to the cell.

A key property of the nanoparticle is the covalent bond between the monomer and the targeted drug. A linker provides the mechanism for the covalent bond. If a biodegradable linker is used to attach the drug to the polymer backbone, it is essential that the linker be able to break down at the target cell, such as when the nanoparticle enters into the target cell. Examples of linkers include, but are not limited to, carboxylic esters, carboxamides, polylactides, and carbohydrates.

A preferred embodiment pertains to a polymeric nanoparticle wherein the drug is a modified methyl-thiolated β-lactam and the monomer is ethyl acrylate.

In yet another specific embodiment, the nanoparticles of the subject invention exhibit fluorescent activity when exposed to ultraviolet light, which is useful for diagnostic, imaging and sensoring.

In yet another specific embodiment, the nanoparticles are cross-linked via bioaffecting agents having at least two linker and acrylic groups.

In a preferred embodiment, nanoparticles of the invention include targeting moieties. As used herein, the terms "targeting moiety" and "targeting agent" are used interchangeably and are intended to mean any agent, such as a functional group, that serves to target or direct the nanoparticle to a particular location or association (e.g., a specific binding event). Thus, for example, a targeting moiety may be used to target a molecule to a specific target protein or enzyme, or to a particular cellular location, or to a particular cell type, to selectively enhance accumulation of the nanoparticle. Suitable targeting moieties include, but are not limited to, polypeptides, nucleic acids, carbohydrates, lipids, hormones including proteinaceous and steroid hormones, growth factors, receptor ligands, antigens and antibodies, and the like. For example, as is more fully outlined below, the nanoparticles of the invention may include a targeting moiety to target the nanoparticles (including bioaffecting agents associated with the nanoparticles) to a specific cell type such as tumor cells, such as a transferrin moiety, since many tumor cells have significant transferrin receptors on their surfaces. Similarly, a targeting moiety may include components useful in targeting the nanoparticles to a particular subcellular location. As will be appreciated by those in the art, the localization of proteins within a cell is a simple method for increasing effective concentration. For example, shuttling a drug into the nucleus confines them to a smaller space thereby increasing concentration. The physiological target may simply be localized to a specific compartment, and the agent must be localized appropriately. More than one targeting moiety can be conjugated or otherwise associated with each nanoparticle, and the target molecule for each targeting moiety can be the same or different.

Thus, suitable targeting sequences include, but are not limited to, binding sequences capable of causing binding of the moiety to a predetermined molecule or class of molecules, while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including (a) subcellular locations such as the Golgi, endoplasmic reticulum, nucleus, nucleoli, nuclear membrane, mitochondria, chloroplast, secretory vesicles, lysosome, and cellular membrane; and (b) extracellular locations via a secretory signal. Particularly preferred is localization to either subcellular locations.

The targeting moiety can function to target or direct the nanoparticle to a particular location, cell type, diseased tissue, or association. In general, the targeting moiety is directed against a target molecule. As will be appreciated by those in the art, the nanoparticles of the invention are can be applied locally or systemically administered (e.g., injected intravenously); thus, preferred targeting moieties are those that allow concentration of the bioaffecting agents in a particular localization. Thus, for example, antibodies, cell surface receptor ligands and hormones, lipids, sugars and dextrans, alcohols, bile acids, fatty acids, amino acids, peptides and nucleic acids may all be attached to localize or target the nanoparticles to a particular site.

In preferred embodiments, the targeting moiety allows targeting of the nanoparticles of the invention to a particular tissue or the surface of a cell. That is, in some embodiments, the nanoparticles of the invention need not be taken up into the cytoplasm of a cell to be activated.

In some embodiments, the targeting moiety is a peptide. For example, chemotactic peptides have been used target tissue injury and inflammation, particularly by bacterial infection; see WO 97/14443, which is incorporated herein by reference in its entirety.

In some embodiments, the targeting moiety is an antibody. The term "antibody" includes antibody fragments, as are known in the art, including Fab or $Fab_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some PR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boemer et al. are also available for the preparation of human monoclonal antibodies (Cole et al., *Monoclonal Antibodies and Cancer Therapy*, Alan R. Liss, p. 77

(1985) and Boerner et al., *J. Immunol.* 147(1):86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology*, 14:826 (1996); Lonberg and Huszar, *Intern. Rev. Immunol.* 13:65-93 (1995).

Bispecific antibodies are monoclonal, preferably human or humanized, antibodies that have binding specificities for at least two different antigens. In the present case, one of the binding specificities is for a first target molecule and the other one is for a second target molecule.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism (see, for example, Suresh et al., *Methods in Enzymology* 121:210 (1986)).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells, including, but not limited to, HER2, VEGF, etc.

In addition, antibodies against physiologically relevant carbohydrates may be used, including, but not limited to, antibodies against markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In one embodiment, antibodies against virus or bacteria can be used as targeting moieties. As will be appreciated by those in the art, antibodies to any number of viruses (including orthomyxoviruses, (e.g., influenza virus), paramyxoviruses (e.g. respiratory syncytial virus, mumps virus, measles virus), adenoviruses, rhinoviruses, coronaviruses, reoviruses, togaviruses (e.g., rubella virus), parvoviruses, poxyiruses (e.g., variola virus, vaccinia virus), enteroviruses (e.g., poliovirus, coxsackievirus), hepatitis viruses (including A, B and C), herpesviruses (e.g., Herpes simplex virus, varicella-zoster virus, cytomegalovirus, Epstein-Barr virus), rotaviruses, Norwalk viruses, hantavirus, arenavirus, rhabdovirus (e.g., rabies virus), retroviruses (including HIV, HTLV-I and -II), papovaviruses (e.g., papillomavirus), polyomaviruses, and picornaviruses, and the like), and bacteria (including a wide variety of pathogenic and non-pathogenic prokaryotes of interest including *Bacillus; Vibrio*, e.g., *V. cholerae; Escherichia*, e.g. Enterotoxigenic *E. coli*, *Shigella*, e.g., *S. dysenteriae*; *Salmonella*, e.g., *S. typhi*; *Mycobacterium* e.g., *M. tuberculosis, M. leprae; Clostridium*, e.g., *C. botulinum, C. tetani, C. difficile, C. peffringens; Comyebacterium*, e.g., *C. diphtheriae; Streptococcus, S. pyogenes, S. pneumoniae; Staphylococcus*, e.g., *S. aureus; Haemophilus*, e.g., *H. influenzae; Neisseria*, e.g., *N. meningitidis, N. gonorrhoeae; Yersinia*, e.g., *G. lamblia Y. pestis, Pseudomonas*, e.g., *P. aeruginosa, P. putida; Chlamydia*, e.g., *C. trachomatis; Bordetella*, e.g., *B. pertussis; Treponema*, e.g., *T. palladium*; and the like) may be used.

In a preferred embodiment, the targeting moiety is all or a portion (e.g., a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-.alpha. and TGF-.beta.), EPO receptor (EPO), ThO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryoid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In another embodiment, the targeting moiety is a carbohydrate. As used herein, the term "carbohydrate" includes compounds with the general formula $Cx(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates.

In another embodiment, the targeting moiety is a lipid. As used herein, the term "lipid" includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moiety may be used to either allow the internalization of the nanoparticle to the cell cytoplasm or localize it to a particular cellular compartment, such as the nucleus. In another embodiment, the targeting moiety is all or a portion of the HIV-1 Tat protein, and analogs and related proteins, which allows very high uptake into target cells (See for example, Fawell et al., *PNAS USA* 91:664 (1994); Frankel et al., *Cell* 55:1189 (1988); Savion et al., *J. Biol. Chem.* 256:1149 (1981); Derossi et al., *J. Biol. Chem.* 269:10444 (1994); and Baldin et al., *EMBO J.* 9:1511 (1990), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499-509; the human retinoic acid receptor-.beta. nuclear localization signal (ARRRRP); NFκB p50 (EEVQRKRQKL; Ghosh et al., *Cell* 62:1019 (1990); NFκ B p65 (EEKRKRTYE; Nolan et al., Cell 64:961 (1991); and others (see for example Boulikas, *J. Cell. Biochem.* 55(1):32-58 (1994), hereby incorporated by reference) and double basic NLSs exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449-458, 1982 and Dingwall, et al., *J. Cell Biol.,* 107:641-849; 1988). Numerous localization studies have demonstrated that NLSs incorporated in synthetic peptides or grafted onto reporter proteins not normally targeted to the cell nucleus cause these peptides and reporter proteins to be concentrated in the nucleus (see, for example, Dingwall, and Laskey, *Ann, Rev. Cell Biol.,* 2:367-390, 1986; Bonnerot, et al., *Proc. Natl. Acad. Sci. USA,* 84:6795-6799, 1987; Galileo, et al., *Proc. Natl. Acad. Sci. USA,* 87:458-462, 1990.

In another embodiment, targeting moieties for the hepatobiliary system are used (see U.S. Pat. Nos. 5,573,752 and 5,582,814, both of which are hereby incorporated by reference in their entirety).

In specific embodiments, a cell-binding agent is utilized as the targeting moiety. Selection of the appropriate cell-binding agent is a matter of choice that depends upon the particular cell population to be targeted, but in general monoclonal antibodies are preferred if an appropriate one is available.

The nanoparticles of the present invention can be used to deliver a bioaffecting agent that is cytotoxic to cancer cells. For example, the monoclonal antibody MY9 is a murine IgG$_1$ antibody that binds specifically to the CD33 antigen (J. D. Griffin et al. *Leukemia Res.,* 8: 521 (1984)) which can be used if the target cells express CD33, such as in the disease of acute myelogenous leukemia (AML). Similarly, the monoclonal antibody anti-B4 is a murine IgG$_1$ that binds to the CD19 antigen on B cells (Nadler et al., *J. Immunol.* 131: 244-250 (1983)) and can be used if the target cells are B cells or diseased cells that express this antigen, such as in non-Hodgkin's lymphoma or chronic lymphoblastic leukemia. Similarly, the antibody N901 is a murine monoclonal IgG$_1$ antibody that binds to CD56 found on small cell lung carcinoma cells and on cells of other tumors of neuroendocrine origin (Roy et al. *J. Nat. Cancer Inst.* 88:1136-1145 (1996)).

Antibodies that target solid tumors are also useful, such as the C242 antibody which binds to a carbohydrate antigen found on MUC1 present on pancreatic and colorectal tumors. (U.S. Pat. No. 5,552,293); antibody J591, which binds to PSMA (prostate specific membrane antigen) which is expressed on prostate cancer cells and on endothelial cells of neovasculature in tumors (U.S. Pat. No. 6,107,090, He Liu et al. Cancer Res. 57: 3629-3634 (1997); and antibodies to HER-2, which is overexpressed on certain breast tumors. Examples of anti-HER-2 antibodies are the TA1 antibody (L. A. Maier et al *Cancer Res.* 51: 5361-5369 (1991)) and the 4D5 antibody (U.S. Pat. Nos. 6,387,371 and 6,399,063).

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes can be used for the treatment of melanoma. Folic acid, which targets the folate receptor expressed on ovarian and other cancers, is also a suitable cell-binding agent.

Cancers of the breast and testes can be successfully targeted with estrogen (or estrogen analogues) or androgen (or androgen analogues), respectively, as cell-binding agents.

The subject invention includes pharmaceutical compositions comprising polymeric nanoparticles associated with one or more bioaffecting agents, within a pharmaceutically acceptable carrier. The pharmaceutical compositions of the subject invention can be formulated according to known methods for preparing pharmaceutically useful compositions. The carrier may be liquid, solid, or semi-solid, for example. Formulations are described in a number of sources which are well known and readily available to those skilled in the art. For example, *Remington's Pharmaceutical Sciences* (Martin E W, 1995, Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents.

The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Administration of the nanoparticles of the subject invention to a biosystem, such as human or non-human animal subject can be achieved by conventional procedures known by those of ordinary skill in the art and disclosed in the literature. Aqueous solutions of nanoparticles are most conveniently used. Administration may be achieved by any route or method. For example, the nanoparticles (and compositions comprising the nanoparticles) can be administered parentally, such as by intravenous administration. One of skill in the art can readily determine appropriate dosages, concentrations, and rates and duration of administration, based on the size of the subject and the route of administration.

In yet another aspect, the subject invention is directed to methods for the administration of polymeric drug nanoparticles, which are prepared in accordance with the subject invention, to a human or non-human animal cell in a pharmaceutically effective amount. The methods of administration further comprise providing a polymeric drug nanoparticle prepared in accordance with the subject invention and contacting a target cell with an effective amount of the polymeric drug nanoparticle. In one specific embodiment, the polymeric nanoparticles are administered within a pharmaceutically acceptable carrier.

Methods of administration include, but are not limited to, intra-arterial, intramuscular, intravenous, intranasal, and oral routes. In a specific embodiment, the pharmaceutical compositions of the invention can be administered locally to the area in need of treatment; such local administration can be achieved, for example, by local infusion during surgery, by injection, or by means of a catheter.

Therapeutic amounts can be empirically determined and will vary with the pathology being treated, the subject being treated, and the efficacy and toxicity of the modified bioaffecting agent. Similarly, suitable dosage formulations and methods of administering the bioaffecting agents can be readily determined by those of skill in the art.

The polymeric drug nanoparticles can be administered by any of a variety of routes, such as orally, intranasally, parenterally or by inhalation therapy, and can take form of tablets, lozenges, granules, capsules, pills, ampoule, suppositories or aerosol form. They can also take the form of suspensions, solutions, and emulsions of the active ingredient in aqueous or nonaqueous diluents, syrups, granulates or powders. In addition to an agent of the present invention, the polymeric drug nanoparticles can also contain other pharmaceutically active compounds or a plurality of compounds of the invention.

The invention encompasses co-administration steps, with co-administration amounts, or with both the steps and the amounts together, which provide the desired pharmaceutical effect. Advantages of such co-administration can include improvement in the side-effect profiles of one or more of the co-administered agents.

Advantageously, the polymeric drug nanoparticles can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

In another embodiment, the nanoparticles of the invention can be associated with an implantable or deployable medical device. Optionally, the device may release the nanoparticles in a controlled fashion.

The practice of the subject invention can employ, unless otherwise indicated, conventional techniques of molecular biology, microbiology, recombinant DNA technology, electrophysiology, and pharmacology, that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

The following definitions are used, unless otherwise described.

As used herein, the term "drug" is interchangeable with the term "bioaffecting agent" or "biologically active agent" and refers to any agent capable of having a physiologic effect (e.g., a therapeutic or prophylactic effect) on a biosystem such as prokaryotic or eukaryotic cells, in vivo or in vitro, including, but without limitation, chemotherapeutics, toxins, radiotherapeutics, radiosensitizing agents, gene therapy vectors, antisense nucleic acid constructs, transcription factor decoys, imaging agents, diagnostic agents, agents known to interact with an intracellular protein, polypeptides, and polynucleotides. Drugs that may be utilized in the nanoparticles include any type of compound including antibacterial, antiviral, antifungal, or anti-cancer agents that can be modified to attach a polymerizable monomer moiety. Preferably, the polymerizable moiety is an acrylic. The drug is preferably a water-insoluble or water-soluble solid or a highly viscous liquid.

The drug can be selected from a variety of known classes of drugs, including, for example, analgesics, anesthetics, anti-inflammatory agents, anthelmintics, anti-arrhythmic agents, antiasthma agents, antibiotics (including penicillins), anti-cancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radiopharmaceuticals, hormones, sex hormones (including steroids), time release binders, anti-allergic agents, stimulants and anoretics, steroids, sympathomimetics, thyroid agents, vaccines, vasodilators, and xanthines.

The bioaffecting agent need not be a therapeutic agent. For example, the agent may be cytotoxic to the local cells to which it is delivered but have an overall beneficial effect on the subject. Further, the bioaffecting agent may be a diagnostic agent with no direct therapeutic activity per se, such as a contrast agent for bioimaging.

A description of these classes of drugs and diagnostic agents and a listing of species within each class can be found, for instance, in Martindale, The Extra Pharmacopoeia, Twenty-ninth Edition (The Pharmaceutical Press, London, 1989), which is incorporated herein by reference in its entirety. The drugs or diagnostic agents are commercially available and/or can be prepared by techniques known in the art.

Poorly water soluble drugs which may be suitably used in the practice of the subject invention include but are not limited to alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, fiunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenytoin, piroxicam, quinapril, ramipril, risperidone, sertraline, simvastatin, sulindac, terbinafine, terfenadine, triamcinolone, valproic acid, zolpidem, or pharmaceutically acceptable salts of any of the above-mentioned drugs.

As used in this specification, including the appended claims, the singular "a", "an", and "the" include plural reference unless the contact dictates otherwise. Thus, for example, a reference to "a nanoparticle" includes more than one such nanoparticle. A reference to "a bioaffecting agent" includes more than one such agent. A reference to "a cell" includes more than one such cell. A reference to "a targeting agent" includes more than one such targeting agent.

The terms "comprising", "consisting of" and "consisting essentially of" are defined according to their standard meaning. The terms may be substituted for one another throughout the instant application in order to attach the specific meaning associated with each term.

"Alkyl," "alkoxy," etc. denote both straight and branched groups; but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. "Heteroalkyl" encompasses the replacement of a carbon atom within an allyl chain with a heteroatom; e.g., replacement with an element other than carbon such as N, S, or O, including both an alkyl interrupted by a heteroatom as well as an alkyl substituted by a heteroatom.

Specific and preferred values listed below for radicals, substituents, and ranges, are for illustration only; they do not exclude other defined values or other values within defined ranges for the radicals and substituents.

Specifically, "alkyl" can include methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl.

"Alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradeceny, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl.

"Alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl.

"Aryl" can include phenyl, indenyl, 5,6,7,8-tetrahydronaphthyl, or naphthyl. "Heteroaryl" can include furyl, imidazolyl, tetrazolyl, pyridyl, (or its N-oxide), thienyl, pyrimidinyl (or its N-oxide), indolyl, or quinolyl (or its N-oxide).

The terms "biosystem", "host", "host biosystem", "patient", "recipient", and "subject", are used interchangeably and, for the purposes of the present invention, include both prokaryotic and eukaryotic cells, such as human cells and non-human animal cells (e.g., mammal cells). Nanoparticles of the subject invention may be administered to such cells in vitro or in vivo. Thus, the methods of administration are applicable to both human therapy and veterinary applications, as well as research applications in vitro or within animal models.

As used herein, an "effective amount" of nanoparticles or bioaffecting agent is that amount effective to bring about the physiological changed desired in the biosystem to which the nanoparticles are administered. The term "therapeutically effective amount" as used herein, means that amount of nanoparticles or bioaffecting agent, alone or in combination with another agent according to the particular aspect of the invention, that elicits the biological or medicinal response in a biosystem that is being sought by a researcher, veterinarian, medical doctor or other clinician, which includes alleviation of the symptoms of the disease or disorder being treated.

For example, if the bioaffecting agent is a therapeutic agent, an effective amount of the nanoparticles of bioaffecting agent is that amount sufficient to treat a pathological condition (e.g., a disease or other disorder) in the biosystem to which the nanoparticles are administered. For example, in the case of cancer, the therapeutically effective amount of the bioaffecting agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "linked", "joined", "grafted", "tethered", "associated", and "conjugated" in the context of the nanoparticles of the invention, are used interchangeably to refer to any method known in the art for functionally connecting moieties (such as targeting moieties), including, without limitation, recombinant fusion, covalent bonding, disulfide bonding, ionic bonding, hydrogen bonding, and electrostatic bonding.

The term "milky" refers to a cloudy, homogeneous solution. A milky solution is not translucent; however, light is refracted through the solution when a sample of it is held at different angles to a light. As used in the subject application, the solution is permanently cloudy and homogeneous and does not settle or separate. The consistency of a milky solution can change as the morphology of a nanoparticle in the solution changes.

The term "modified" refers to an alteration from an entity's normally occurring state. An entity can be modified by removing discrete chemical units or by adding discrete chemical units.

The term "polypeptides" refers to any polymer comprising any number of amino acids, and is interchangeable with "protein", "gene product", and "peptide".

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

FIG. 2 illustrates a preparation of a modified β-lactam drug. The final product in this example is the N-methylthiolated β-lactam, which is a water-insoluble solid having a melting point of 92-93° C.

2-Chlorobenzaldehyde 21 was coupled with p-anisidine, to give imines 23. Staudinger coupling of acetoxyacetyl chloride with imine 22 gave $C_3$-acetoxy N-aryl protected β-lactam 23. Hydrolysis of acetoxy group under basic conditions gave the $C_3$-free hydroxyl β-lactam 24. Acylation of free hydroxyl β-lactam 24 with acryloyl chloride gave $C_3$-acryloyl N-aryl protected β-lactam 25. Dearylation of β-lactam 25 with ceric ammonium nitrate gave N-dearylated β-lactam 26, followed by methylthiolation with N-methylthio-phthalimide affords $C_3$-acryloyl N-methylthio 4-lactam 27 which is a white solid, mp 92-93° C.

Procedure for the Synthesis of N-(4-Methoxyphenyl)-(2-chlorophenyl)imine (22).

To a solution of p-anisidine (9.64 g, 78 mmol) in 25 ml of $CH_2Cl_2$ was added 2-chlorobenzaldehyde 21 (10.50 g, 64 mmol) and a catalytic amount of camphor-sulfonic acid. The resultant mixture was stirred until TLC indicated the disappearance of starting materials. The solvent was removed under reduced pressure, and the crude material was purified by recrystallization from methanol to yield 15.56 g (89%) of 22 as a yellow solid. mp 56-57° C. $^1$H NMR (250 MHz) δ 8.95 (s, 1H), 8.25 (m, 1H), 7.43-7.35 (m, 3H), 7.29 (d, J=8.6 Hz, 2H), 6.96 (d, J=8.6 Hz, 2H), 3.85 (s, 3H). $^{13}$C NMR (63 MHz) δ 158.6, 154.6, 144.5, 135.7, 133.4, 131.7, 129.8, 128.3, 127.0, 122.5, 114.3, 55.4.

Procedure for the Synthesis of 3-Acetoxy-N-(4-methoxyphenyl)-4-(2-chlorophenyl)-2-azetidinone (23).

To a stirred solution of N-(4-methoxyphenyl)-(2-chlorophenyl)imine 22 (17.00 g, 69.15 mmol) and triethylamine (26.8 g, 36 ml, 207.6 mmol) was added a solution of acetoxyacetyl chloride (9.76 g, 7.69 ml, 90.0 mmol) in methylene chloride (30 ml) dropwise over 10 minutes. The resultant mixture was stirred at room temperature until TLC indicated the disappearance of starting material. The solvent was removed under reduced pressure, and the crude material was purified by washing with ice-cold methanol to give 19.48 g (86%) of 23 as white solid, mp 130-132° C. $^1$H NMR (250 MHz) δ 7.43 (d, J=7.8 Hz), 7.29-7.24 (m, 5H), 6.83 (d, J=8.3 Hz, 2H), 6.16 (d, J=4.6 Hz, 1H), 5.78 (d, J=4.6 Hz, 1H), 3.76 (s, 3H), 1.76 (s, 3H). $^{13}$C NMR (63 MHz) δ 168.7, 161.4, 156.7, 133.8, 130.2, 130.0, 129.8, 128.7, 126.8, 118.6, 114.5, 75.4, 58.2, 55.4, 19.9.

Procedure for the Synthesis of 3-Hydroxy-N-(4-methoxyphenyl)-4-(2-chloro phenyl)-2-azetidinone (24).

To a solution of β-lactam 23 (8.00 g, 23.1 mmol) in 50 ml of acetone was added KOH (1.30 g, 23.1 mmol) in 20 ml of methanol at 0° C. The resultant mixture was stirred for 5 minutes, and 50 ml of water was added. The product was precipitated and isolated by filtration to yield 6.8 g (96%) of 24 as a white solid, mp 178-180° C. $^1$H NMR (250 MHz) δ 7.48 (d, J=7.3 Hz, 1H), 7.34-7.24 (m, 5H), 6.85 (d, J=9.0 Hz, 2H), 5.63 (d, J=5.1 Hz, 1H), 5.34 (d, J=5.1 Hz, 1H), 3.78 (s, 3H), 1.74 (bs, 1H). $^{13}$C NMR (63 MHz, DMSO-$d_6$), δ 166.6, 156.1, 133.1, 132.9, 131.0, 129.8, 129.6, 128.9, 127.4, 118.6, 115.0, 77.2, 60.0, 55.7.

Procedure for the Synthesis of 3-acryloyl-N-(4-methoxyphenyl)-4-(2-chlorophenyl)-2-azetidinone (25).

To a solution of $C_3$-hydroxy β-lactam 24 (5.80 g, 19.1 mmol) in 30 ml of freshly distilled $CH_2Cl_2$ was added NaH (60% suspension in mineral oil, 0.83 g, 21.0 mmol), and the mixture was stirred for 15 min at room temperature. Acryloyl chloride (2.59 g, 28.64 mmol) was then added dropwise and the resultant mixture was stirred until TLC indicated the disappearance of starting material. The reaction was quenched with a 5% solution of $NH_4Cl$ and extracted (3×20 ml) with $CH_2Cl_2$. The combined organic layers were dried over anhydrous $MgSO_4$ and purified with column chromatography on silica gel (1:4, EtOAc:hexanes) to give 4.92 g (72%) of 25 as a white solid, mp 99-100° C. $^1$H NMR (250 MHz) δ 7.33 (d, J=7.9 Hz, 1H), 7.23-7.10 (m, 5H), 6.75 (d, J=8.9 Hz, 2H), 6.17 (d, J=5.0 Hz, 1H), 5.98 (dd, J=16.9, 1.00 Hz, 1H), 5.74 (dd, J=16.9, 10.4 Hz, 1H), 5.69 (d, J=5.0 Hz, 1H), 5.59 (d, J=10.4, 1.0 Hz, 1H), 3.66 (s, 3H). $^{13}$C NMR (63 MHz) δ 163.6, 161.2, 156.6, 133.7, 132.3, 130.3, 130.1, 129.8, 128.5, 126.8, 126.5, 118.6, 114.4, 75.3, 61.3, 58.2, 55.3.

Procedure for the Synthesis of 3-acryloyl-N-methylthio-4-(2-chlorophenyl)-2-azetidinone (27).

To a solution of 25 (4.00 g, 11.2 mmol) in 40 ml of $CH_3CN$ in an ice-water bath was added ceric ammonium nitrate (18.39 g, 33.54 mmol) in 40 ml of water. The resultant mixture was stirred for 5 min, and 20 ml of water was added. The solution was extracted (3×5 ml) with EtOAc. The combined organic layers were washed with 5% $NaHSO_3$, 5% $NaHCO_3$, and dried over anhydrous $MgSO_4$. The solvent was removed under reduced pressure to yield 2.14 g (76%) of 26 as a crude brown oil. Without further purification, compound 26 (2.00 g, 8.0 mmol) was dissolved in 30 ml of dry $CH_2Cl_2$ and N-(methylthio)phthalimide (2.30 g, 11.9 mmol) and 3-5 drops of triethylamine were added. The resultant mixture was refluxed for overnight. The solvent was removed under reduced pressure to yield a brown solid. The brown solid was redissolved in $CH_2Cl_2$, and washed with 1% NaOH. The organic layer was dried over anhydrous MgSO$_4$. The solvent was removed under reduced pressure to yield a brown semi-solid, which was purified by column chromatography on silica gel with gradient elution (1:9 then 1:4 EtOAc:hexanes) to yield 2.00 g (88%) of 27 as a white solid. $^1$H NMR (250 MHz) δ 7.35-7.26 (m, 4H), 6.20 (d, J=5.1 Hz, 1H), 6.06 (dd, J=16.7, 1.9 Hz, 1H), 5.78 (dd, J=16.7, 10.4 Hz, 1H), 5.68 (dd, J=10.4, 1.9 Hz, 1H), 5.54 (d, J=10.4 Hz, 1H), 2.51 (s, 3H). $^{13}$C NMR (63 MHz) δ 168.3, 163.4, 156.6, 134.3, 132.6, 129.8, 128.6, 126.6, 126.3, 62.1, 21.9.

Example 2

Nanoparticles of copoly(ethylacrylate, N-methylthiolated β-lactam) (CPETL) were prepared by a radical polymerization using potassium persulfate as the initiator and the sodium salt of dodecyl sulfate as the surfactant. The mixture of (±)-(3S,4R)-4-ortho-chlorophenyl-3-acryloyl-1-(methylthio) azetidin-2-one (500 mg, white solid, mp 92-93° C.), as synthesized in Example 1, and ethyl acrylate (500 mg) was warmed to 70° C. with slow stirring under a nitrogen atmosphere and was stirred for 30 minutes to form a homogeneous solution. The nano-pure water (7.94 ml) containing dodecyl sulfate, sodium salt (ACROS, 10 mg) was added with vigorous stirring and the mixture was stirred for 60 minutes, to give the milky pre-emulsion state. The solution of potassium persulfate (SIGMA, 5 mg) in nano pure water (0.3 ml) was added under nitrogen atmosphere, and the reaction was stirred for 5 hours at 70° C. The additional solution of potassium persulfate (SIGMA, 1 mg) in nano pure water (0.1 ml) was added three times in the polymerization mixture per every one hour, to give a milky emulsion solution.

Polymeric nanoparticles with various drug loadings were synthesized in accordance with the reactants of Table 1.

The mole ratio of each monomer in the polymer can be determined by $^1$H NMR spectrum after film casting. The solid content was determined by the conventional drying method. A small piece of aluminum foil was pre-weighed (129.9 mg), and then, a certain amount of the emulsion solution was loaded on the aluminum foil and weighed. The total amount of aluminum foil and sample was 196.0 mg. After drying for 24 hours at 25° C., the total amount of the residue and the aluminum foil left on aluminum foil was checked, (140.5 mg). The loading amount of emulsion solution can be determined from equation 1 (66.1 mg). The total solid amount left on the aluminum foil after drying can be determined from equation 2 (10.6 mg). Therefore, the solid content can be calculated from equation 3 (16.04%). The same procedure was repeated two more times, giving values of 16.64% and 16.12% respectively. The average solid content from these 3 values was 16.27%.

(the weight of aluminum foil and sample)−(the weight of aluminum foil)     (Eq. 1)

(the total weight of the residue and the aluminum foil after drying)−(the weight of aluminum foil)     (Eq. 2)

(Eq. 2)÷(Eq. 1)×100     (Eq. 3)

The solid contents for the other analogous emulsion solutions can be obtained similarly.

Figure 3:
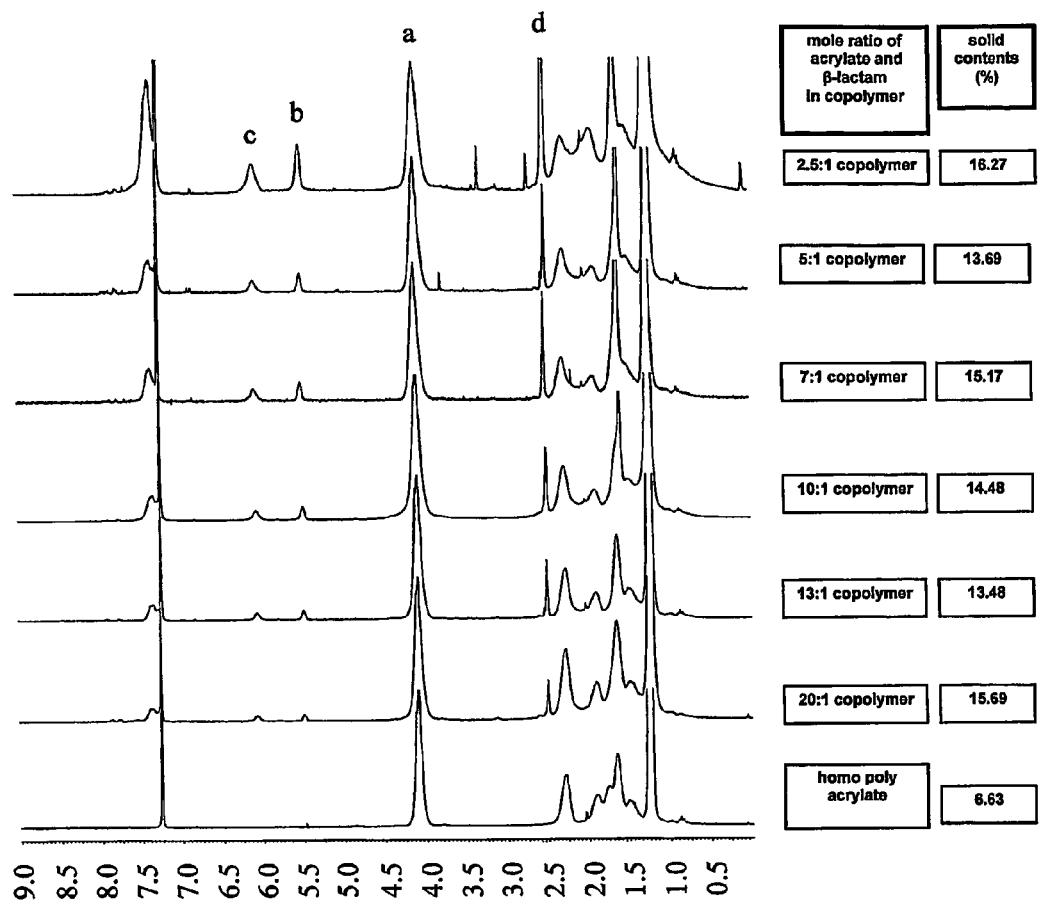
FIG. 3 shows the $^1$H NMR spectrums for N-methylthiolated β-lactam. The spectrum compares the differences and similarities for different mole ratios of acrylate to β-lactam in copolymer.

FIG. 3 shows the $^1$H NMR spectrums after film casting and the solid contents for N-methylthiolated β-lactam polymers. Signals at (d) 2.6, (b) 5.6 and (c) 6.1 ppm are assigned to S—CH$_3$, C$_3$—H and C$_4$—H on β-lactam respectively. The signal at (a) 4.0 ppm is assigned to the methylene proton of ethyl acrylate. The olefin protons of acrylate in the range of 5.6-6.1 ppm do not show in the spectrum. That indicates that all of the monomeric β-lactam acrylate and ethyl acrylate was converted to polymeric particles. In addition, the composition of the polymeric nanoparticles can be determined by $^1$H NMR spectroscopy as mentioned. The mole ratio of β-lactam and ethyl acrylate in the copolymer was determined from the peak integration of the methylene proton (a) of ethyl acrylate and a proton of C$_3$ (b) or C$_4$ (c) on the β-lactam respectively.

To characterize the copolymers of N-methylthiolated β-lactam and ethyl acrylate, the $^1$H NMR spectra of the dried polymeric film was analyzed after coalescence. To provide the polymeric sample for NMR, 2-3 drops of the original emulsion solution was placed on the glass plate and then allowed to dry for 24 hours. The resulting polymeric films were dissolved in CDCl$_3$ with warming the sample and then subjected to NMR studies.

TABLE 1

Formulation of Microemulsion Polymerization

| entry | mole ratio EA[1]: β-lactam[1] | monomers (mg) β-lactam[1] | EA[1] | surfactant (mg) lauryl sulphate | initiator (mg) persulphate[1] | water (ml) | rxn. temp.(° C.) |
|---|---|---|---|---|---|---|---|
| 1 | EA homo | 0 | 1000 | 20 | 5.0 | 5.0 | 60 |
| 2[2] | 20:1 | 100 | 700 | 16 | 4.0 | 4.0 | 70 |
| 3[2] | 13:1 | 100 | 456 | 12 | 3.0 | 2.8 | 70 |
| 4[2] | 10:1 | 100 | 350 | 9 | 2.5 | 2.3 | 70 |
| 5[2] | 7:1 | 100 | 245 | 7 | 1.8 | 1.8 | 70 |
| 6[2] | 5:1 | 100 | 175 | 6 | 1.5 | 1.4 | 70 |
| 7[2] | 2.5:1 | 100 | 88 | 3 | 0.8 | 0.7 | 70 |

[1]EA: ethyl acrylate, β-lactam: C$_3$-acryloyl N-methylthio β-lactam, lauryl sulphate: sodium salt, persulphate: potassium salt.
[2]The scale was varied several times based on volume.

SEM studies were performed to characterize the particle size and the morphology of polymeric nanoparticles. To provide the sample of polymeric nanoparticles for SEM, the original emulsion solution was diluted to 20000-30000 [fold or X] using nano pure water and then one drop of the diluted emulsion solution was put on a small piece of silicon wafer. The water drop was evaporated with air blowing and sputtering with gold. The sample was subjected to the SEM as shown in FIGS. 4A-4G.

Figure 4A:
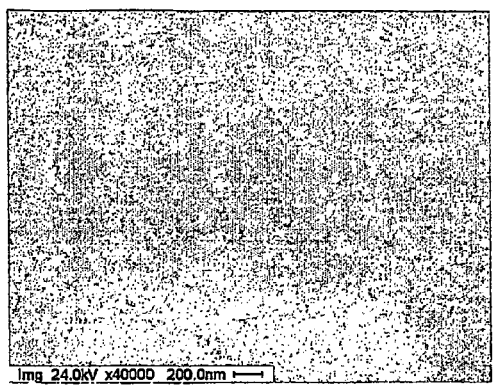
FIG. 4A shows a scanning electron micrograph of homo polyacrylate nanoparticles.
Figure 4B:
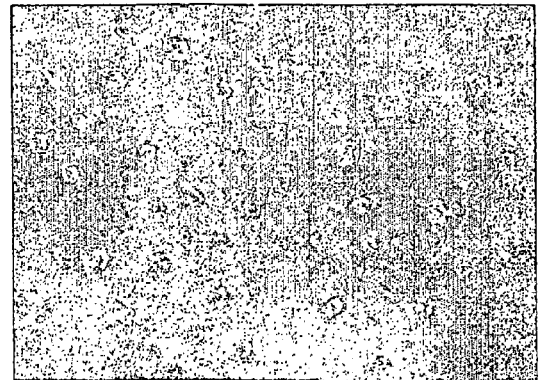
FIG. 4B shows a scanning electron micrograph of nanoparticles with an acrylate to N-methylthiolated β-lactam mole ratio of 20:1.
Figure 4C:
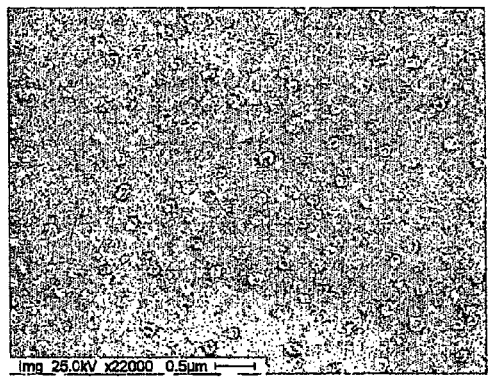
FIG. 4C shows a scanning electron micrograph of nanoparticles with an acrylate to N-methylthiolated β-lactam mole ratio of 13:1.
Figure 4D:
FIG. 4D shows a scanning electron micrograph of nanoparticles with an acrylate to N-methylthiolated β-lactam mole ratio of 10:1.
Figure 4E:
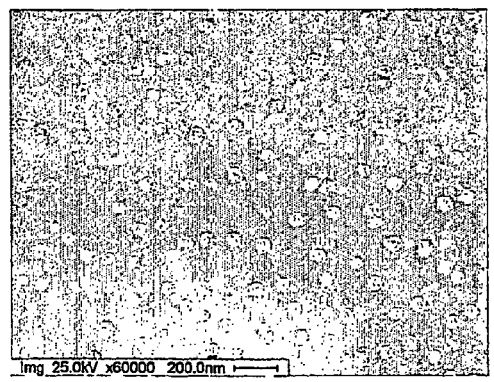
FIG. 4E shows a scanning electron micrograph of nanoparticles with an acrylate to N-methylthiolated β-lactam mole ratio of 7:1.
Figure 4F:
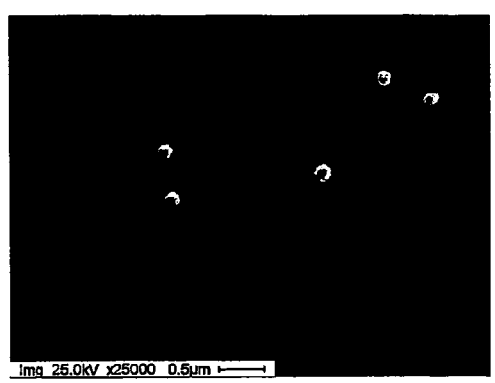
FIG. 4F shows a scanning electron micrograph of nanoparticles with an acrylate to N-methylthiolated β-lactam mole ratio of 5:1.
Figure 4G:
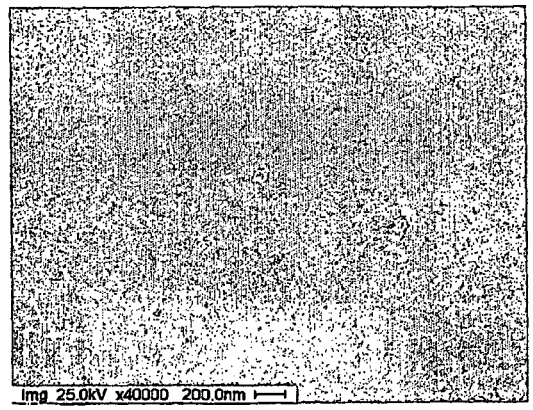
FIG. 4G shows a scanning electron micrograph of nanoparticles with an acrylate to N-methylthiolated β-lactam mole ratio of 2.5:1.
Figure 55:
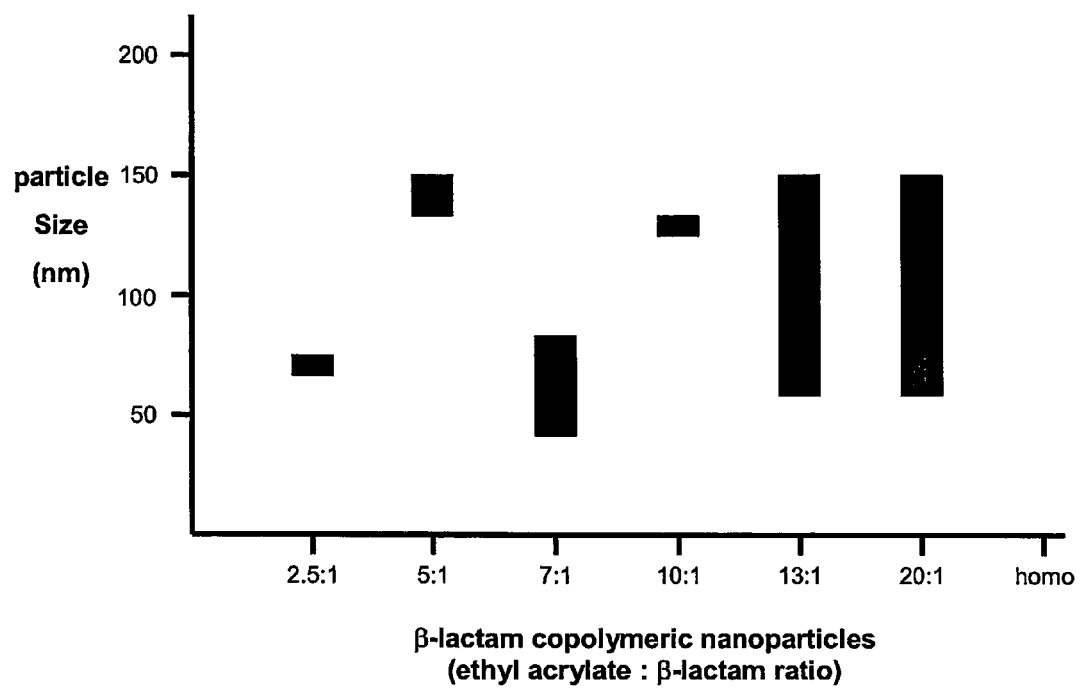
FIG. 55 shows particle size distribution of β-lactam copolymeric nanoparticles.
Figure 56:
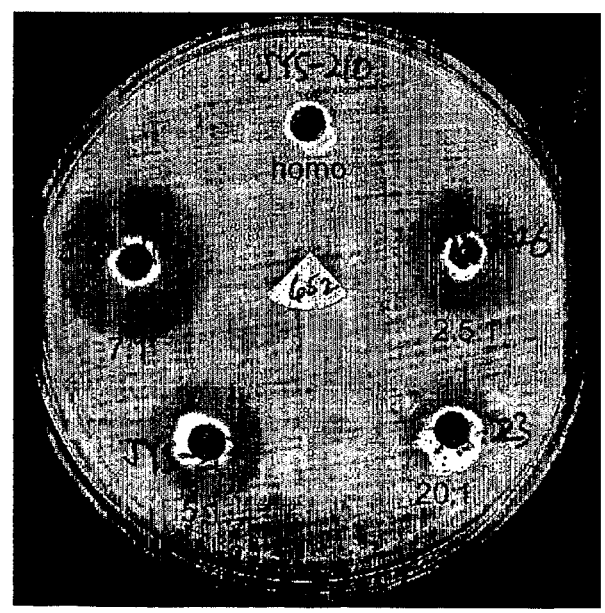
FIG. 56 shows antibacterial testing of drug-embedded nanoparticles against MRSA 652 (ratios of ethyl acrylate: lactam indicated).
Figure 57:
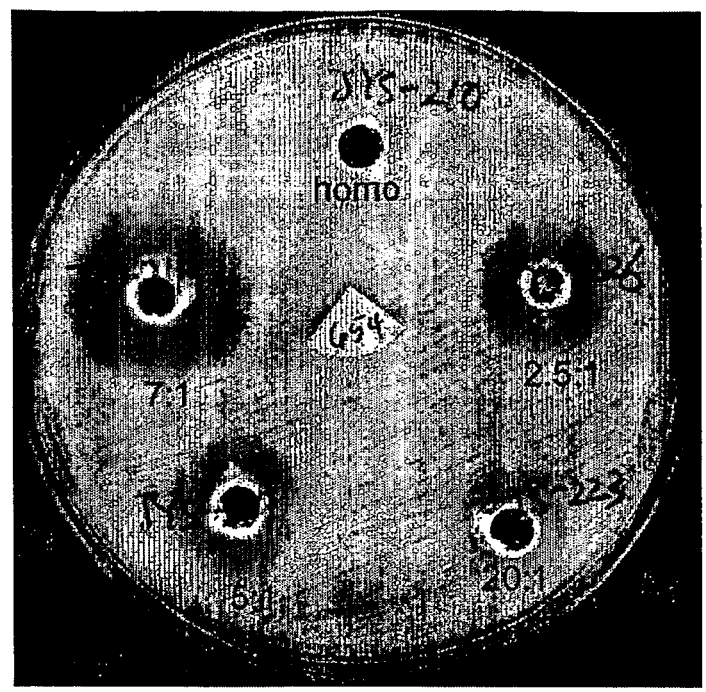
FIG. 57 shows antibacterial testing of drug-embedded nanoparticles against MRSA 654 (ratios of ethyl acrylate: lactam indicated).
Figure 58:
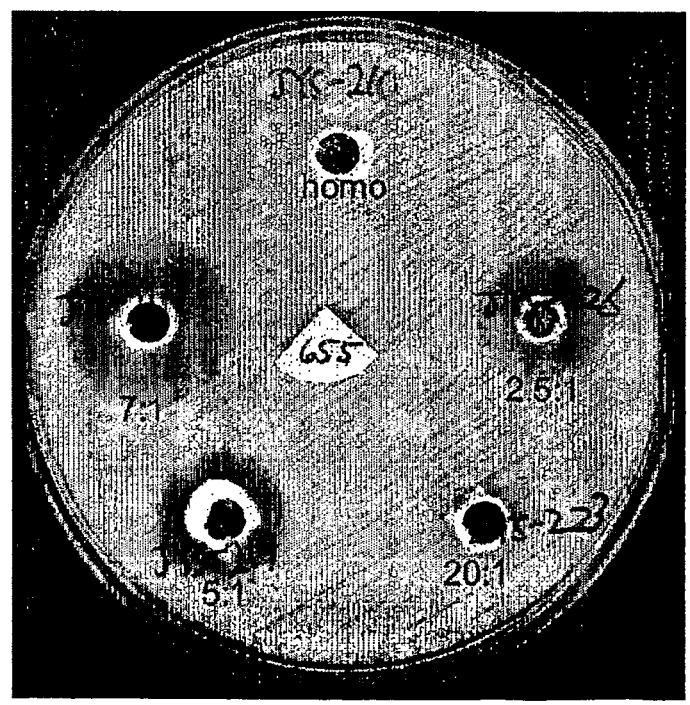
FIG. 58 shows antibacterial testing of drug-embedded nanoparticles against MRSA 655 (ratios of ethyl acrylate: lactam indicated).
Figure 59:
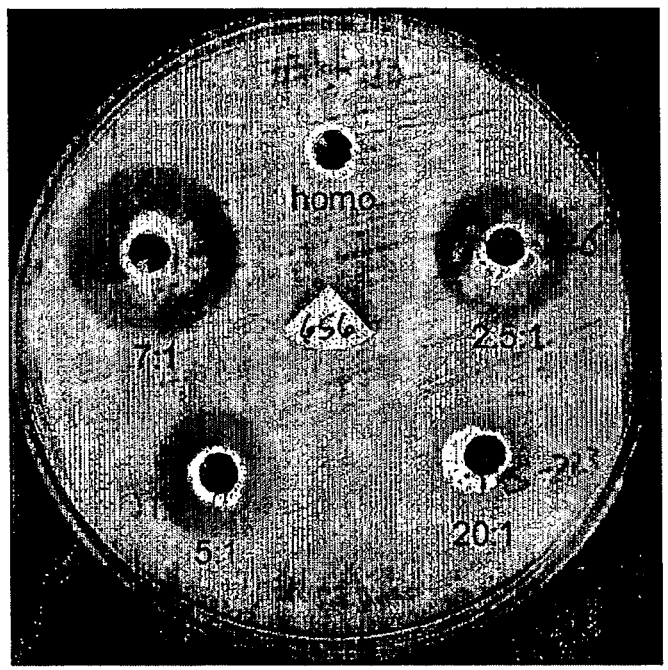
FIG. 59 shows antibacterial testing of drug-embedded nanoparticles, against MRSA 656 (ratios of ethyl acrylate: lactam indicated).
Figure 60:
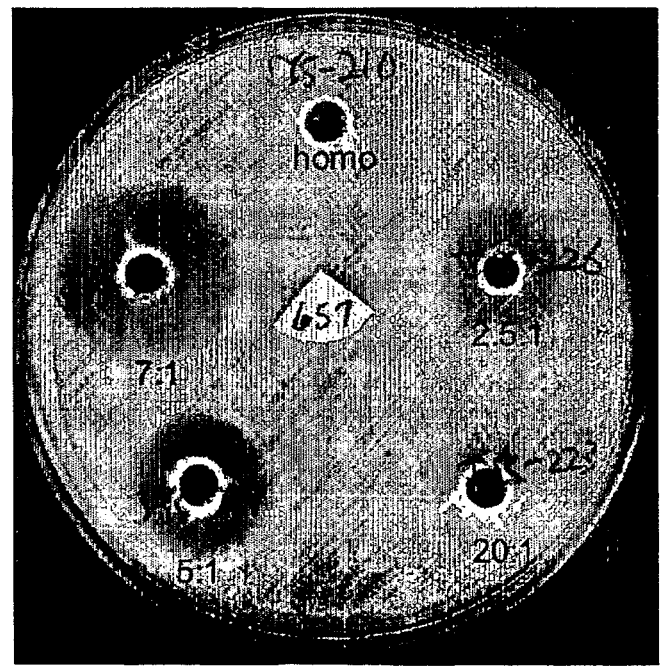
FIG. 60 shows antibacterial testing of drug-embedded nanoparticles against MRSA 657 (ratios of ethyl acrylate: lactam indicated).
Figure 61:
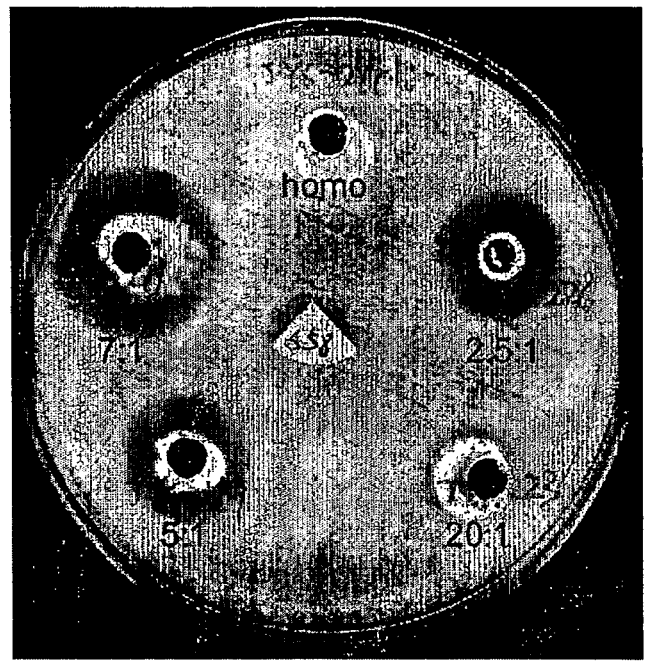
FIG. 61 shows antibacterial testing of drug-embedded nanoparticles against MRSA 658 (ratios of ethyl acrylate: lactam indicated).
Figure 62:
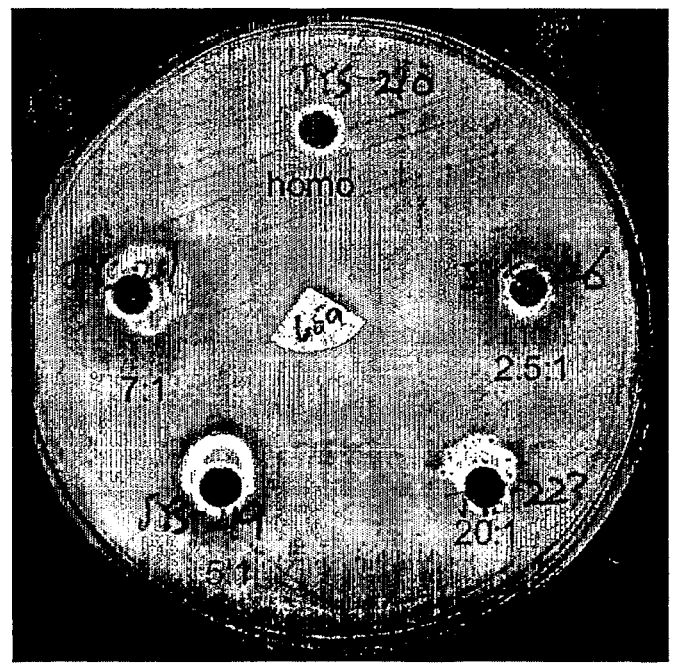
FIG. 62 shows antibacterial testing of drug-embedded nanoparticles against MRSA 659 (ratios of ethyl acrylate: lactam indicated).
Figure 63:
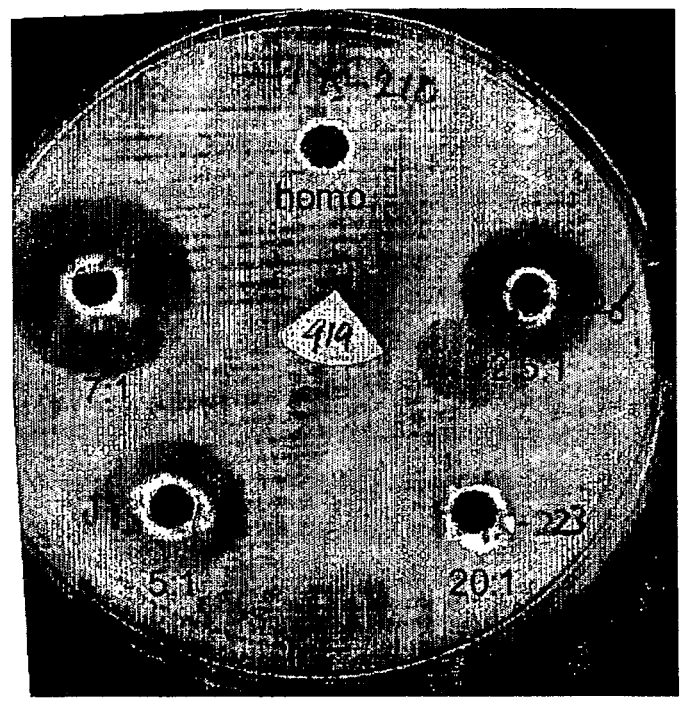
FIG. 63 shows antibacterial testing of drug-embedded nanoparticles against MRSA 919 (ratios of ethyl acrylate: lactam indicated).
Figure 64:
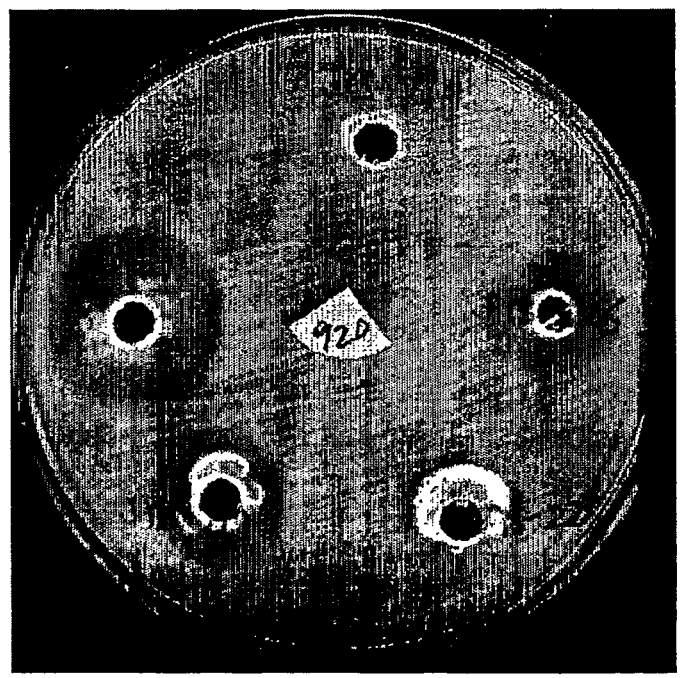
FIG. 64 shows antibacterial testing of drug-embedded nanoparticles against MRSA 920 (ratios of ethyl acrylate: lactam indicated).
Figure 65:
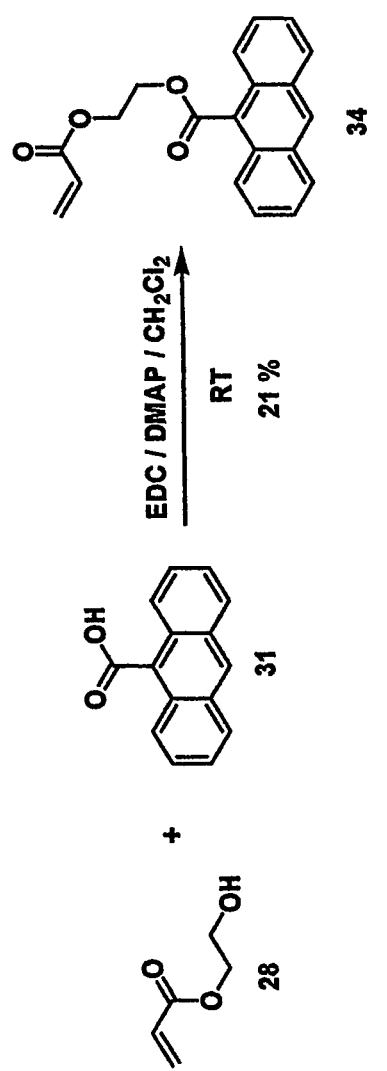
FIG. 65 shows an acrylation of 9-anthracene-carboxylic acid.
Figures 66A, 66B:
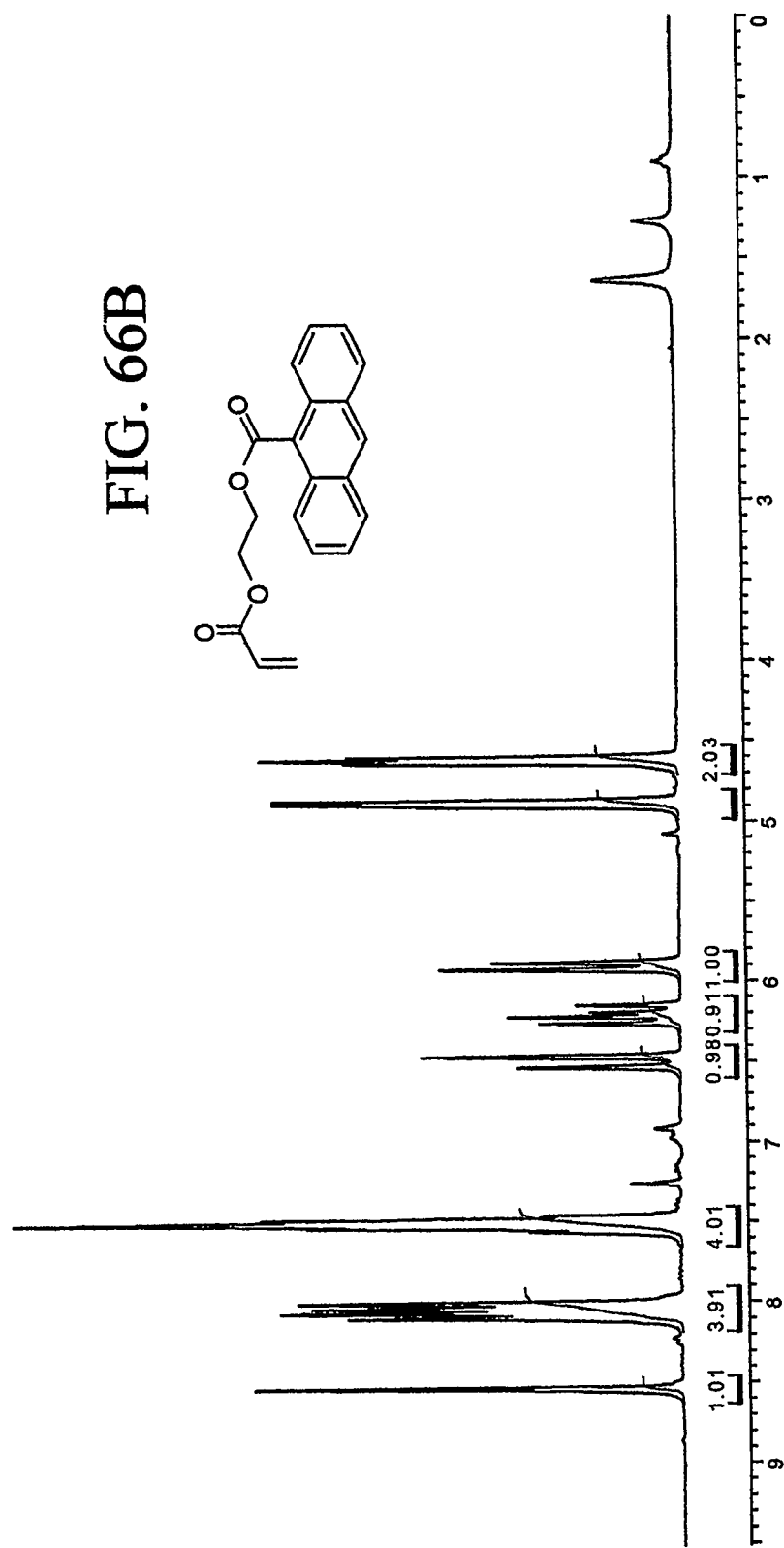
FIGS. 66A and 66B.

The particle size and the morphology for the polymeric particles can be determined by scanning electron microscopy (SEM) and dynamic light scattering. FIGS. 4A-4G shows the SEM pictures of polymeric particles for N-methylthiolated β-lactams. Those particle size and morphology are around 40-150 nm and microspheric respectively. In FIG. 4E the 7:1 acrylate:lactam copolymer shows the most uniform particle sizes (40-80 nm). FIG. 55 illustrates the particle size distribution of these β-lactam copolymeric nanoparticles.

Figure 5:
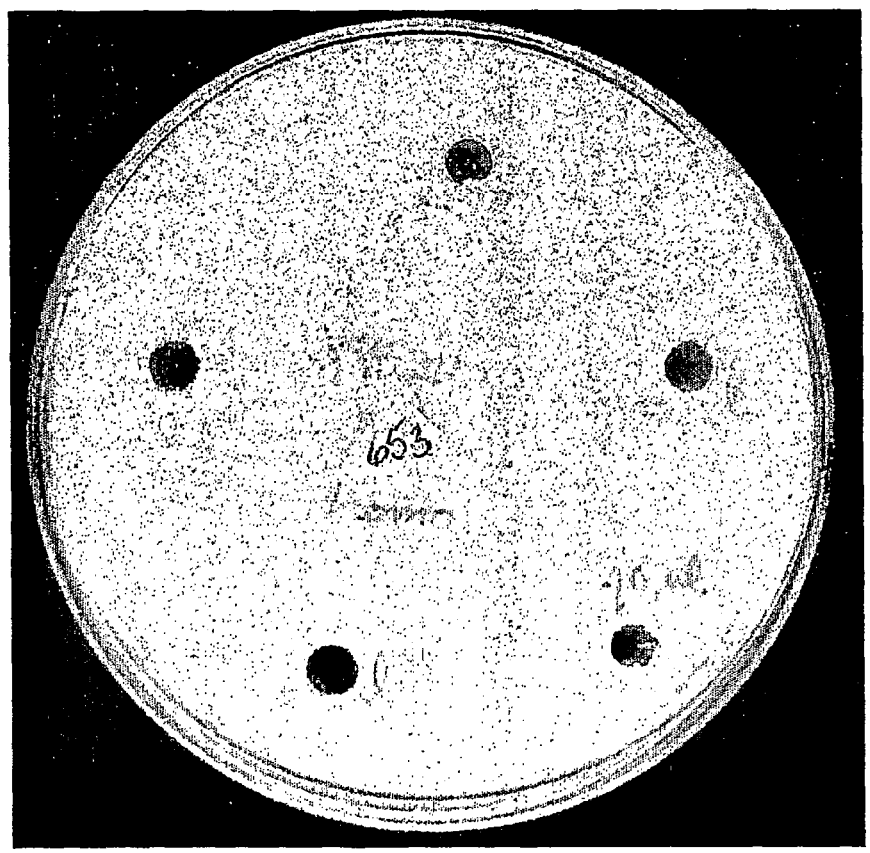
FIG. 5 shows scanning electron micrographs demonstrating the antibacterial activity exhibited by ethyl acrylate homopolymeric nanoparticles on MRSA 653.

The antibacterial activity for ethyl acrylate homopolymeric nanoparticles was determined using the MRSA 653 strain as a standard and the Kirby-Bauer method of disc diffusion on agar plates. The 20, 40, 60, 80 and 100 µl of homopolymeric nanoparticles (6.63% of solid content) was loaded into 6-mm wide holes bored into the agar and the plate was incubated at 37° C. for 24 hours. FIG. 5 shows that no growth inhibition was observed.

Figure 6:
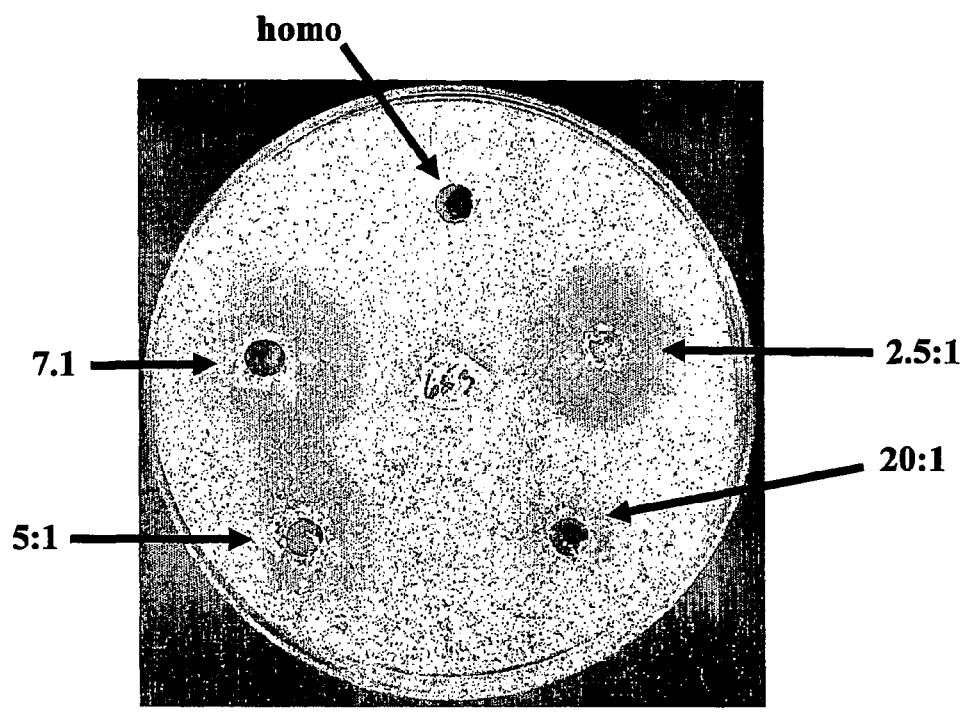
FIG. 6 shows antibacterial testing of N-methylthiolated β-lactam nanoparticles for MRSA 653.

The antibacterial activity for N-methylthiolated β-lactam polymeric nanoparticles, 2.5:1, 5:1, 7:1, 20:1 and homopolymeric was performed against various strains of bacteria. Table 2 shows zones of inhibition obtained from agar well diffusion experiments using 20 µl of the emulsified suspension of the test nanoparticles. FIGS. 5-7 and 56-64 illustrate the various agar plate bioactivities. The values correspond to the diameters in mm for the zone of growth inhibition appearing around the well after 24 hours. *Staphylococcus aureus* and β-lactamase-producing strains of methicillin-resistant *Stapitylococcus aureus* (labeled MRSA USF652-659) were obtained from a clinical testing laboratory at Lakeland Regional Medical Center, Lakeland, Fla. or from ATCC sources. The 20 µl of each polymeric nanoparticle was loaded into 6-mm wide holes bored into the agar and the plate was incubated at 37° C. for 24 hours. FIG. 6 shows that all N-methylthiolated β-lactam polymeric nanoparticles, 2.5:1, 5:1, 7:1, 20:1 are active, especially 7:1 was the most active.

TABLE 2

Zones of Inhibition

| strains | | homo EA | 20:1 | 15:1 | 10:1 | 7:1 | 5:1 | 2.5:1 |
|---|---|---|---|---|---|---|---|---|
| MRSA | 652 | 0 | 14 | 11 | 18 | 23 | 16 | 17 |
| | 653 | 0 | 15 | 13 | 24 | 28 | 24 | 24 |
| | 654 | 0 | 14 | 12 | 15 | 23 | 17 | 16 |
| | 655 | 0 | 0 | 11 | 18 | 22 | 17 | 15 |
| | 656 | 0 | 12 | 15 | 18 | 23 | 17 | 18 |
| | 657 | 0 | 12 | 12 | 18 | 24 | 17 | 16 |
| | 658 | 0 | 0 | 12 | 17 | 24 | 18 | 16 |
| | 659 | 0 | 0 | 14 | 16 | 22 | 17 | 17 |
| | 919 | 0 | 0 | 11 | 17 | 22 | 17 | 17 |
| | 920 | 0 | 0 | 12 | 16 | 23 | 18 | 16 |
| S. aureus | 849 | 0 | 13 | 16 | 18 | 24 | 20 | 19 |

*ethyl acrylate (EA)

Figure 7:
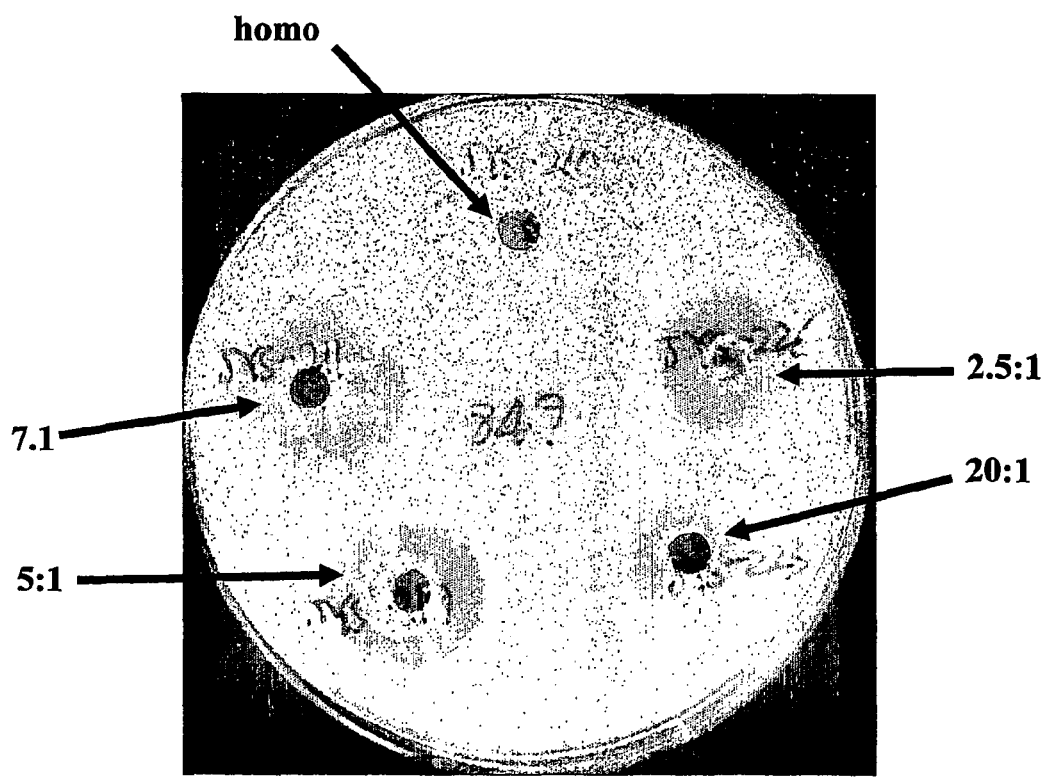
FIG. 7 shows antibacterial testing of N-methylthiolated β-lactam nanoparticles for S. aureus 849.

The antibacterial activity for N-methylthiolated β-lactam polymeric nanoparticles, 2.5:1, 5:1, 7:1, 20:1 and home was performed at *S. aureus* 849 strain. The 20 µl of each polymeric nanoparticle were loaded into 6-mm wide holes bored into the agar and the plate was incubated at 37° C. for 24 hours. FIG. 7 shows that all N-methylthiolated β-lactam polymeric nanoparticles, 2.5:1, 5:1, 7:1, 20:1 are active, especially 7:1 was the most active.

It is apparent that all N-methylthio β-lactam containing nanoparticles are active against MRSA strains as well as the non-resistant strain, *S. aureus* 849. Their activity trend appears to increase gradually as the portion of drug (β-lactam) increases from 20:1 (ethyl acrylate:antibiotic) to the 7:1 and reaches the maximum at the 7:1 ratio. However, the bioactivity decreased for particles having an ethyl acrylate:lactam ratio of 5:1, and the activities of the 5:1 and 2.5:1 nanoparticles are similar even though the portion of drug (β-lactam) is increased. Therefore, the result indicates that the antibacterial performance of N-methylthio β-lactam containing nanoparticles is enhanced dramatically over that of the free antibiotic, and the 7:1 (ethyl acrylate:lactam) nanoparticles show the best activity.

The comparison of antibacterial activity of the N-methylthio β-lactam containing emulsified nanoparticles and the standards: penicillin G (Pen. G), vancomycin, and $C_3$-acryloyl β-lactam 27 against MRSA, shows that the emulsified nanoparticles have similar and/or better activities at very low drug amount compared with those of standards. However, the activity of 7:1 (ethyl acrylate:lactam) nanoparticles are better even at low drug amount (0.91 µg) compared with that of vancomycin (20 µg). It is likely that the activity of the 7:1 nanoparticles is over 20 times more than that of vancomycin.

Figure 8:
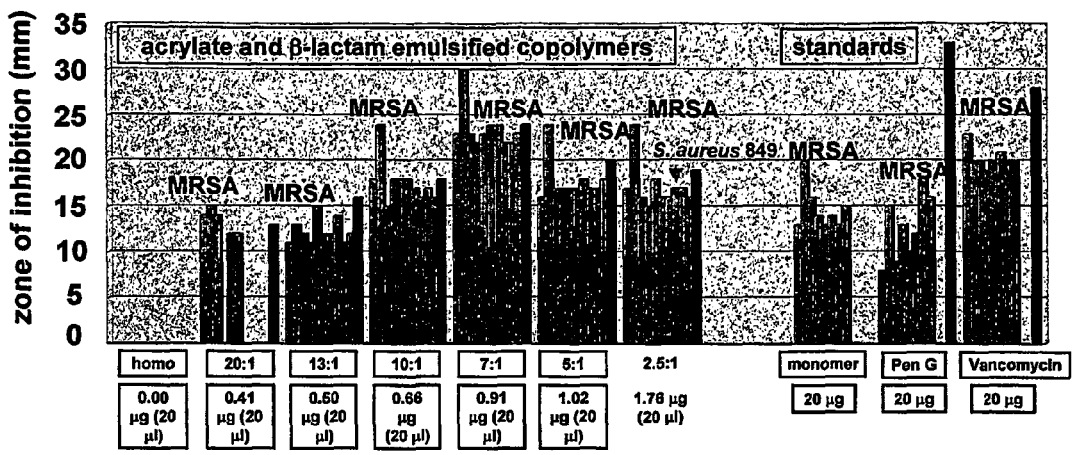
FIG. 8 shows antibacterial activity exhibited by N-methylthiolated β-lactam nanoparticles, standards and actual β-lactam loading amounts (determined by the mole ratio of each monomer in the $^1$H NMR spectrum, the loading volume (μl) and the solid contents (%).

A summary of the antibacterial activity for the N-methylthiolated β-lactam polymeric nanoparticles, 2.5:1, 5:1, 7:1, 20:1, and the standards is illustrated in FIG. 8.

Figure 9:
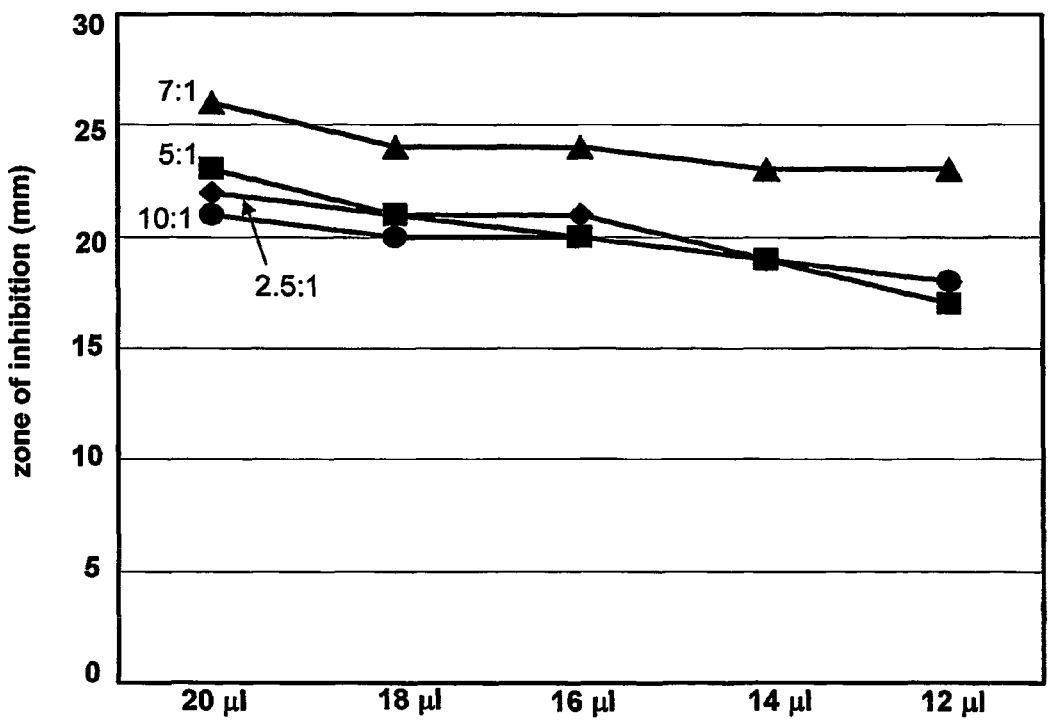
FIG. 9 shows bioactivity of polymeric nanoparticles as a function of disk loading amounts for MRSA 653.

The antibacterial activity of N-methylthiolated β-lactam polymeric nanoparticles, 2.5:1, 5:1, 7:1 and 20:1 versus decreasing loading amount against MRSA 653 strain. The polymeric nanoparticles were loaded into 6-mm wide holes bored into the agar, with the loading amount decreasing from 20 to 12 µl. The plate was incubated at 37° C. for 24 hours. FIG. 9 shows that all N-methylthiolated β-lactam polymeric nanoparticles, 2.5:1, 5:1, 7:1,20:1 are still active even though the loading amount was decreased to 12 µl.

Figure 10:
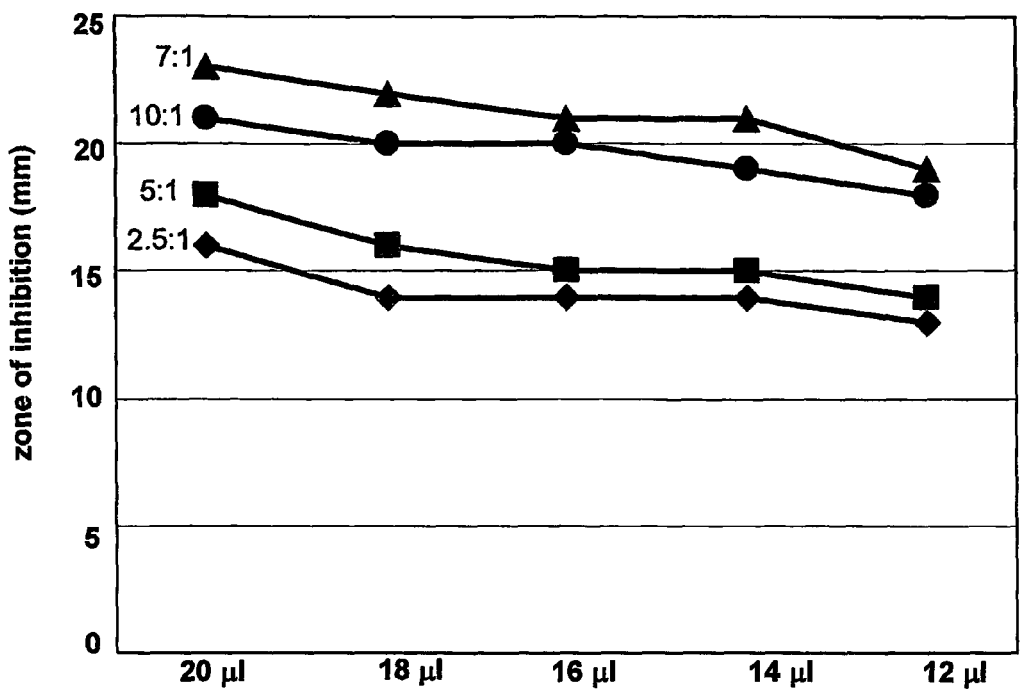
FIG. 10 shows the bioactivity of polymeric nanoparticles as a function of disk loading amounts for S. aureus 849.

The antibacterial activity for N-methylthiolated β-lactam polymeric nanoparticles (2.5:1, 5:1, 7:1 and 20:1) was checked out as decreasing loading amount at *S. aureus* 849 strain. The polymeric nanoparticles were loaded into 6-mm wide holes bored into the agar, with the loading amount decreasing from 20 to 12 µl. The plate was incubated at 37° C. for 24 hours. FIG. 10 shows that all N-methylthiolated β-lactam polymeric nanoparticles, 2.5:1, 5:1, 7:1, 20:1 are still active even though the loading amount was decreased to 12 µl.

Figure 11:
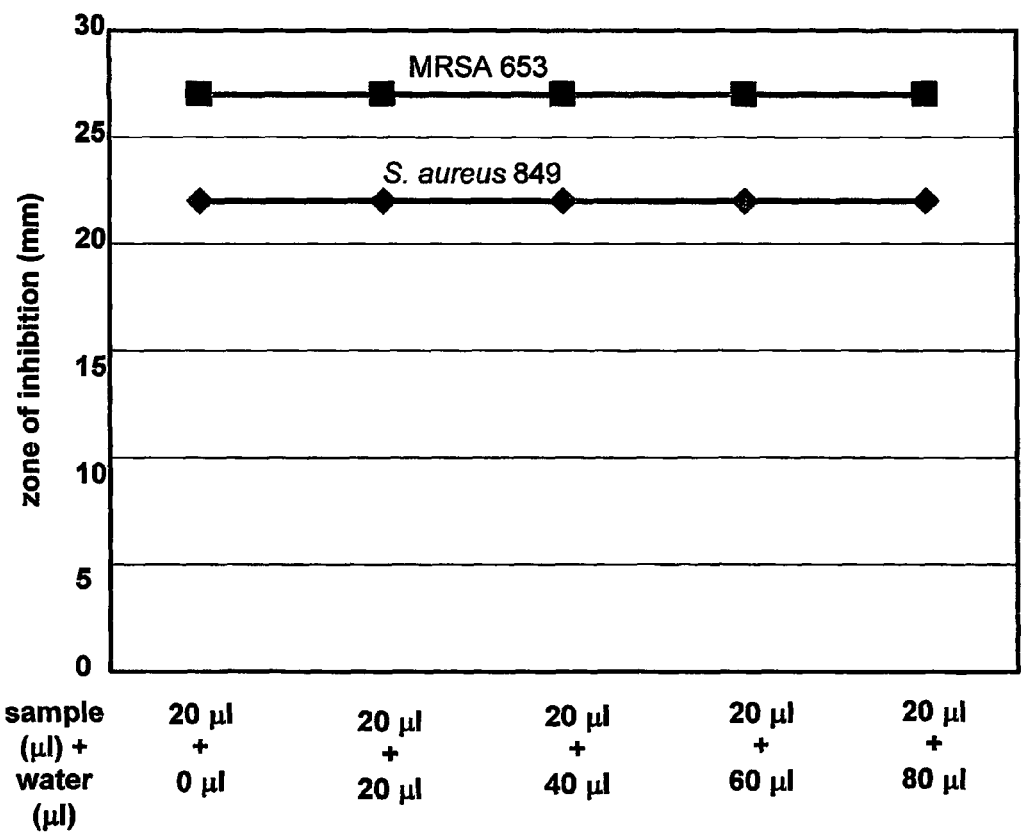
FIG. 11 shows the bioactivity of 7:1 (acrylate:N-methylthiolated β-lactam) polymeric nanoparticles as a dilution with water on fixed disk loading amounts.

The antibacterial activity for N-methylthiolated β-lactam polymeric nanoparticles (2.5:1, 5:1, 7:1 and 20:1) diluted with water was measured at MRSA 653 and *S. aureus* 849 strains. The fixed amount (20 µl) of 7:1 polymeric nanoparticles was loaded at five spots of agar plate, and then the amount of water was loaded for each spot as increasing from 0 to 80 µl and the plate was incubated at 37° C. for 24 hours. FIG. 11 shows that the antibacterial activities are independent of concentration.

Figure 12:
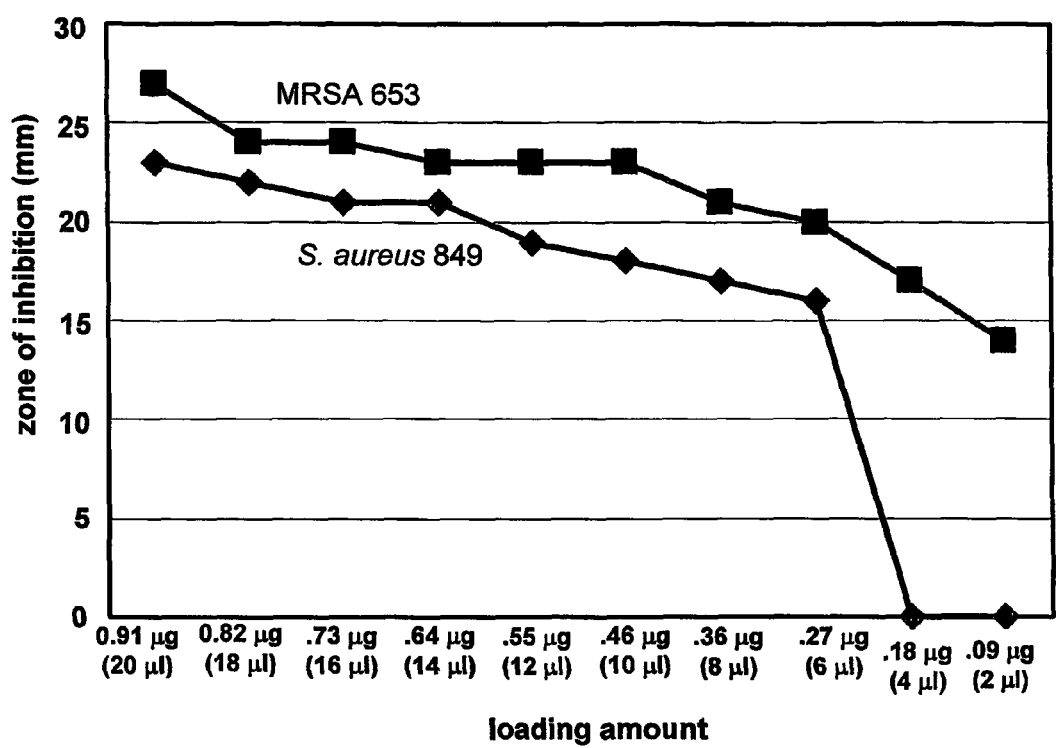
FIG. 12 shows the bioactivity of 7:1 (acrylate:N-methylthiolated β-lactam) polymeric nanoparticles as a function of disk loading amounts.

The antibacterial activity for N-methylthiolated β-lactam polymeric nanoparticles, 7:1 was analyzed for decreasing the loading amount at MRSA 653 and *S. aureus* 849 strains. The polymeric nanoparticles were loaded into 6-mm wide holes bored into the agar, with the loading amount from 20 to 2 µl decreasing and the plate was incubated at 37° C. for 24 hours. FIG. 12 shows that N-methylthiolated β-lactam polymeric nanoparticles, 7:1, is still active even though the loading amount was decreased to 2 µl (about 1 µg of drug).

Figure 13:
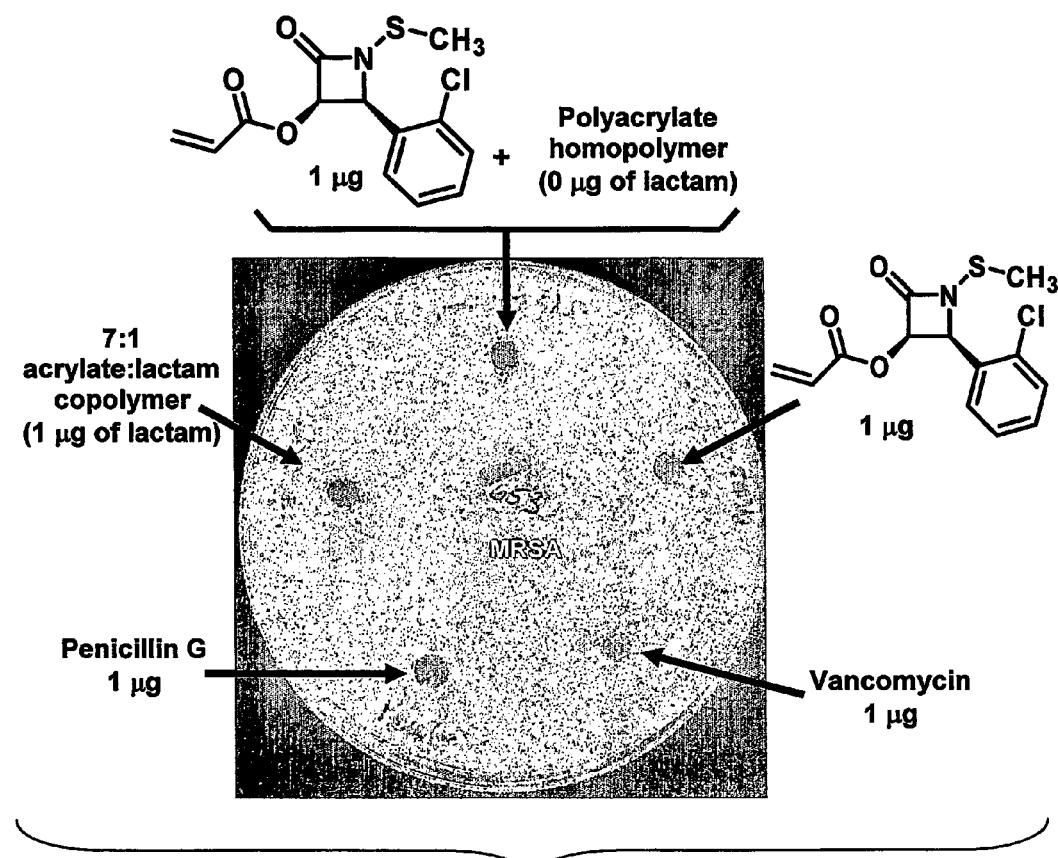
FIG. 13 shows scanning electron micrographs for the antibacterial activity for constant drug loading.

FIG. 13 illustrates that the activity of the 7:1 polymeric nanoparticles is significantly enhanced when the loading amount of drugs were limited to 1 µg.

Antifungal testing of these nanoparticles was performed by Kirby-Bauer disc diffusion on agar plates against eight genera of fungi. Table 3 displays the zones of inhibition observed nanoparticles. It is very interesting that nanoparticles are very active against all of the fungal strains, with antifungal activity of the N-thiolated lactam (1 µg) in the nanoparticles being similar to that of the standard, clotrimazole (50 µg). That means the 7:1 (acrylate:lactam) nanoparticles are fifty times more potent than clotrimazole. This indicates that drug containing nanoparticles are promising leads to new antifungal agents as well as an antibacterial antibiotics.

TABLE 3

Zones of inhibition obtained from agar well diffusion experiments using 20 ml of 7:1 (ethyl acrylate:lactam) nanoparticle emulsion. This corresponds to 1 mg of active drug in the particle. The values correspond to the diameters in mm for the zone of growth inhibition appearing around the after 48 hours.

| fungal strains* | nanoparticles | | | | standard |
| --- | --- | --- | --- | --- | --- |
| | $1^{st}$ | $2^{nd}$ | $3^{rd}$ | average | clotrimazole (50 μg) |
| C. albicans | 26 | | | 26 | 20 |
| C. tropicalis | 20 | 24 | | 22 | 20 |
| C. glabrata | 19 | 20 | 16 | 18 | 14 |
| C. kefyr | 21 | 23 | 20 | 21 | 37 |
| C. krusei | 24 | 27 | 29 | 27 | 27 |
| C. lusitaniae | 31 | 32 | 32 | 32 | 25 |
| C. parapsilosis | 19 | 20 | 22 | 20 | 32 |
| C. utilis | 22 | 23 | 23 | 23 | 24 |

*Fungi were chosen on the basis of their potential pathogenicity. C. albicans and C. tropicalis were donated by Dr. Ray Widen from the University of South Florida, School of Medicine. C. glabrata (ATCC 15126), C. krusei (ATCC 14243), C. kefyr (ATCC 20409), C. parapsilosis (ATCC 22019), C. lusitaniae (ATCC 34449) and C. utilis (ATCC 29950) were obtained commercially.

Example 3

FIG. 14 illustrates the modification of the anti-inflammatory drug sulindac in preparation for reaction with an acrylic monomer to form a nanoparticle. An acrylate, 2-hydroxyethyl acrylate, reacts with sulindac, a water-insoluble solid, to synthesize an ester of sulindac as a highly viscous liquid. The liquid can be further processed to form a nanoparticle polymer that is uniformly dispersed in aqueous media.

Example 4

FIG. 15 illustrates the modification of penicillin G. 2-hydroxyethyl acrylate reacts with penicillin G to provide the linker required in the synthesis of polymeric nanoparticles loaded with penicillin G.

Example 5

A $C_4$-acrylate β-lactam analogue is synthesized from imine starting material according to FIGS. 41A-41D. This analog is prepared in a four step process, wherein an imine is converted to a β-lactam. The acetoxy groups of the β-lactam are replaced by acrylates, and the aryl group attached to the nitrogen is replaced with a methyl thio group.

Figure 42:
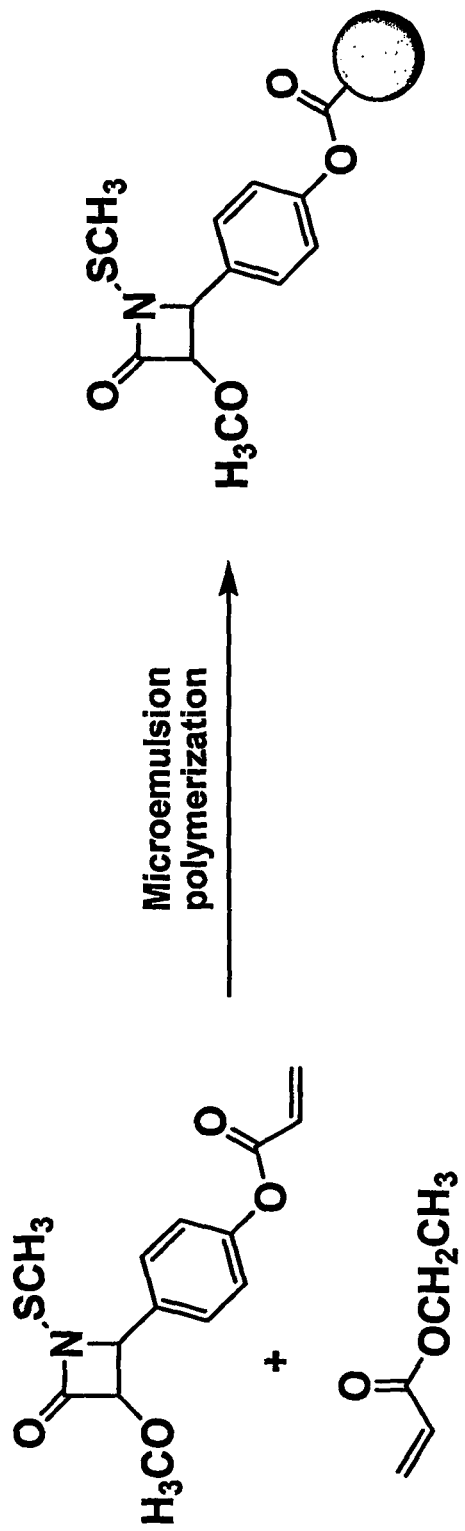
FIG. 42 shows the synthesis of nanoparticle polymers by microemulsion polymerization. The nanoparticles have pendant $C_4$ β-lactam analogs.

The $C_4$ acrylate analog was further polymerized in accordance with the methods of the subject invention, wherein the modified $C_4$ β-lactam and an acrylate become emulsified and undergo subsequent polymerization to form poly(acrylate) nanoparticles containing the drug (FIG. 42).

The resulting polymeric nanoparticle, wherein the drug is $C_4$ β-lactam, comprises about 15 wt % to about 20 wt % β-lactam acryloyl monomer and ethyl acrylate, about 1 wt % to about 3 wt % emulsifier and radical initiator, and about 80 wt % to about 85 wt % deionized water.

Figure 25:
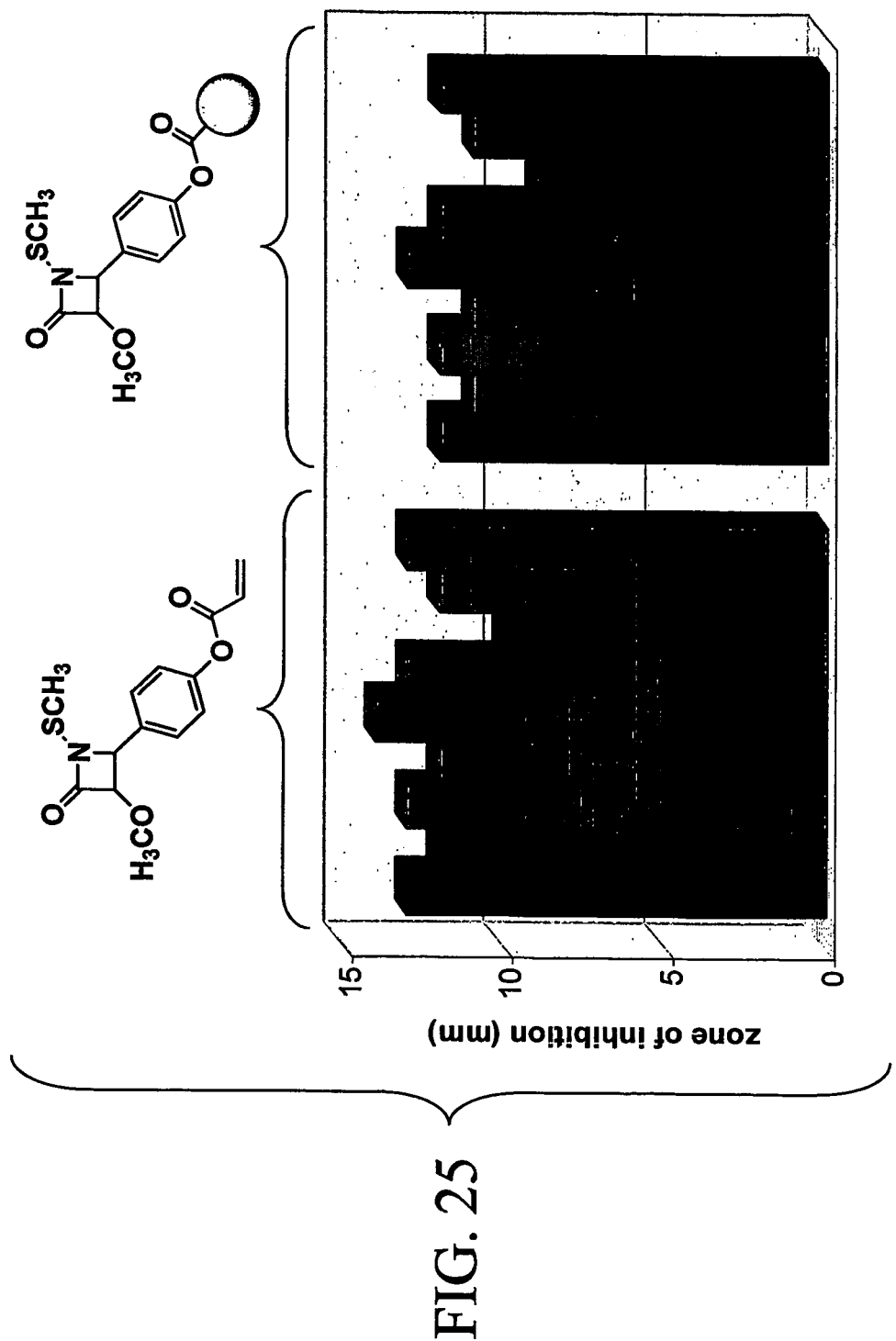
FIG. 25 shows a bar graph illustrating the antibacterial activities of $C_4$ acrylate β-lactam monomer and its emulsion polymeric nanoparticle against MRSA.

Samples of the modified $C_4$ analog monomer and the modified, polymerized $C_4$ analog nanoparticle were loaded into 6-mm wide holes bored in the agar, and the plate was incubated at 37° C. for 24 hours. The bioactivity of the modified $C_4$ analog monomer and the modified and polymerized $C_4$ analog nanoparticle are compared in FIG. 25.

Example 6

Figure 43A:
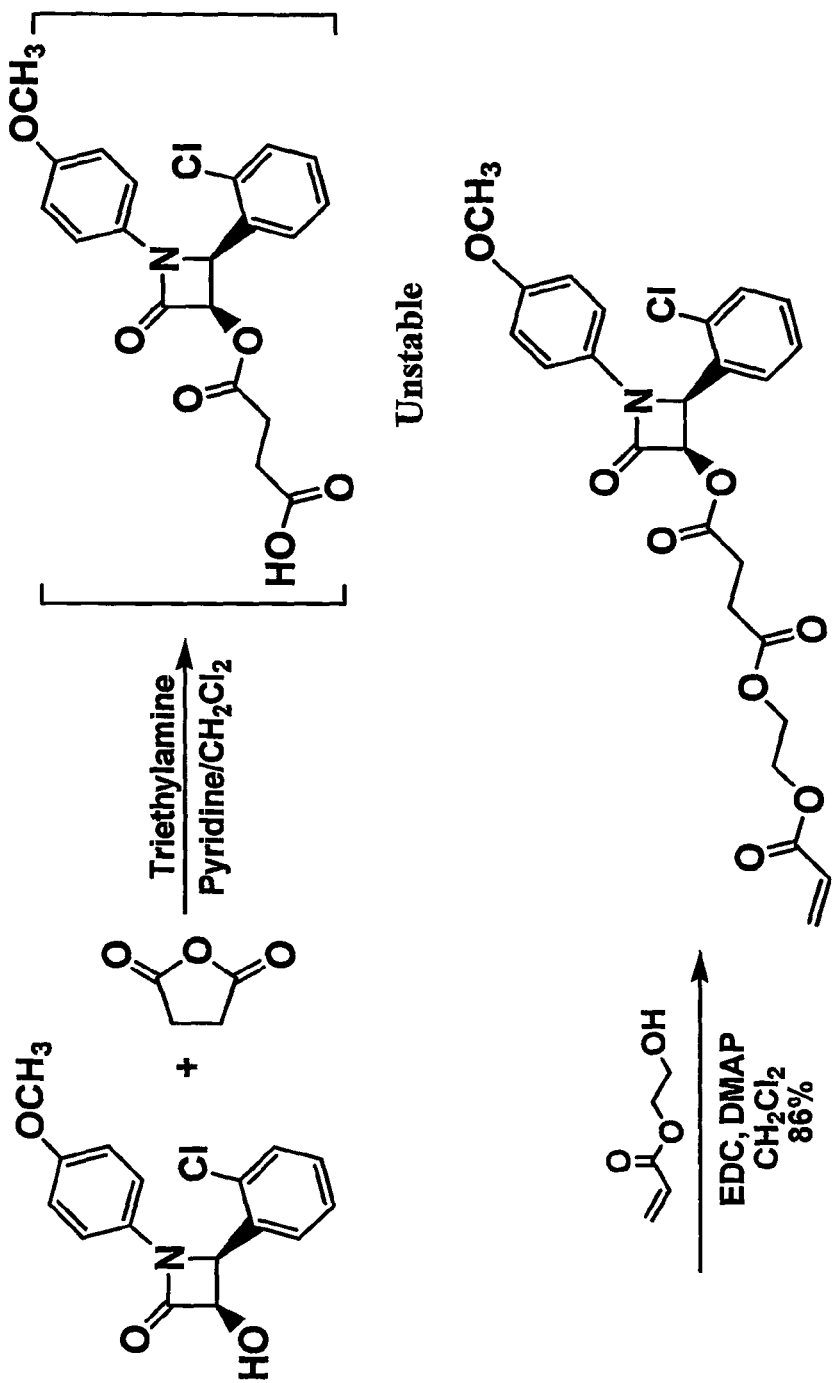
FIG. 43A shows step 1 of the preparation of a $C_3$ β-lactam analog—attaching a polyester acrylate side chain to $C_3$ with in situ generation of an unstable intermediate.
Figure 43B:
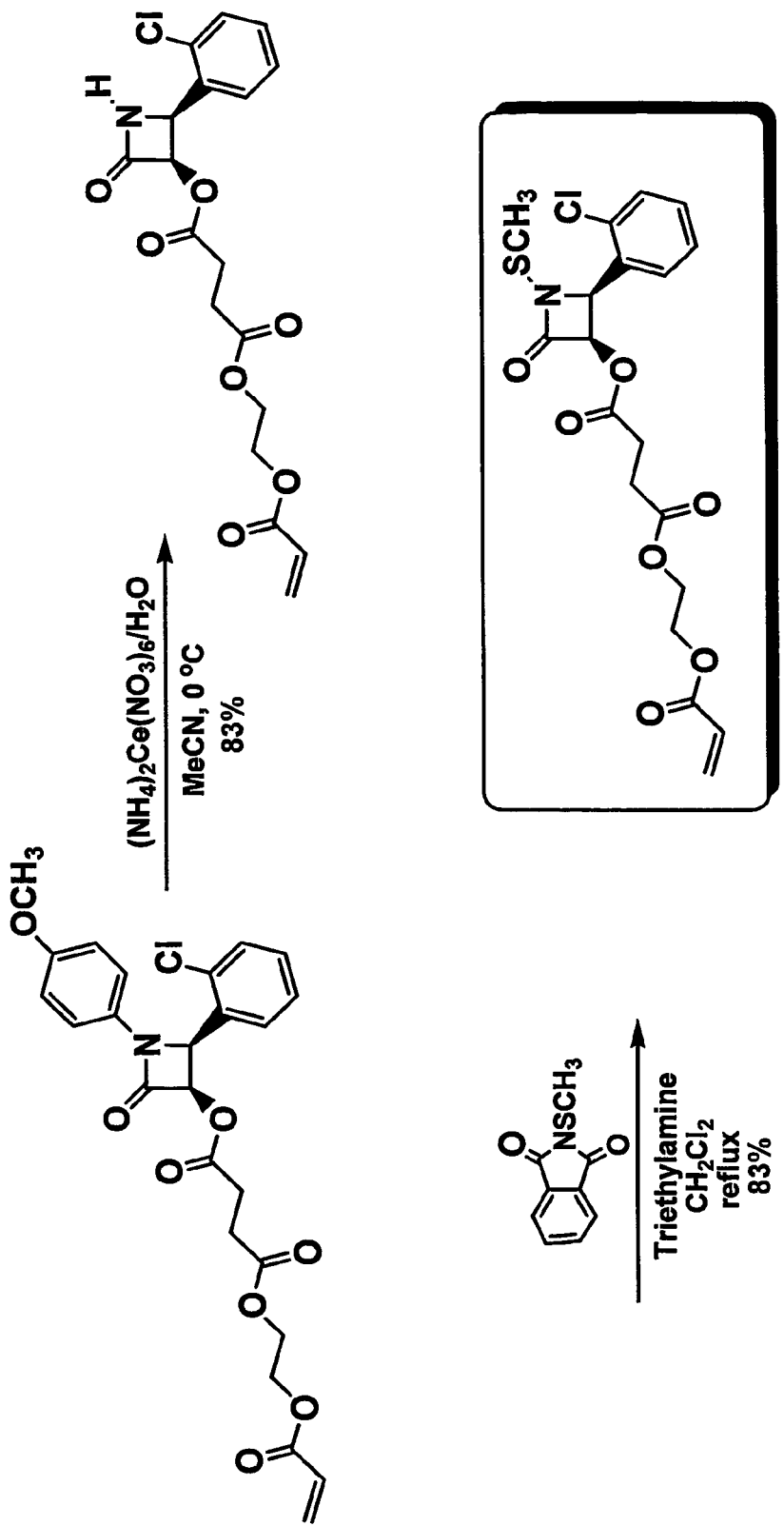
FIG. 43B shows step 2 of the preparation of a $C_3$ β-lactam analog—installing the methylthio side chain.

A $C_3$ polyester acrylate β-lactam analog was prepared as illustrated in FIGS. 43A and 43B. The $C_3$ analog is synthesized in a two step process when starting from a β-lactam. First, a polyester acrylate side chain is attached to the β-lactam at the $C_3$ position. Second, a methylthio side chain is attached to the nitrogen in the $C_1$ position.

Figure 29:
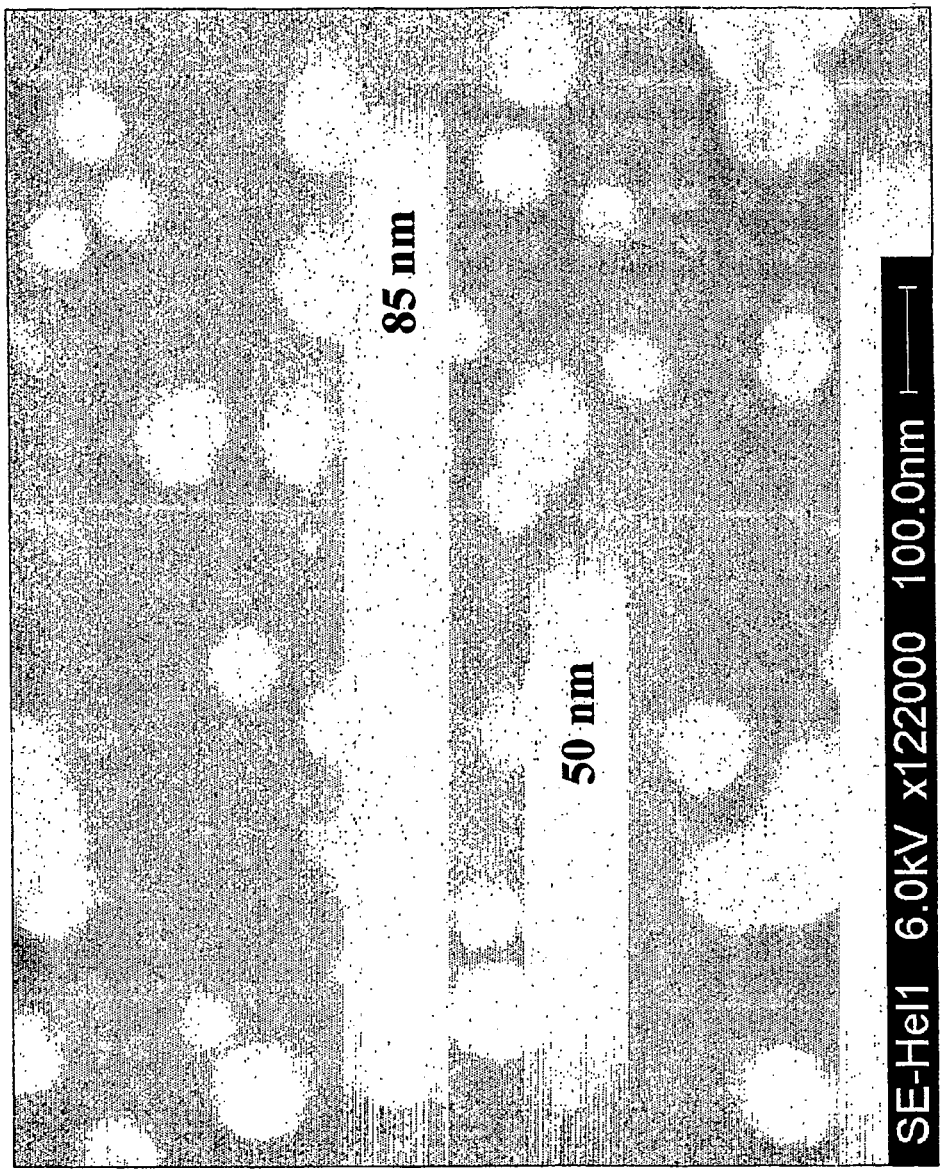
FIG. 29 shows a scanning electron micrograph for $C_3$ polyester β-lactam nanoparticles.
Figure 44:
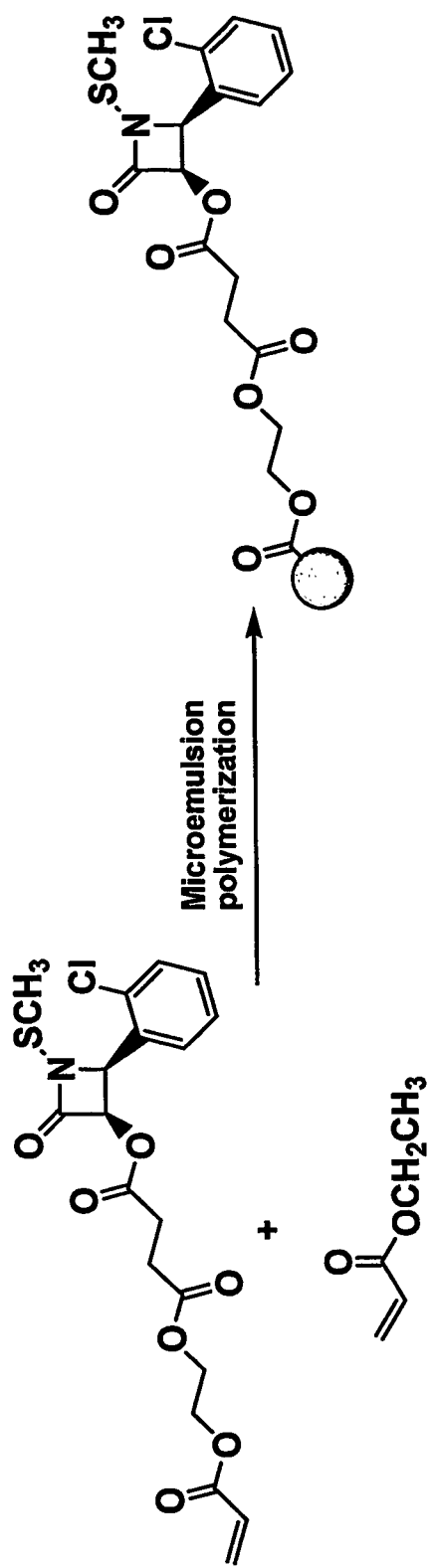
FIG. 44 shows the synthesis of nanoparticle polymers by microemulsion polymerization. The nanoparticles have pendent $C_3$ 9-lactam analogs.
Figure 45A:
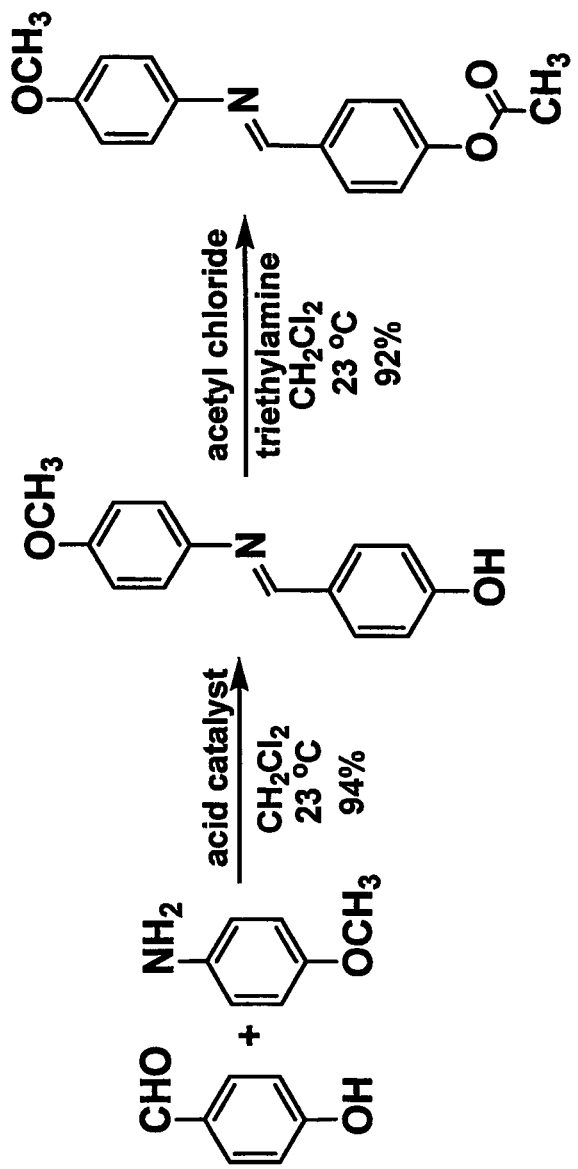
FIG. 45A shows step 1 in the preparation of a bis-acrylated β-lactam analog—synthesis of imine starting material. The acid catalyst is (1R)-(−)-10-camphorsulfonic acid.
Figure 45B:
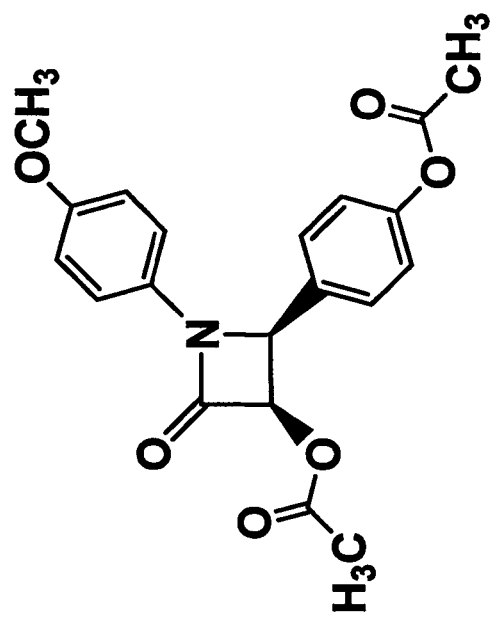
FIG. 45B shows step 2 in the preparation of a bis-acrylated β-lactam analog—conversion of imine to β-lactam.
Figure 45B:
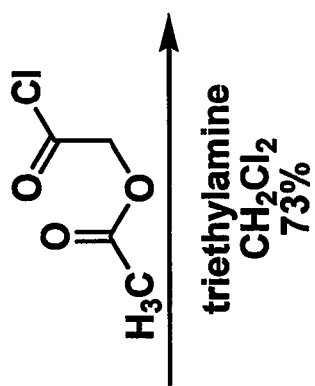
Figure 45B:
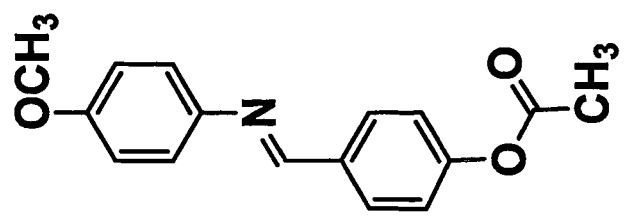
Figure 45C:
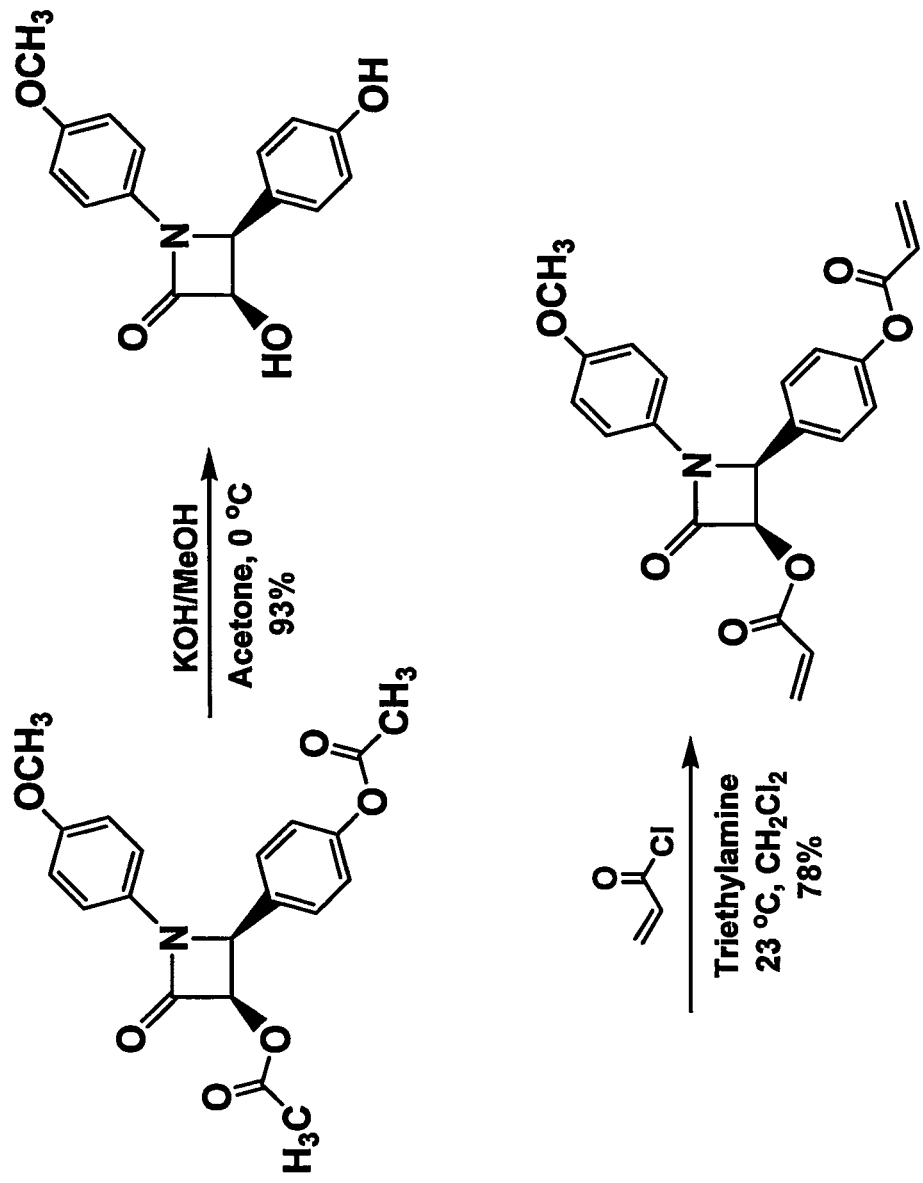
FIG. 45C shows step 3 in the preparation of a bis-acrylated β-lactam analog—replacing the acetoxy group for acrylates.
Figure 45D:
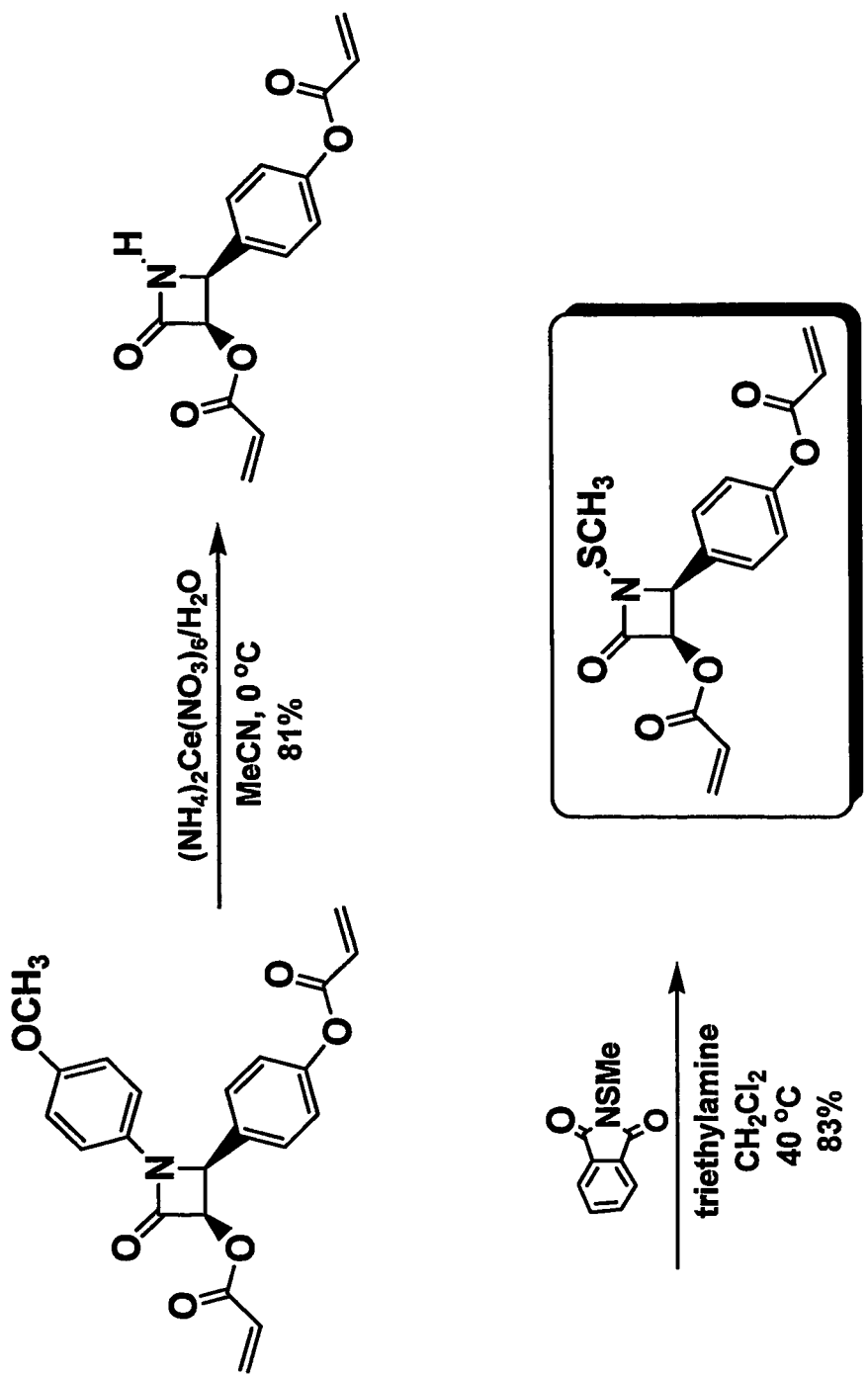
FIG. 45D shows step 4 in the preparation of a bis-acrylated β-lactam analog—replacing the N-aryl group for N—SMe.

The $C_3$ polyester acrylate β-lactam and an ethyl acrylate are emulsified and polymerized in accordance with the methods of the subject invention (FIG. 44), and a scanning electron microscopy (SEM) image of the nanoparticles is shown in FIG. 29.

The resulting drug nanoparticles comprise about 15 wt % to about 20 wt % β-lactam acryloyl monomer and ethyl acrylate, about 1 wt % to about 3 wt % emulsifier and radical initiator, and about 80 wt % to about 85 wt % deionized water.

Figure 26:
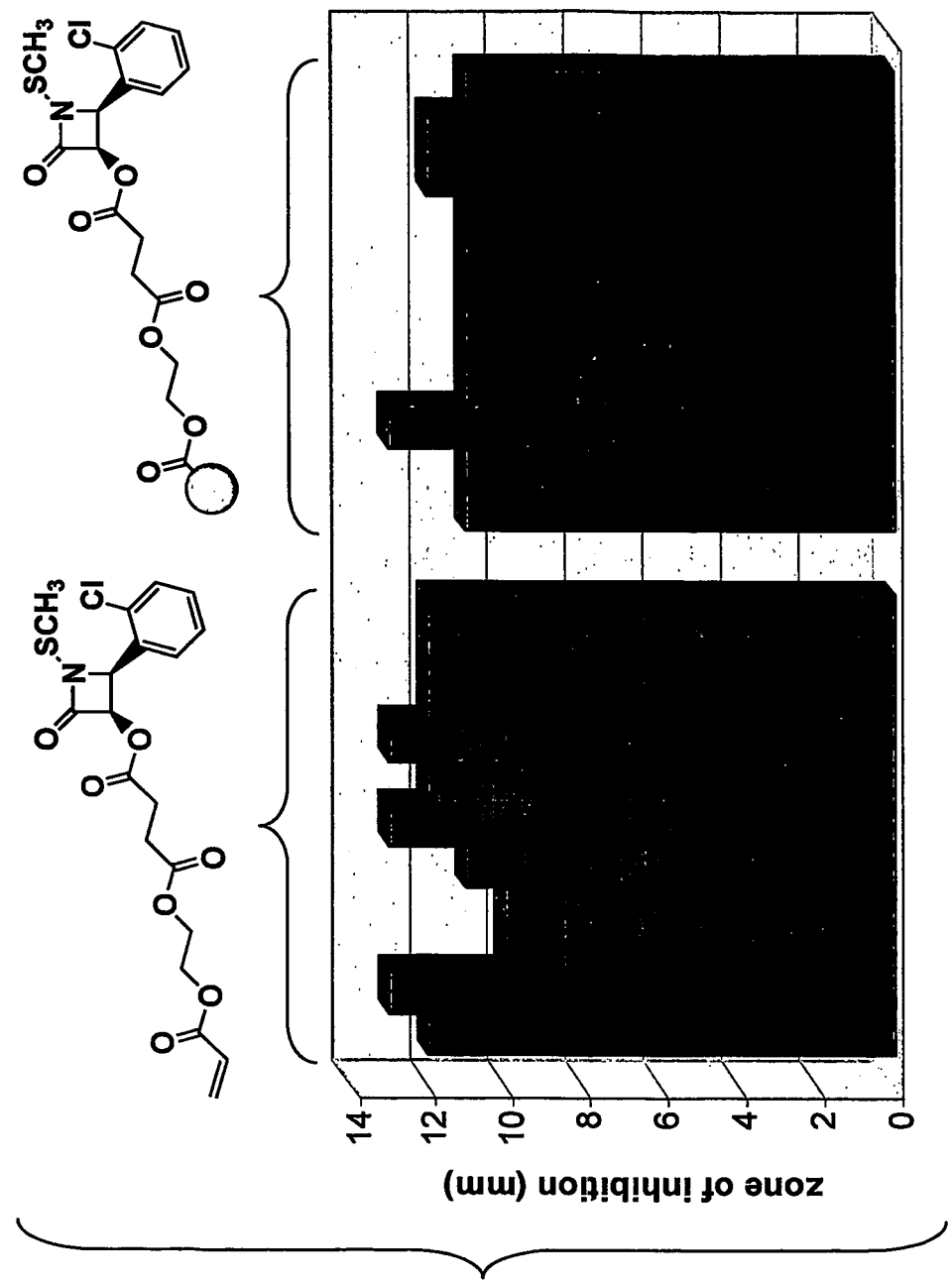
FIG. 26 shows a bar graph illustrating the antibacterial activities of $C_3$ polyester acrylate β-lactam monomer and its emulsion polymeric nanoparticle against MRSA.

Samples of the modified $C_3$ analog monomer and the modified, polymerized $C_3$ analog nanoparticle were loaded into 6-mm wide holes bored in the agar, and the plate was incubated at 37° C. for 24 hours. The bioactivity of the modified $C_3$ analog monomer and the modified and polymerized C3 analog nanoparticle are compared in FIG. 26.

Advantageously, the nanoparticle size is not affected by the location and the length of the polyacrylate linker that links the modified drug to the surface of the polymer backbone. However, without being limited by theory, the location and length of the polyacrylate linker possibly effects the biological activity against MSRA.

Example 7

A bis-acrylated β-lactam monomer was prepared as illustrated by FIGS. 45A-45D. Advantageously, the bis-acrylated β-lactam monomer was used to create crosslinks to different nanoparticles during the microemulsion polymerization in accordance with FIG. 30. Both acrylate groups on the bis-acrylated β-lactam are attached to the surface of different nanoparticles.

The preparation of bis-acrylated β-lactam is illustrated in FIGS. 45A-45D. The lactam is prepared by first synthesizing an imine, which is converted to a β-lactam. The two acetoxy groups on the $C_3$ and $C_4$ position are converted to acrylates, and the aryl group substituted on the nitrogen atom is replaced with a methylthio group.

Figure 46:
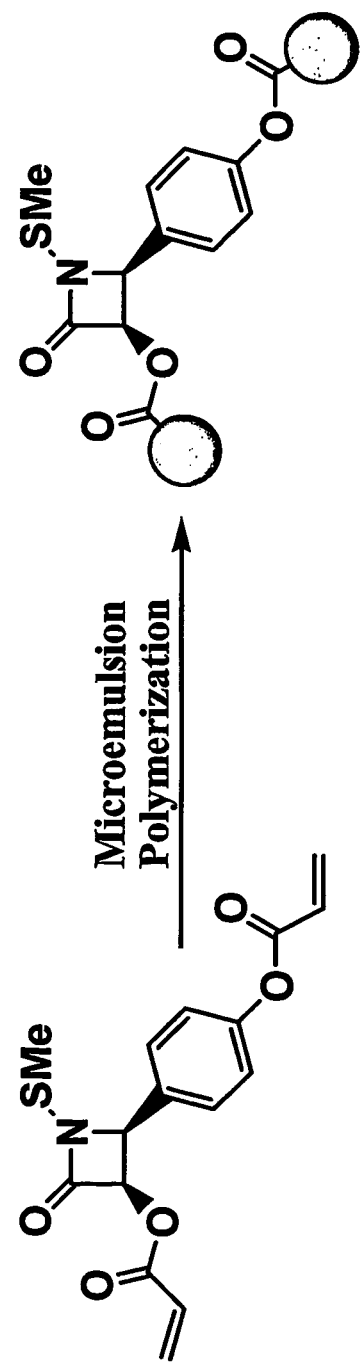
FIG. 46 shows the synthesis of nanoparticle polymers by microemulsion polymerization. The nanoparticles have pendent bis-acrylated β-lactam analog.

FIG. 46 illustrates the microemulsion polymerization to create a cross-linked nanoparticle. The modified and polymerized bis β-lactam nanoparticles comprise about 15 wt % to about 20 wt % β-lactam acryloyl monomer and ethyl acrylate, about 1 wt % to about 3 wt % emulsifier and radical initiator, and about 80 wt % to about 85 wt % deionized water. Because two linkers are attached to the bis-acrylate β-lactam monomer, there are two sites for attachment to the nanoparticles produced in accordance with the subject invention.

Figure 27:
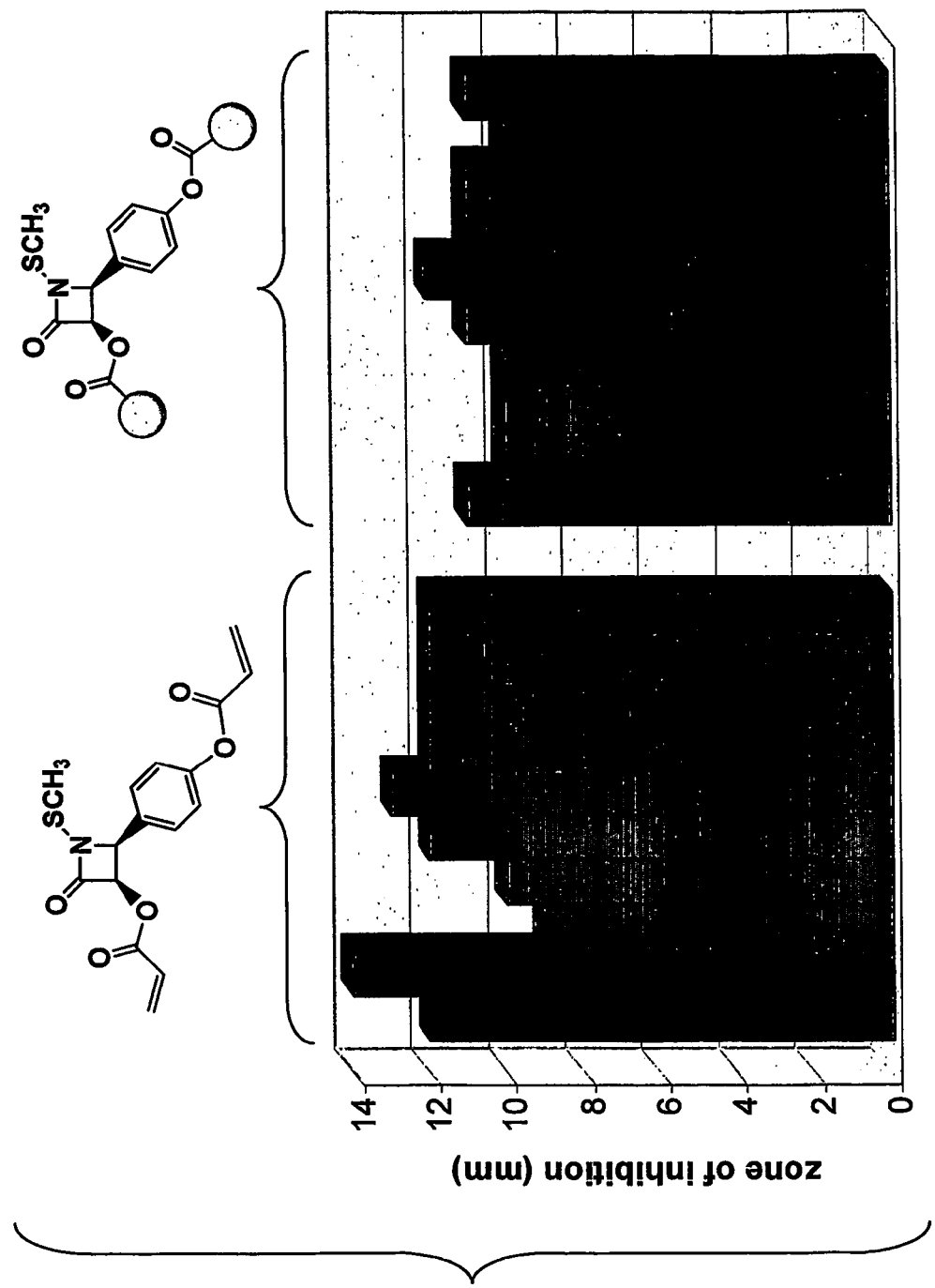
FIG. 27 shows a comparison of antibacterial activities of bis-acrylated monomer and its polymer against MRSA.

Samples of the modified bis-acrylated β-lactam monomer and the modified, polymerized bis analog nanoparticle were loaded into 6-mm wide holes bored in the agar, and the plate was incubated at 37° C. for 24 hours. The bioactivity of the modified analog monomer and the modified and polymerized analog nanoparticle are compared in FIG. 27.

Figure 28:
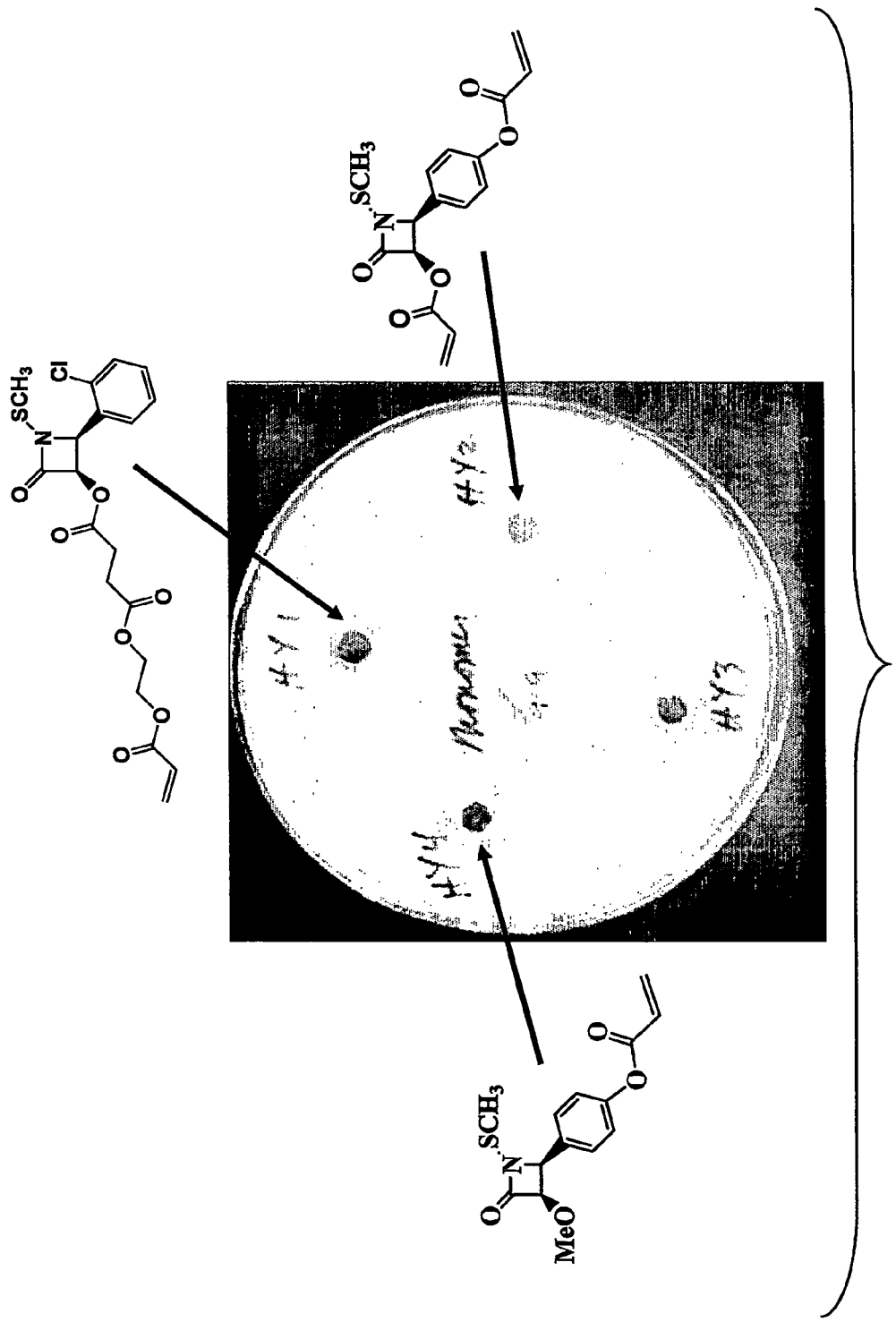
FIG. 28 shows a comparison of the antibacterial activities of three types of acrylate β-lactam monomers against MRSA.

A comparison of the antibacterial activities of the modified acrylate β-lactam monomers of Example 5, Example 6 and Example 7 is shown in FIG. 28. Changing the location and the length of the polyacrylate linker does not appear to affect particle size. However, these factors may affect the biological activity against MRSA. The cross-linker nanoparticle synthesized with bis-acrylated β-lactam shows weaker biological activity against MRSA.

Example 8

Methyl 2,3-O-iso-propylidine β-D-ribofuranose-5 acrylate was prepared in accordance with Scheme B and the methods of *Preparative Carbohydrate Chemistry*; Marcel Dekker, Inc.: New York, 1997; p. 16 and *Tetrahedron:Asynmmetry* 2001, 12, pp. 829-37.

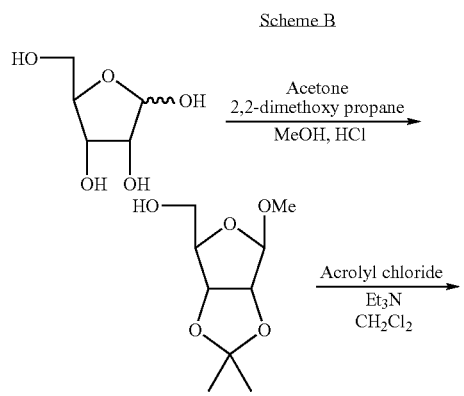

Scheme B

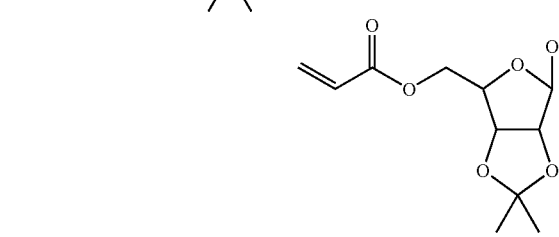

¹H NMR (250 MHz, CDCl3) δ=6.42, 1H, d(J=16.32); δ=6.10, 1H, dd(J=10.36, 10.36); δ=5.82, 1H, d (J=10.35); δ=4.92, 1H, s; δ=4.63, 1H, d(J=5.9); δ=4.55, 1H, d(J=5.93); δ=4.35, 1H, t(J=6.99); δ=4.11, 2H, d(J=6.01); δ=3.25, 3H, s; δ=1.42, 3H, s; δ=1.26, 3H, s.

The methyl 2,3-O-iso-propylidine β-D-ribofuranose-5 acrylate was polymerized in according to Scheme C.

Scheme C

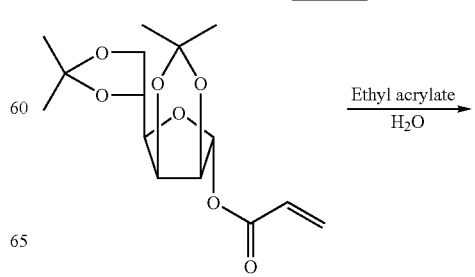

To a mixture of methyl 2,3-O-iso-propylidine-β-D-ribofuranose-5-acrylate (0.1 g) and Ethyl acrylate (0.8 g) 10 mg of Dodecyl sulfate in 4 ml water was added and stirred. Then, 5 mg of Potassium persulfate was added and stirred under Nitrogen at 50° C. for 10 hours.

Figure 31:
FIG. 31 shows a scanning electron micrograph for nanoparticles coated with D-ribose.

The formulation comprises about 15 wt % to about 20 wt % D-ribose acryloyl monomer and ethyl acrylate, about 1 wt % to about 3 wt % emulsifier and radical initiator; and about 80 to about 85 wt % deionized water. The resulting nanoparticles are within the range of 40 nm to 120 nm in diameter. A SEM image of the nanoparticles is shown in FIG. 31.

Example 9

2,3:5,6-Di-O-iso-propylidine-α-D-mannofuranose-1-acrylate was prepared in accordance with Scheme D.

Scheme D

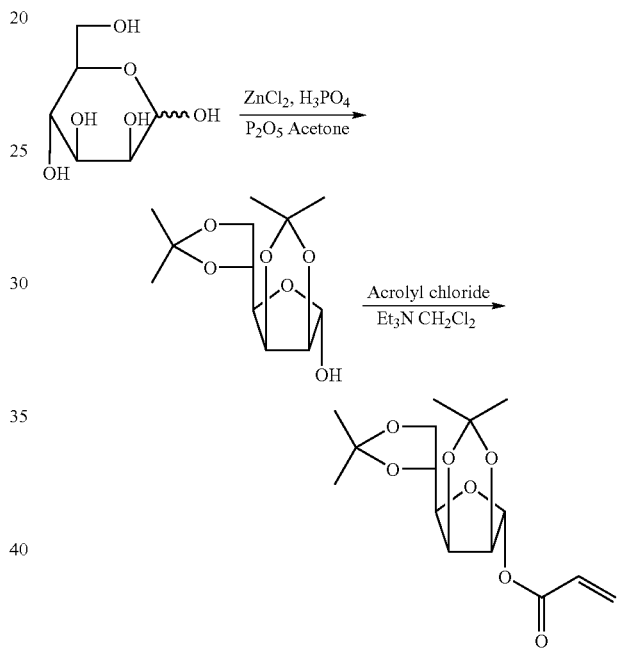

¹H NMR (250 MHz, CDCl3) δ=6.45, 1H, d (J=17.11); δ=6.17, 1H, s; δ=6.07, 1H, dd (J=10.38); δ=5.89, 1H, d (J=10.39); δ=4.85, 1H, m; δ=4.72, 1H, d (J=5.92); δ=4.37, 1H, m; δ=4.04, 3H, m; δ=1.44, 6H, d (J=9.19); δ=1.33, 6H, d (J=6.75).

The 2,3:5,6-Di-O-iso-propylidine-α-D-mannofuranose-1-acrylate was polymerized according to Scheme E.

Scheme E

-continued

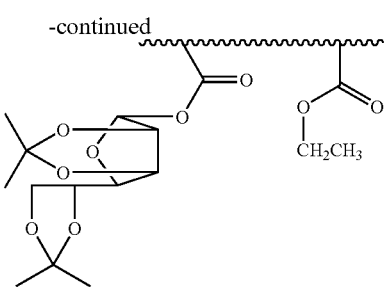

10 mg of dodecyl sulfate in 4 ml water was added to a mixture of 2,3:5,6-Di-O-iso-propylidine-α-D-mannofuranose-1-acrylate (0.1 g) and Ethyl acrylate (0.8 g) and stirred. Then, 5 mg of Potassium persulfate was added and stirred under Nitrogen at 50° C. for 10 hours. The D-mannose acrylol monomer and ethyl acrylate comprised about 15 wt % to about 20 wt %, the emulsider and radical initiator comprised about 1 wt % to about 3 wt %, and deionized water comprised about 80 wt % to about 85 wt % of the components.

Figure 32:
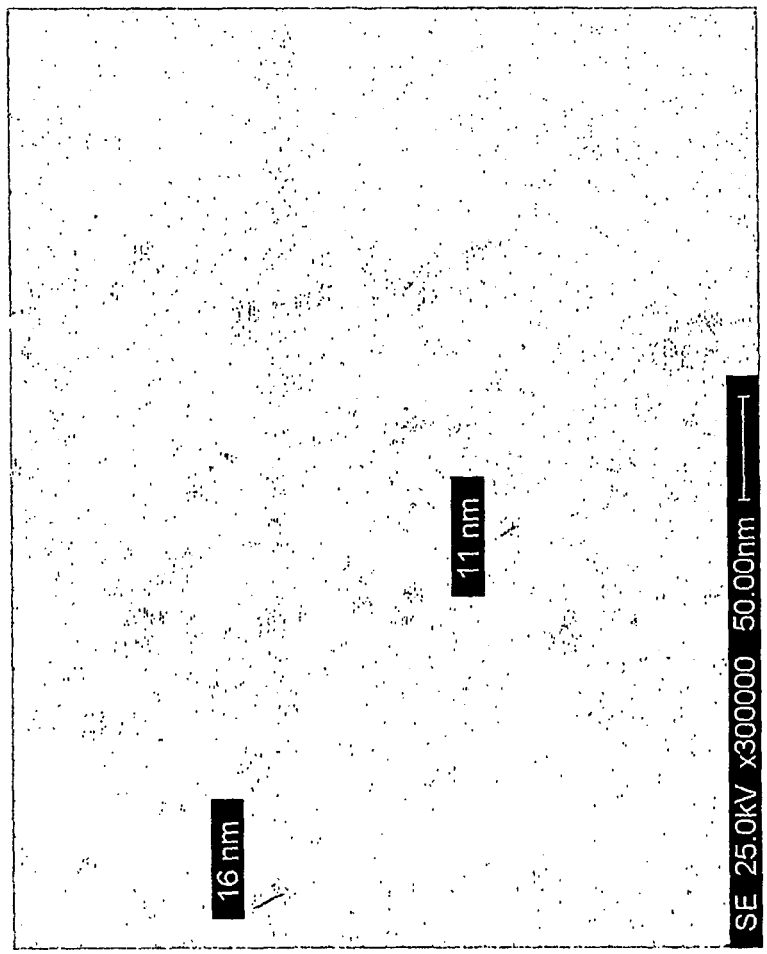
FIG. 32 shows a scanning electron micrograph of nanoparticles coated with D-mannose.

The diameters of the resulting nanoparticles varied from about 10 nm to about 40 nm. A SEM image of the D-mannose coated nanoparticles is shown in FIG. 32.

Example 10

1,2:5,6-Di-O-iso-propylidine-α-D-glucofuranose-3-acrylate was prepared in accordance with Scheme F and the techniques disclosed in *J. Am. Chem. Soc.* 1938, 60, 1507.

Scheme F

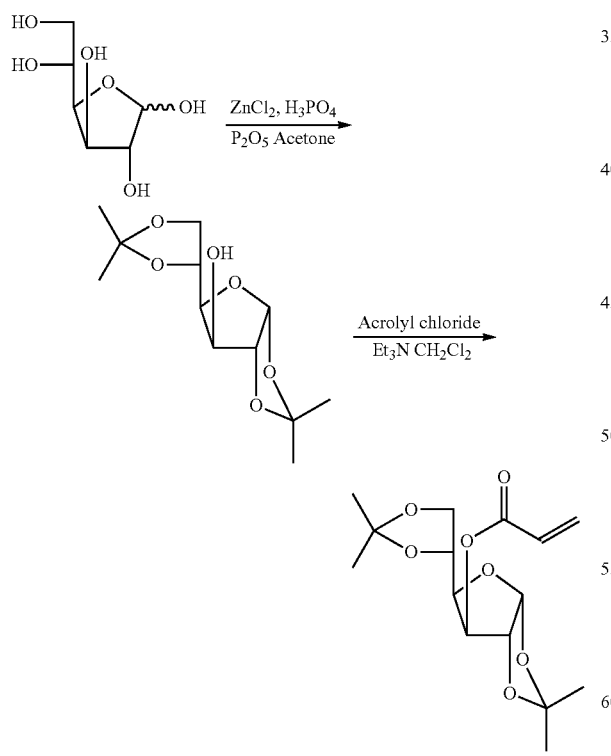

¹H NMR (250 MHz, CDCl3) δ=6.45, 1H, d (J=17.19); δ=6.14, 1H, dd (J=10.39, 10.37); δ=5.88, 2H, m; δ=5.28, 1H, br.s; δ=4.50, 1H, d (J=33.69); δ=4.20, 2H, m; δ=4.03-3.99, 2H, m; δ=1.48, 3H, s; δ=1.36, 3H, s; δ=1.26, 6H, s.

The 1,2:5,6-Di-O-iso-propylidine-α-glucofuranose-3-acrylate underwent microemulsion polymerized according to Scheme G.

Scheme G

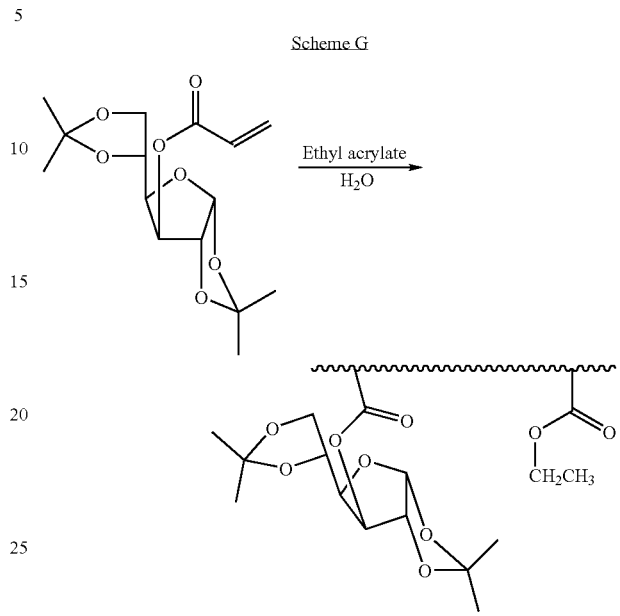

10 mg of Dodecyl sulfate in 4 ml water was added to a mixture of 1,2:5,6-Di-O-iso-propylidine-α-D-glucofuranose-3-acrylate (0.1 g) and Ethyl acrylate (0.8 g) and stirred. Then, 5 mg of Potassium persulfate was added and stirred under Nitrogen at 50° C. for 10 hours. The D-glucose acrylol monomer and ethyl acrylate comprised about 15 wt % to about 20 wt %, the emulsider and radical initiator comprised about 1 wt % to about 3 wt %, and deionized water comprised about 80 wt % to about 85 wt % of the components.

Figure 33:
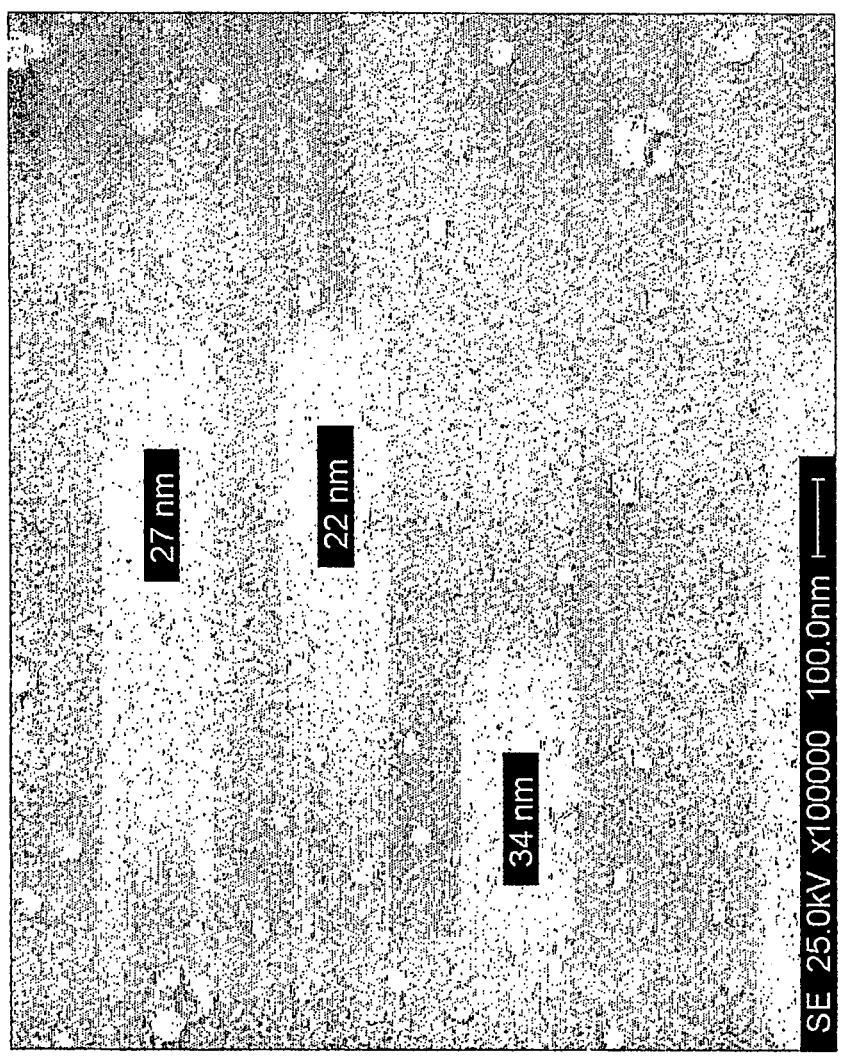
FIG. 33 shows a scanning electron micrograph of nanoparticles coated with D-glucose.
Figure 34:
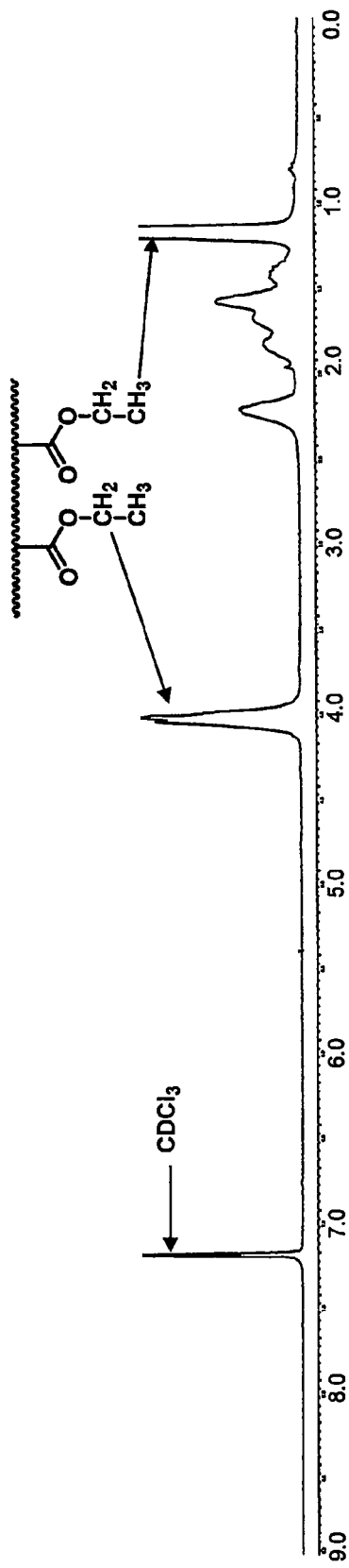
FIG. 34 shows a proton NMR spectrum of poly(ethylacrylate).
Figure 35:
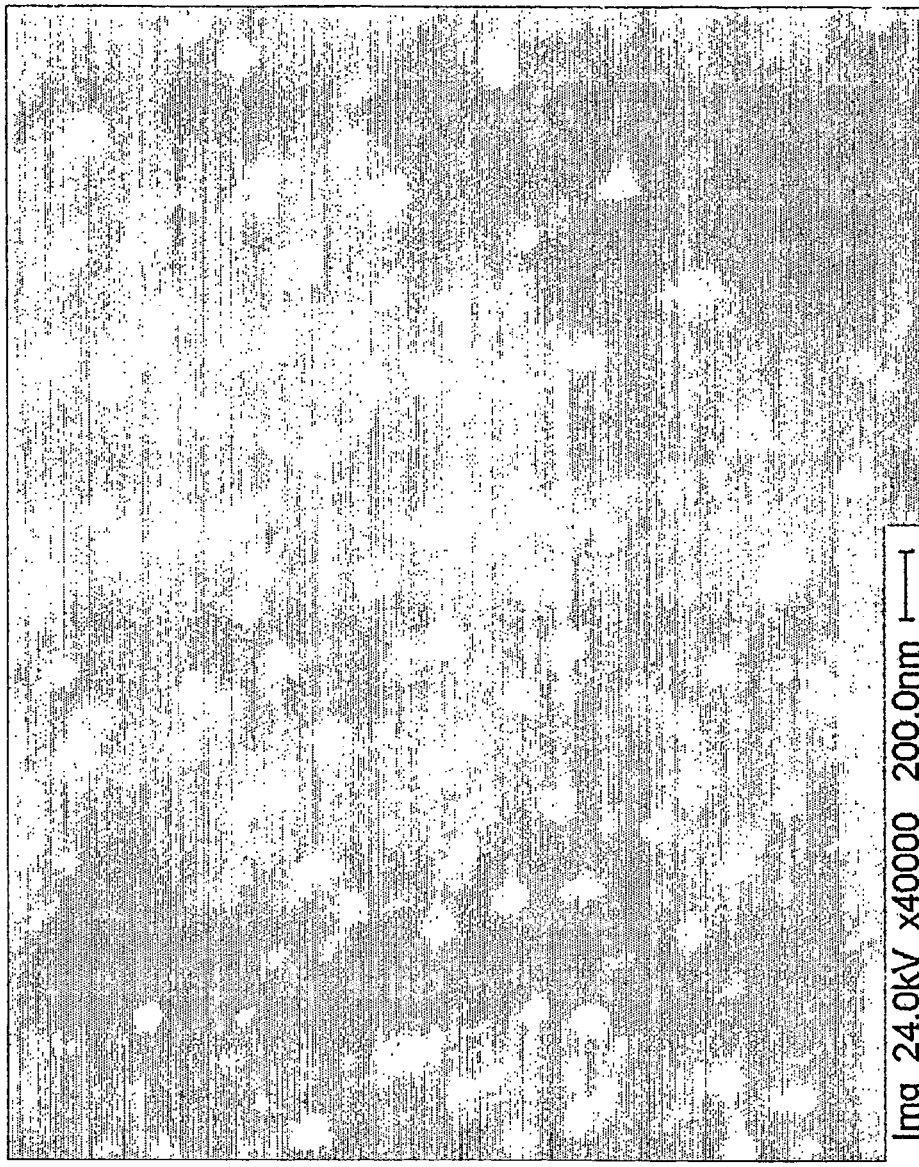
FIG. 35 shows a scanning electron micrograph of poly(ethyl acrylate) nanoparticles.

The diameters of the resulting nanoparticles varied from about 20 nm to about 50 nm. A SEM image of the D-mannose coated nanoparticles is shown in FIG. 33.

Example 11

1,2:3,4-Di-O-iso-propylidine-α-D-galactopyranose-6-acrylate was prepared in accordance with Scheme H.

Scheme H

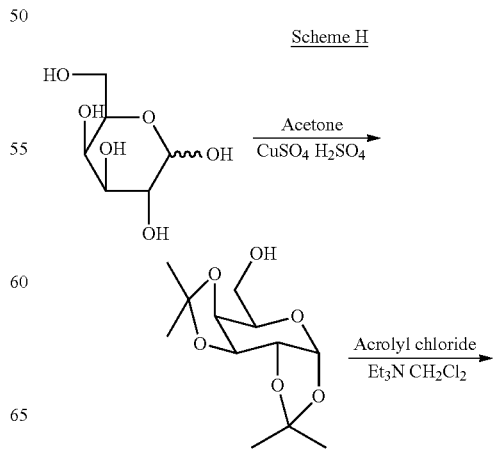

-continued

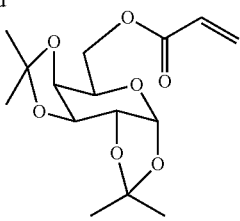

1H NMR (250 MHz, CDCl3) δ=6.40, 1H,d (J=17.19); δ=6.13, 1H, dd (J=9.34, 8.84); δ=5.52, 1H, br.s; δ=4.28, 4H, m; δ=4.05, 1H, br.s; δ=1.45, 6H, d (J=13.01); δ=1.31, 6H, s.

The 1,2:3,4-Di-O-iso-propylidine-α-galactopyranose-6-acrylate underwent microemulsion polymerization according to Scheme I.

Scheme I

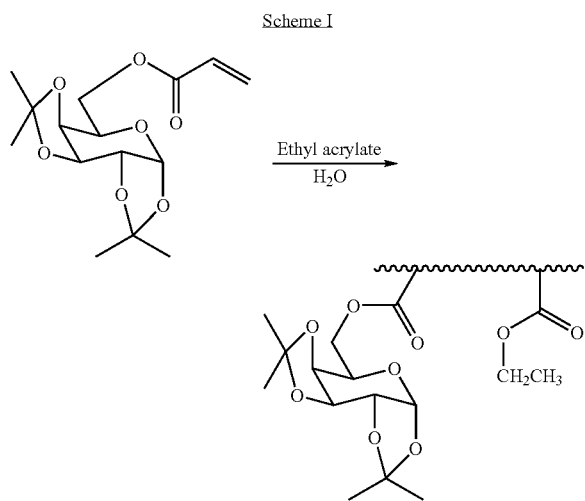

10 mg of Dodecyl sulfate in 4 ml water was added to a mixture of 1,2:3,4-Di-O-iso-propylidine-α-D-galactopyranose-6-acrylate (0.1 g) and Ethyl acrylate (0.8 g) and stirred. Then, 5 mg of Potassium persulfate was added and stirred under Nitrogen at 50° C. for 10 hours.

The D-galactose acrylol monomer and ethyl acrylate comprised about 15 wt % to about 20 wt %, the emulsifier and radical initiator comprised about 1 wt % to about 3 wt %, and deionized water comprised about 80 wt % to about 85 wt % of the components.

Example 12

Figure 47:
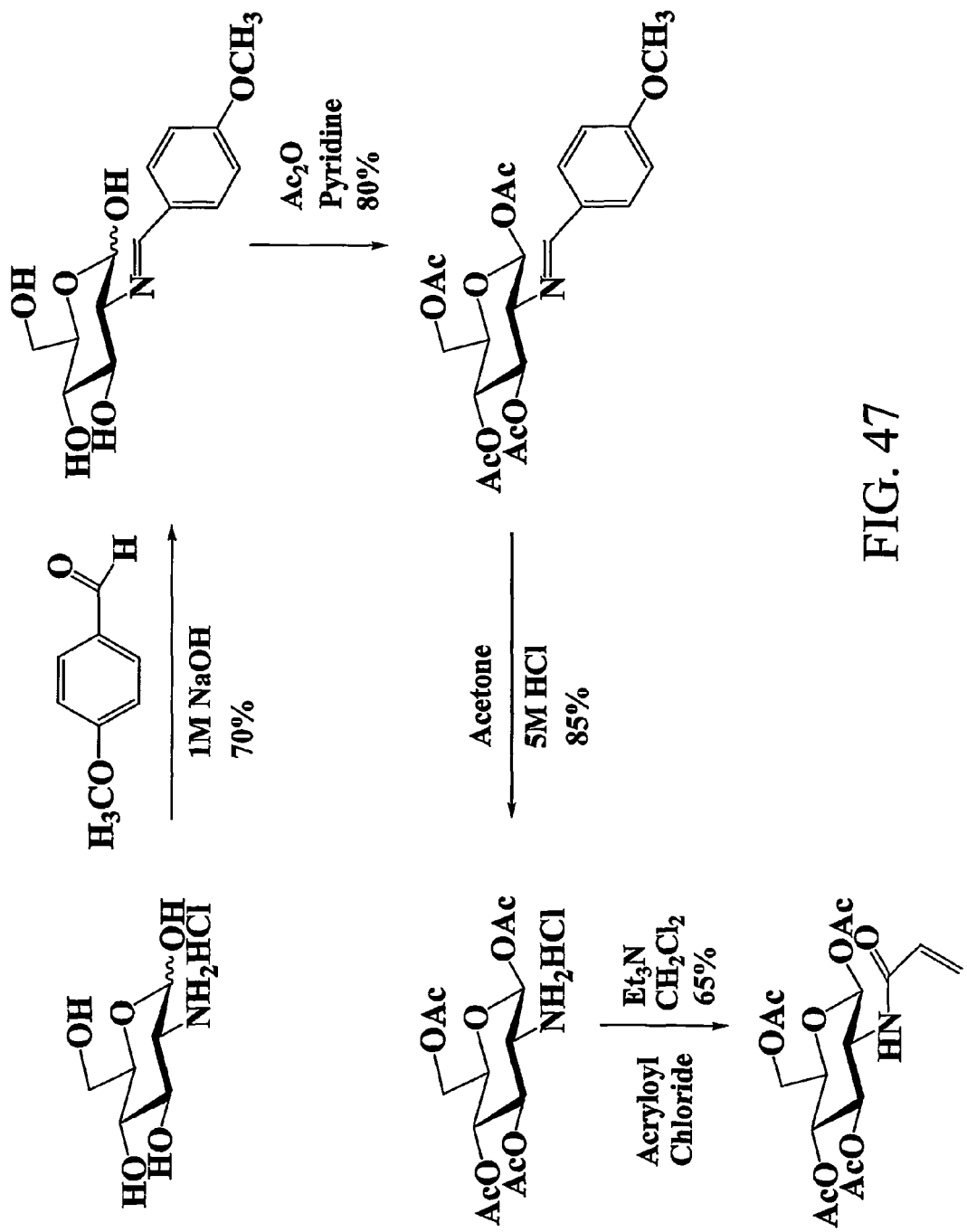
FIG. 47 shows a preparation of N-acryloyl 1,3,4,6-tetra-O-acetyl-β-D-glucosamine.
Figure 48:
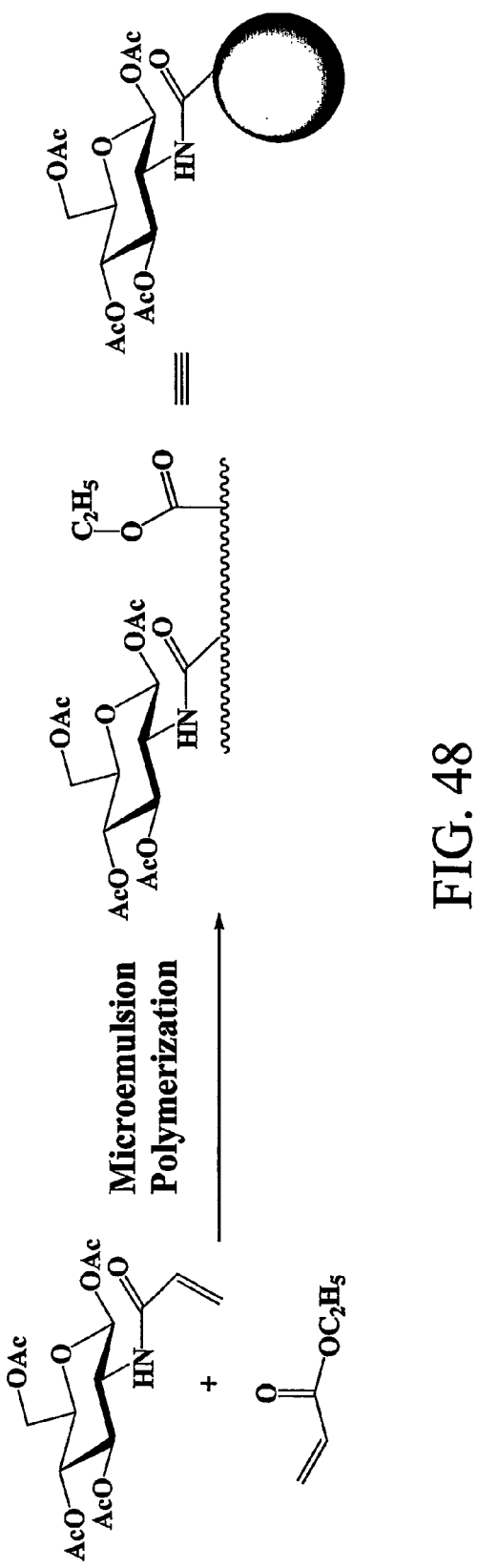
FIG. 48 shows the nanoparticle polymers by emulsion polymerization. The nanoparticle is coated with D-glucosamine.

N-acryloyl 1,3,4,6-tetra-O-acetyl-β-D-glucosamine was prepared according to FIG. 47 and techniques disclosed in Carbohydr. Res. 2003, 338, 133-141. The D-glucosamine acrylol monomer was polymerized according to the techniques of the subject application, as illustrated in FIG. 48. The components of the polymerization comprises 15 wt % to about 20 wt % D-glucosamine acrylol monomer and ethyl acrylate, 1 wt % to about 3 wt % emulsifier and radical initiator, and about 80 wt % to about 85 wt % deionized water.

Example 13

Figure 37:
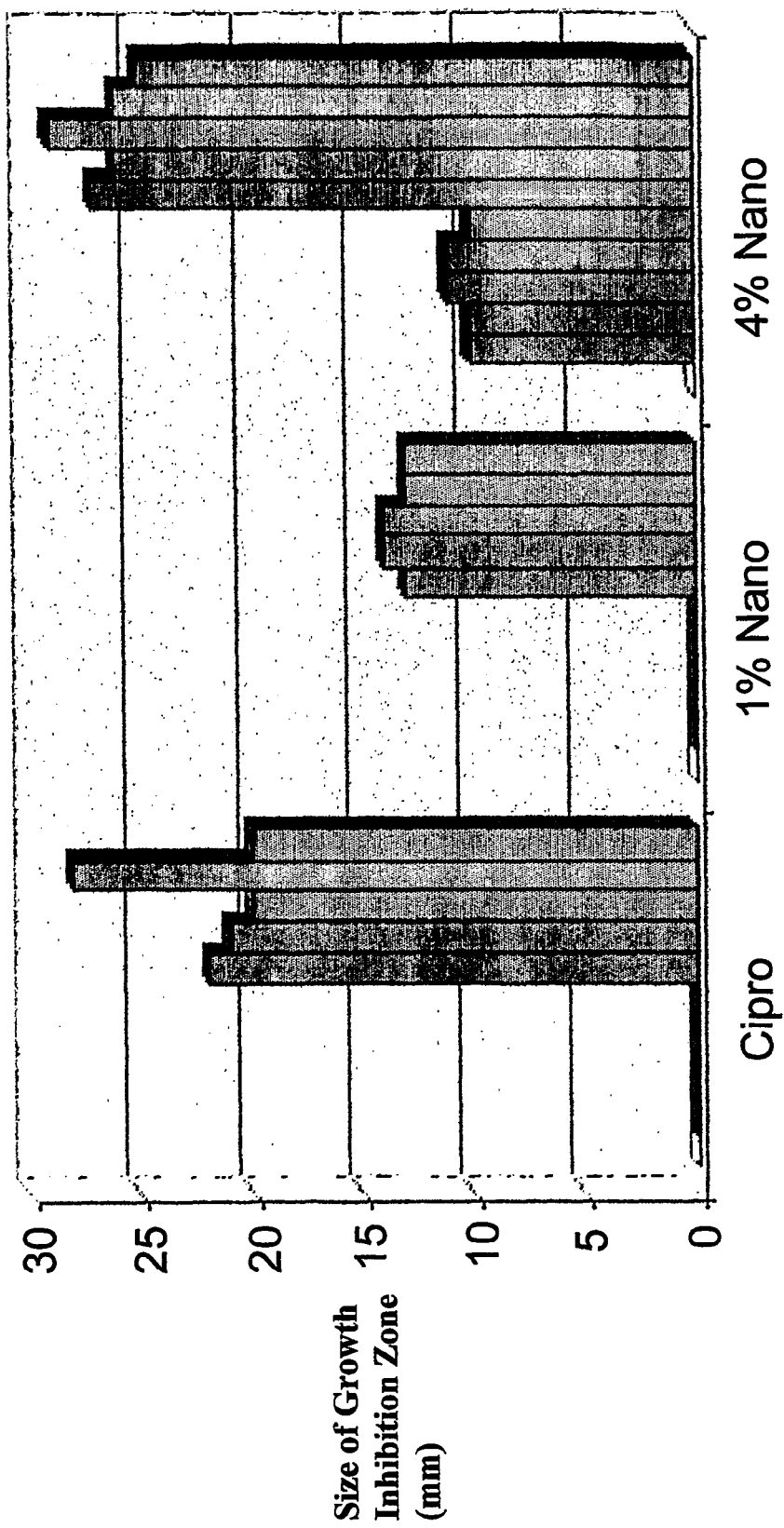
FIG. 37 shows a comparison of ciproflaxin nanoparticles against MRSA.
Figure 49:
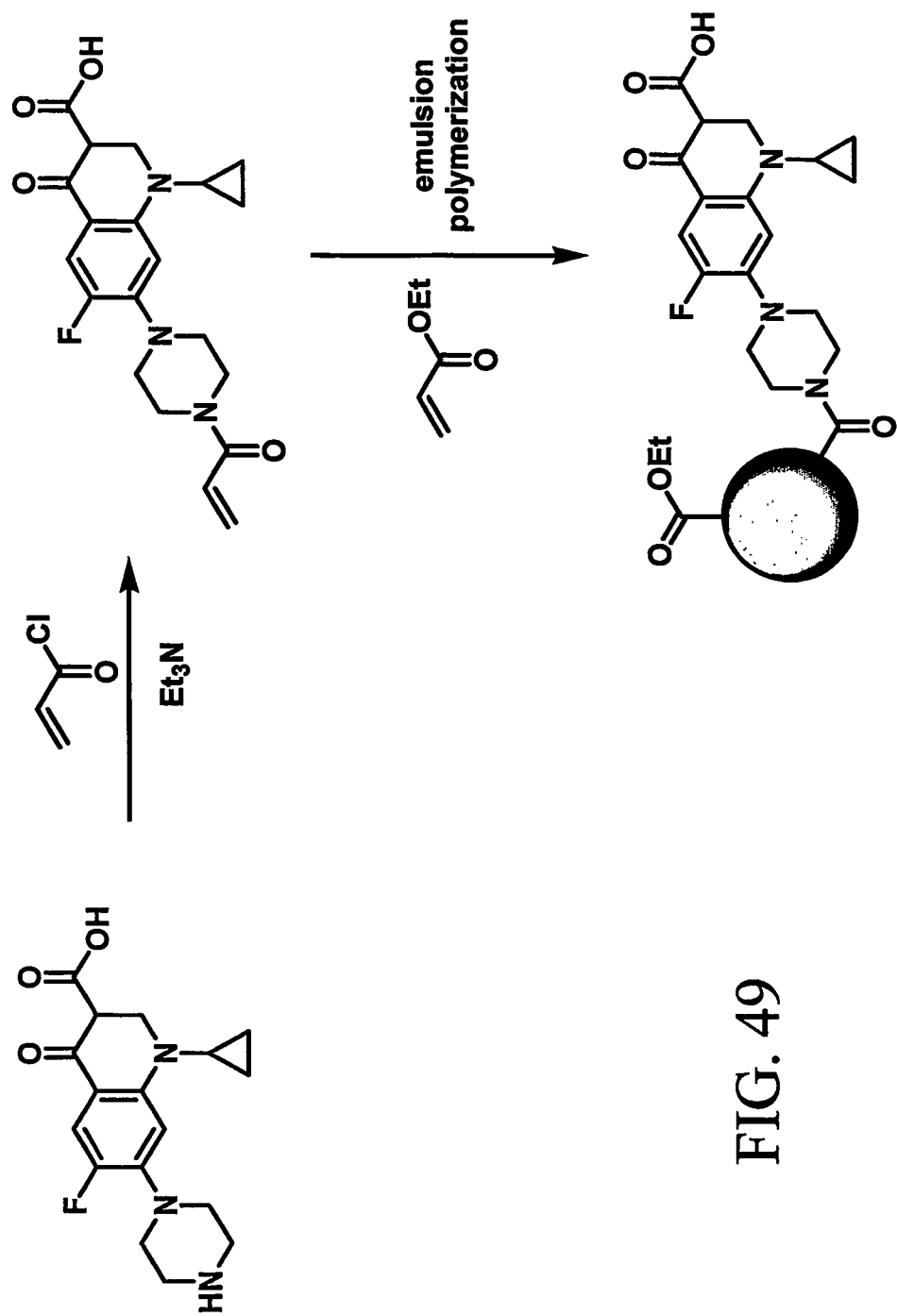
FIG. 49 shows the preparation of cipro-conjugated nanoparticles.
Figure 50:
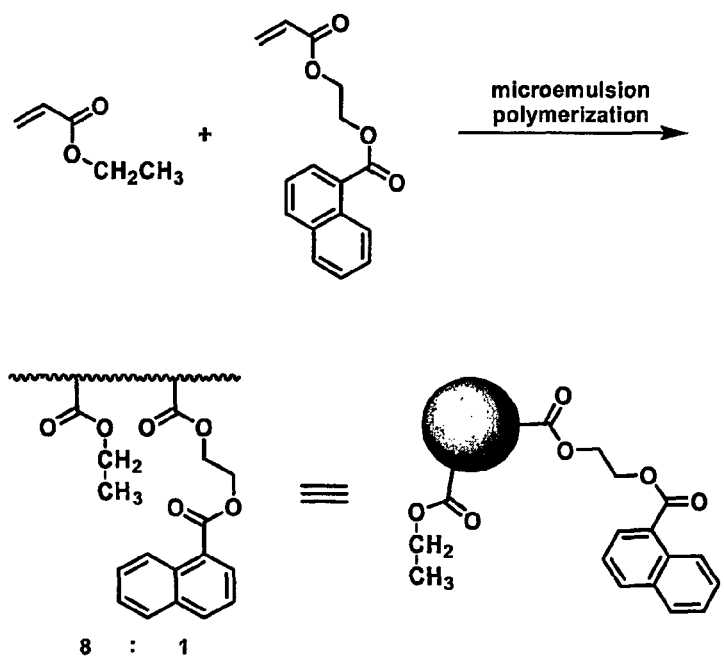
FIG. 50 shows a preparation of microemulsion polymerization of fluorescence-active naphthyl copolymeric nanoparticles.

Cipro-conjugated nanoparticles are produced in accordance to FIG. 49. Samples of ciprofloxacin only, 1% ciprofloxacin in nanoparticle, and 4% ciprofloxacin in nanoparticle were loaded into 6-mm wide holes bored in agar, and the plate was loaded with MRSA and incubated at 37° C. for 24 hours. The resulting bioactivities are compared in FIG. 37.

Example 14

β-Lactam containing fluorescence-active emulsified nanoparticles were successfully prepared with $C_3$-acryloyl N-methylthio β-lactam, naphthyl acrylate and ethyl acrylate at 70° C. After making a homogeneous solution of these three monomeric substances at 70° C., this mixture was dispersed in aqueous media containing the surfactant, sodium lauryl sulfate. Radical polymerization within this pre-formed particle mixture then was performed with an initiator (potassium persulfate) to give the nanospherical polymers. Its synthesis and formulation are described in FIG. 18 and Table 4 respectively.

TABLE 4

Formulation of Microemulsion Polymerization for Fluorescence-Active β-Lactam Copolymeric Nanoparticles.

| components | amount |
| --- | --- |
| ethyl acrylate (mg) | 170 |
| β-lactam acrylate (27) (mg) | 100 |
| naphthyl acrylate (33) (mg) | 50 |
| surfactant[1] (mg) | 7 |
| initiator[1] (mg) | 1.8 |
| deionized water (ml) | 2.0 |
| temperature (° C.) | 70 |

[1]surfactant: sodium laury sulfate; initiator: potassium persulfate

Dansyl acrylate was not used in the emulsion polymerization because it underwent the hydrolysis under the above conditions.

The naphthyl containing fluorescence-active emulsified nanoparticles (without the β-lactam drug) were prepared with naphthyl acrylate and ethyl acrylate in aqueous phase. A homogeneous solution of monomeric substances was made at room temperature and this mixture was dispersed in aqueous media with the aid of sodium lauryl sulphate at 60° C. Its synthesis and formulation are displayed in FIG. 50 and Table 5 respectively.

TABLE 5

Formulation of Microemulsion Polymerization for Fluorescence-Active Naphthyl Copolymeric Nanoparticles.

| components | amount |
| --- | --- |
| ethyl acrylate (mg) | 300 |
| naphthyl acrylate (33) (mg) | 100 |
| surfactant[1] (mg) | 8 |
| initiator[1] (mg) | 2.0 |
| deionized water (ml) | 3.0 |
| temperature (° C.) | 60 |

[1]surfactant: sodium laury sulfate; initiator: potassium persulfate

Anthracenyl fluorescence-active emulsified nanoparticles were also prepared with anthracenyl acrylate, styrene and butyl acrylate in aqueous phase at 70° C. A homogeneous solution of monomeric substances could be made with styrene and butyl acrylate at 70° C., and this mixture was dispersed in aqueous media containing a surfactant, sodium lauryl sulfate, to give the anthracenyl fluorescence-active nanoparticles as a milky emulsion. However, a homogeneous solution of monomeric substances could not be obtained with either ethyl acrylate and butyl acrylate since they could not dissolve the anthracenyl acrylate at 70° C. Its synthesis and the formulation are also displayed in FIG. 51 and Table 6 respectively.

TABLE 6

Formulation of Microemulsion Polymerization for Fluorescence-Active Anthracenyl Copolymeric Nanoparticles.

| components | amount |
| --- | --- |
| butyl acrylate (mg) | 700 |
| styrene (mg) | 300 |
| anthracenyl acrylate (34) (mg) | 10 |
| surfactant[1] (mg) | 20 |
| initiator[1] (mg) | 5.0 |
| deionized water (ml) | 5.0 |
| temperature (° C.) | 70 |

[1]surfactant: sodium laury sulfate; initiator: potassium persulfate

The morphology and the size of the emulsified particles were examined by Scanning Electron Microscopy (SEM). The sample of nanoparticles was prepared on a silicon wafer by evaporation of water under a gentle stream of air, and then coated with gold sputter under high vacuum. The gold-coated nanoparticles were then observed by SEM.

The SEM images of β-lactam, naphthyl, and anthracenyl fluorescence-active nanoparticles are displayed in FIGS. 21A, 22A, and 52, respectively. The images of nanoparticles show that the particles have spherical morphology and a particle size distribution of about 30-120 nm. FIGS. 21A and 52 also show that some of particles are fused by the coalescence due to not enough dilution of the samples when they are prepared.

$^1$H NMR Spectroscopy is a very useful tool to analyze the chemical structure of organic molecules. It can also be used to determine the mole ratio of each of the monomeric units, in copolymers. FIGS. 20B, 20D, and 53A show $^1$H NMR spectra for the dry films obtained by coalescing the nanoparticle emulsions of naphthyl (FIG. 20B), β-lactam (FIG. 20D), and anthracenyl (FIG. 53A) copolymer. The olefin protons of the acrylate moiety in the range of 5.6-6.1 ppm do not appear in the spectrum, indicating that all acrylic monomers participated in polymerization. In addition, each monomer-composition in the polymer was determined by the peak integration in the $^1$H NMR spectrum. For instance, the comparison of the peak integration for $C_3$ or $C_4$ proton of β-lactam, methylene protons of ethyl acrylate, and one of aromatic protons in naphthyl group in (FIG. 20D) spectra gave the mole ratio of each monomer in the copolymer.

The mole ratio of $C_3$-acryloyl N-methylthio β-lactam, naphthalyl acrylate, and ethyl acrylate in the polymer is 1:4.5: 0.6, and the particle size distribution is approximately 60-120 nm.

The mole ratio of ethyl acrylate and naphthyl acrylate in the polymer is 8:1 and the particle size distribution is approximately 30-60 nm. Anthracenyl fluorescence-active emulsified nanoparticles which have a different fluorescent emission were also prepared with butyl acrylate and styrene as co-monomers using microemulsion polymerization. The mole ratio of each monomer was not determined with $^1$H NMR spectra analysis since the peak integration of anthracenyl group is too small to detect. The particle size distribution is approximately 60-120 nm. Even though the emulsion polymerization was attempted with the monomer combination of ethyl acrylate-anthracenyl acrylate and the butyl acrylate-anthracenyl acrylate respectively, the anthracenyl emulsified nanoparticles were not prepared since neither monomer combinations could form a homogeneous liquid phase at 70° C.

Figure 54A:
FIGS. 54A-54D show comparison of the non-fluorescence-active β-lactam and the fluorescence-active naphthalyl and anthracenyl emulsified nanoparticles and their corresponding thin films upon IV irradiation.
Figure 54B:
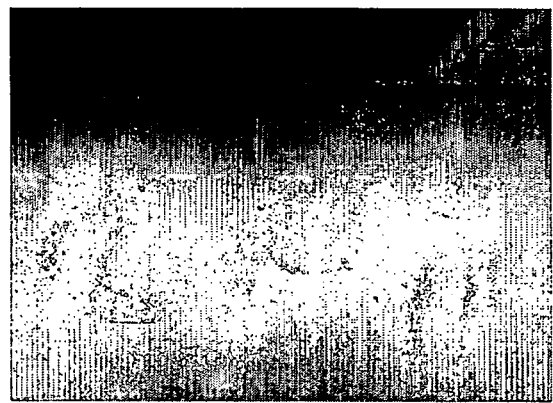
Figure 54D:
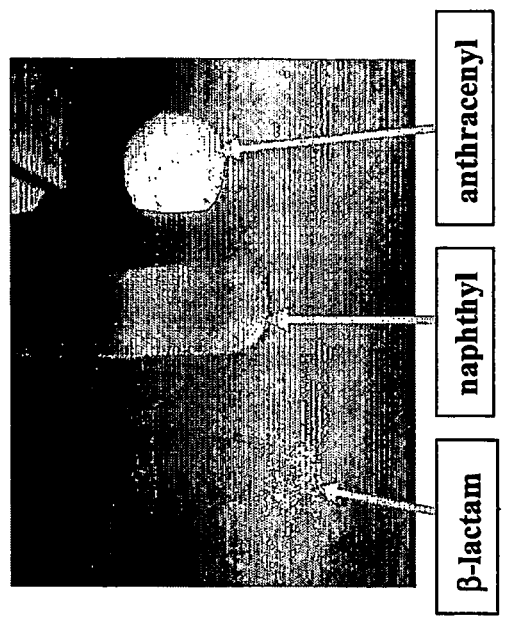
Figure 54C:
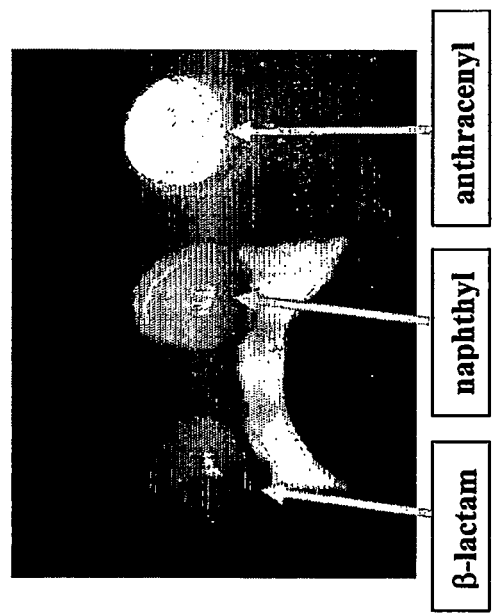

The fluorescent emission colors for a naphthyl and an anthracenyl emulsions and their corresponding thin films formed by coalescence were compared with non fluorescent β-lactam emulsion and its thin film upon UV irradiation. FIGS. 54A and 54C display the fluorescent emission colors for the non fluorescent β-lactam nanoparticles as well as that of naphthyl, and anthracenyl system upon UV irradiation. The non-fluorescent β-lactam emulsion shows no color change while both the naphthyl and anthracenyl nanoparticle emulsions emit a blue and a bright blue-green fluorescent color respectively. FIGS. 23B and 54A-54D also displays the fluorescent emission colors for the thin films of corresponding samples upon UV irradiation. Each sample shows the same fluorescent emission colors as in the emulsion. Therefore, naththyl and anthracenyl emulsified nanoparticles and their corresponding thin films are all fluorescence-active and emit a blue and a bright blue-green fluorescent color respectively.

To a solution of 2-hydroxyethyl acrylate (25.8 mg, 0.2 mmol) in 2 ml of freshly distilled $CH_2Cl_2$ was added diisopropylethylamine (DIPEA, 0.35 ml, 0.2 mmol) dropwise at 0° C. Dansyl chloride (50.0 mg, 0.19 mmol) was then added dropwise, and the resultant mixture was stirred at room temperature until TLC indicated the disappearance of starting material. The reaction was quenched with a 5% solution of $NH_4Cl$ and extracted (3×20 ml) with $CH_2Cl_2$. The combined organic layers were dried over anhydrous $MgSO_4$ and purified with column chromatography on silica gel (1:4, EtOAc: hexanes) to give 37.5 mg (56%) of 2-(5-dimethylamino-naphthalene-1-sulfonyloxy)-ethyl acrylate as a yellow semi solid. $^1$H NMR (250 MHz) δ 8.61 (d, J=8.6 Hz, 1H), 8.26 (t, J=6.3 Hz, 2H), 7.56 (m, 2H), 7.20 (d, J=7.7 Hz, 1H), 6.19 (dd, J=16.5, 2.5 Hz, 1H), 5.80 (dd, J=16.5, 10.3 Hz, 1H), 5.71 (dd, J=16.5, 10.3 Hz, 1H), 4.25 (m, 4H), 2.88 (s, 6H). $^{13}$C NMR (63 MHz) δ 158.0, 151.7, 131.8, 131.5, 130.9, 130.6, 129.8, 128.8, 127.3, 123.0, 119.4, 115.6, 67.8, 61.5, 45.4.

To a solution of 2-hydroxyethyl acrylate (1.01 g, 8.7 mmol) and 1-naphthoic acid (1.00 g, 5.8 mmol) in 10 ml of freshly distilled $CH_2Cl_2$ was added EDC (1.60 g, 8.7 mmol) and DMAP (cat. amount) at room temperature. The resultant mixture was stirred at room temperature until TLC indicated the disappearance of starting material. The reaction was quenched with a 5% solution of $NH_4Cl$ and the mixture was washed with water. After extraction with EtOAc (3×20 ml), the organic layers were dried over anhydrous $MgSO_4$ and purified with column chromatography on silica gel (1:4, EtOAc:hexanes) to give 1.29 g (82%) of naphthalene-1-carbonyloxy-2-ethyl acrylate as a colorless oil. $^1$H NMR (250 MHz) δ 8.91 (d, J=8.4 Hz, 1H), 8.21 (d, J=7.1 Hz, 1H), 8.04 (d, J=8.2 Hz, 1H), 7.90 (d, J=8.0 Hz, 1H), 7.57 (m, 3H), 6.49 (d, J=17.3 Hz, 1H), 6.19 (dd, J=17.3, 10.4 Hz, 1H), 5.71 (d, J=10.4 Hz, 1H), 4.66 (m, 2H), 4.58 (m, 2H). $^{13}$C NMR (63 MHz) δ 167.2, 165.9, 133.8, 133.6, 131.5, 131.3, 130.5, 128.6, 128.0, 127.8, 126.6, 126.2, 125.7, 124.5, 62.7, 62.3.

To a solution of 2-hydroxyethyl acrylate (0.78 g, 6.8 mmol) and 1-naphthoic acid (1.00 g, 5.8 mmol) in 10 ml of freshly distilled $CH_2Cl_2$ was added EDC (0.86 g, 4.5 mmol) and DMAP (cat. amount) at room temperature. The resultant mixture was stirred at room temperature until TLC indicated the disappearance of starting material. The reaction was quenched with a 5% solution of $NH_4Cl$ and the mixture was washed with water. After extraction with EtOAc (3×20 ml), the organic layers were dried over anhydrous $MgSO_4$ and purified with column chromatography on silica gel (1:4, EtOAc:hexanes) to give 0.30 g (21%) of anthracene-9-carbonyloxy-2-ethyl acrylate as a yellow solid, mp 66-68° C. $^1$H NMR (250 MHz) δ 8.54 (s, 1H), 8.06 (dd, J=14.7, 8.0 Hz, 4H), 7.52 (m, 4H), 6.21 (d, J=17.2 Hz, 1H), 6.21 (dd, J=17.2, 10.5 Hz, 1H), 5.91 (d, J=10.5 Hz, 1H), 4.89 (m, 2H), 4.62 (m, 2H). $^{13}$C NMR (63 MHz) δ 169.3, 165.3, 131.7, 130.9, 129.7, 128.7, 127.9, 127.1, 125.5, 124.9, 63.2, 62.3.

The mixture of 3-acryloyl N-methylthio β-lactam (100 mg, white solid, mp 92-93° C.), naphthyl acrylate (50 mg), and ethyl acrylate (170 mg) was warmed to 70° C. with slow stirring under a nitrogen atmosphere. Stirring was continued until the mixture was completely mixed to give a homogeneous liquid phase. Deionized water (1.7 ml) containing dodecyl sulfate, sodium salt (ACROS, 7 mg) was added with vigorous stirring and the mixture was stirred for one hour to give a milky pre-emulsion state. A solution of potassium persulfate (SIGMA, 1.8 mg) dissolved in deionized water (0.3 ml) was added under a nitrogen atmosphere and the mixture was stirred rapidly at 70° C. for 6 hours. A solution of potassium persulfate (0.5 mg) dissolved in deionized water (0.1 ml) was added to the emulsion and rapid stirring was continued for 1 hour to give the N-methylthio β-lactam containing fluorescence-active emulsified nanoparticles a milky emulsion. Other analogs were prepared similarly based on the formulation described in Table 5 and Table 6, respectively.

Samples of the nanoparticle emulsions were converted to thin films by coalescence as described in previous chapter. A rectangular cardboard frame was fixed on glass and the emulsion was poured into the frame. The emulsion was left to dry for 48 hours to give a transparent thin film.

We claim:

1. A polymeric nanoparticle comprising:
  a microemulsion polymerized nanoparticle consisting of a polymer comprising repeating units from acrylic monomers, optionally with additional repeating units from vinyl monomers, wherein at least one acrylic monomer is a bioaffecting agent, wherein the bioaffecting agent is covalently linked through a linkage comprising an ester moiety, an amide moiety, or imide moiety, and wherein the linkage is covalently linked to the bioaffecting agent through an oxygen atom or a nitrogen atom to the acrylic portion of the monomer, wherein the bioaffecting agent is present throughout the polymer nanoparticle.

2. The polymeric nanoparticle according to claim 1, wherein the nanoparticle further comprises a fluorescent active moiety, wherein the fluorescent active moiety fluoresces when exposed to ultraviolet light.

3. The polymeric nanoparticle according to claim 1, wherein the polymer comprises a plurality of repeating units from at least one polymerized monomer consisting of:
  an acrylic or vinyl monomer selected from the group consisting of acrylonitrile, acrylic acid, methyl acrylate, ethyl acrylate, butyl acrylate, butyl methacrylate, 2-ethylhexyl acrylate, methoxyethyl acrylate, dimethylamino acrylate, methacrylic acid, isobutyl methacrylate, 2-ethyl hexyl methacrylate, lauryl methacrylate, stearic methacrylate, dimethyl amino methacrylate, allyl methacrylate, modified acrylamide, modified methacrylamide glycidyl acrylate, styrene, vinyl acetate, vinyl toluene, synthetically modified acrylics, and a mixture of any of the foregoing; or a synthetically modified acrylic selected from the group consisting of methyl 2,3-O-isopropylidine-β-D-ribofuranose-5-acrylate, 2,3:5,6-Di-O-iso-propylidine-α-D-mannofuranose-1-acrylate, 1,2:5,6-Di-O-iso-propylidine-α-D-glucofuranose-3-acrylate, 1,2:3,4-Di-O-propylidine-α-D-galactopyranose-6-acrylate, N-acryloyl 1,3,4,6-tetra-O-acetyl-β-D-glucosamine, or an acrylic modified hydroxy protected D-glucose, acrylic modified hydroxy protected α-D-glucopyranose, acrylic modified hydroxy protected β-D-glucopyranose, acrylic modified hydroxy protected D-fructose, acrylic modified hydroxy protected α-D-fructofuranose, acrylic modified hydroxy protected D-fructopyranose, acrylic modified hydroxy protected D-ribose, acrylic modified hydroxy protected D-mannose, acrylic modified hydroxy protected D-galactose, acrylic modified hydroxy protected D-glucasamine, acrylic modified hydroxy protected amylase, acrylic modified hydroxy protected amylopectine, acrylic modified hydroxy protected cellulose, acrylic modified hydroxy protected sugar alcohol, acrylic modified hydroxy protected sugar acid, acrylic modified hydroxy protected amino sugars, acrylic modified hydroxy protected sialic acids, acrylic modified hydroxy protected maltose, acrylic modified hydroxy protected L-sorbose, acrylic modified hydroxy protected cellobiose, acrylic modified hydroxy protected sucrose, acrylic modified hydroxy protected lactose, acrylic modified hydroxy protected glycogen, acrylic modified hydroxy protected hyaluronate, acrylic modified hydroxy protected lectins, or an acrylic modified targeting agent; or
  a mixture of any of the foregoing.

4. The polymeric nanoparticle according to claim 1, wherein the diameter of the nanoparticle is within the range of about 1 nm to about 1000 nm, about 1 nm to about 400 nm, or about 1 nm to about 200 nm.

5. The polymeric nanoparticle according to claim 1, wherein the nanoparticle is spherical in aqueous solutions.

6. The polymeric nanoparticle according to claim 1, wherein the ratio of repeating units to the bioaffecting agent is about 2.5:1 to about 20:1.

7. The polymeric nanoparticle according to claim 3, wherein the targeting agent is selected from the group consisting of polypeptides, antibodies, receptor ligands, carbohydrates, lipids, folic acid, hormones, growth factors, antigens, and nucleic acids.

8. An emulsion comprising a polymeric nanoparticle according to claim 1; aqueous media; an emulsifier; and a radical initiator; wherein the nanoparticle is dispersed homogeneously in aqueous solution.

9. The emulsion according to claim 8, wherein the aqueous media is deionized water or nano-pure water.

10. The emulsion according to claim 8, wherein the emulsion comprises about 1 to 100 parts per weight of aqueous media, about 1 to 80 parts per weight of polymeric nanoparticle, about 0.001 to 10 parts per weight of emulsifier, and 0.00001 to 5 parts by weight of radical initiator.

11. The emulsion according to claim 8, further comprising a buffer solution.

12. A pharmaceutical composition comprising a polymeric nanoparticle according to claim 1, in a pharmaceutical carrier.

13. The pharmaceutical composition according to claim 12, wherein the polymeric nanoparticle is associated with more than one bioaffecting agent.

14. The polymeric nanoparticle according to claim 3, wherein the monomers comprise a mixture of butyl acrylate and styrene.

15. The polymeric nanoparticle according to claim 1, wherein the bioaffecting agent is selected from the group consisting of analgesics, anesthetics, anti-inflammatory agents, anthelmintics, anti-arrhythmic agents, antiasthma agents, antibiotics, anticancer agents, anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives, astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants, diagnostic agents, diagnostic imaging agents, diuretics, dopaminergics, free radical scavenging agents, growth factors, haemostatics, immunological agents, lipid regulating agents, muscle relaxants, proteins, peptides and polypeptides xanthines, alprazolam, amiodarone, amlodipine, astemizole, atenolol, azathioprine, azelatine, beclomethasone, β-lactam, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, penicillin, phenytoin, piroxicam, quinapril, ramipril, risperidone, sertraline, simvastatin, steroids, taxol, terbinafine, terfenadine, triamcinolone, valproic acid, zolpidem, expectorants, mucolytics, hypnotics, neuroleptics, and a pharmaceutically acceptable salt of any of the foregoing.

16. The polymeric nanoparticle according to claim 1, wherein the linkage comprises an ester.

17. The polymeric nanoparticle according to claim 1, wherein the linkage comprises an acrylate linker.

18. The polymeric nanoparticle according to claim 1, wherein the linkage comprises an acrylic or vinyl group.

19. The polymeric nanoparticle according to claim 1, wherein the bioaffecting agent comprises an antibiotic.

20. The polymeric nanoparticle according to claim 1, wherein the bioaffecting agent comprises a β-lactam, ciprofloxacin, or penicillin.

21. The polymeric nanoparticle according to claim 1, wherein the bioaffecting agent comprises a β-lactam.

22. The polymeric nanoparticle according to claim 18, wherein the β-lactam is selected from among C-4 acrylate N-methylthiolated β-lactam, C-3 polyester acrylate N-methylthiolated β-lactam, and bis-acrylated N-methylthiolated β-lactam.

23. The polymeric nanoparticle according to claim 1, wherein the linkage comprises an ester, and wherein the bioaffecting agent comprises β-lactam, ciprofloxacin, or penicillin.

24. The polymeric nanoparticle according to claim 1, wherein the linkage comprises an ester, and wherein the bioaffecting agent comprises a β-lactam.

25. The polymeric nanoparticle according to claim 1, wherein the linkage is cleavable by enzymatic hydrolysis endogenous to the bacterial cell.

26. The polymeric nanoparticle of claim 21, wherein the β-lactam is penicillin.

27. The polymeric nanoparticle of claim 21, wherein the β-lactam is an N-methylthiolated β-lactam.

28. The polymeric nanoparticle of claim 1, wherein the bioaffecting agent has been modified to include the acrylate moiety.

29. The polymeric nanoparticle of claim 1, wherein the linkage further comprises a carbohydrate.

30. The polymeric nanoparticle of claim 1, wherein the linkage comprises two or more ester moieties.

31. The polymeric nanoparticle of claim 1, wherein the ester moiety or substituted ester moiety comprises a polylactide.

32. The polymeric nanoparticle of claim 21, wherein the β-lactam is cefotaxime.

33. The polymeric nanoparticle of claim 21, wherein the β-lactam is cephalexin.

34. The polymeric nanoparticle of claim 26, wherein the penicillin is penicillin G.

35. The polymeric nanoparticle according to claim 3, further comprising a second polymerized monomer consisting of a synthetically modified acrylic that is modified with a fluorescent active moiety.

36. The polymeric nanoparticle according to claim 1, wherein the nanoparticle is spherical in shape.

37. A polymeric nanoparticle, comprising a nanoparticle consisting of a polymer prepared by a microemulsion polymerization of:
at least one acrylic monomer, wherein at least one acrylic monomer is a bioaffecting agent, wherein the bioaffecting agent is covalently linked through a linkage comprising an ester moiety, an amide moiety, or imide moiety, and wherein the linkage is covalently linked to the bioaffecting agent through an oxygen atom or a nitrogen atom to the acrylic portion of the monomer; and
an emulsifier, wherein the nanoparticle is spherical in shape; wherein the bioaffecting agent resides within the nanoparticle and is present throughout the nanoparticle, and wherein the nanoparticle is stable in an aqueous system.

38. The polymeric nanoparticle of claim 37, wherein the polymer is prepared by a microemulsion polymerization of the at least one acrylic monomer; the emulsifier; and
at least one vinyl monomer.

39. The polymeric nanoparticle of claim 1, wherein the bioaffecting agent is water insoluble.

40. The polymeric nanoparticle of claim 37, wherein the bioaffecting agent is water insoluble.

41. The polymeric nanoparticle of claim 1, wherein the non-acrylic portion of the monomer and the acrylic portion of the monomer are present in the nanoparticle in the ratio of 7:1.

42. The polymeric nanoparticle of claim 1, wherein the non-acrylic portion of the monomer and the acrylic portion of the monomer are present in the nanoparticle in the ratio of 20:1.

43. The polymeric nanoparticle of claim 37, wherein the non-acrylic portion of the monomer and the acrylic portion of the monomer are present in the nanoparticle in the ratio of 7:1.

44. The polymeric nanoparticle of claim 37, wherein the non-acrylic portion of the monomer and the acrylic portion of the monomer are present in the nanoparticle in the ratio of 20:1.

* * * * *

UNITED STATES PATENT AND TRADEMARK OFFICE
CERTIFICATE OF CORRECTION

PATENT NO. : 9,149,440 B2
APPLICATION NO. : 10/570461
DATED : October 6, 2015
INVENTOR(S) : Turos et al.

It is certified that error appears in the above-identified patent and that said Letters Patent is hereby corrected as shown below:

In the specification

Column 1,
Lines 18-21, "The subject matter of this application has been supported by a research grant from the National Institutes of Health under grant number R01 AI 51351. Accordingly, the government may have certain rights in this invention."

should read

--This invention was made with government support under Grant Number R01 AI051351 awarded by the National Institutes of Health. The government has certain rights in the invention.--.

Column 2,
Line 65, "by, the" should read --by the--.

Column 7,
Line 49, "contents (%)." should read --contents (%)).--.

Column 8,
Line 17, "fluoresce-active" should read --fluorescence-active--.
Line 56, "MSSA" should read --MRSA--.

Column 10,
Line 31, "invention Without" should read --invention. Without--.

Column 12,
Lines 55-56, "1,3,4,6-tetra-O-acetyl-g-D-glucosamine." should read --1,3,4,6-tetra-O-acetyl-β-D-glucosamine.--.

Signed and Sealed this
Tenth Day of May, 2016

Michelle K. Lee
*Director of the United States Patent and Trademark Office*

Column 13,
Line 11, "nonionic" should read --non-ionic--.

Column 15,
Line 44, "acts a linker" should read --acts as a linker--.

Column 18,
Line 59, "some PR" should read --some FR--.
Line 65, "Boemer" should read --Boerner--.

Column 19,
Line 1, "Boemer" should read --Boerner--.

Column 20,
Line 15, "*Comyebacterium,*" should read --Cornyebacterium,--.

Column 21,
Line 59, "IgG," should read --$IgG_1$--.

Column 23,
Line 32, "take form" should read --take the form--.

Column 24,
Line 38, "blocling" should read --blocking--.

Column 27,
Line 52, "4-lactam" should read --β-lactam--.

Column 34,
Line 18, "polymerized C3" should read --polymerized $C_3$--.

Column 43,
Lines 2-3, "4.62 (m, 21)." should read --4.62 (m, 2H).--.